US011881311B1

(12) United States Patent
Fortney et al.

(10) Patent No.: US 11,881,311 B1
(45) Date of Patent: Jan. 23, 2024

(54) SURVIVAL PREDICTION USING METABOLOMIC PROFILES

(71) Applicant: BIOAGE LABS, INC., Berkeley, CA (US)

(72) Inventors: Kristen Patricia Fortney, Crockett, CA (US); Yonatan Nissan Donner, Sunnyvale, CA (US); Eric Kim Morgen, Toronto (CA); Jonah Daniel Sinick, Berkeley, CA (US); Andrew Jarai Ho, Berkeley, CA (US)

(73) Assignee: BioAge Labs, Inc., Richmond, CA (US)

( * ) Notice: Subject to any disclaimer, the term of this patent is extended or adjusted under 35 U.S.C. 154(b) by 1261 days.

(21) Appl. No.: 15/891,295

(22) Filed: Feb. 7, 2018

Related U.S. Application Data

(60) Provisional application No. 62/572,378, filed on Oct. 13, 2017, provisional application No. 62/460,648, filed on Feb. 17, 2017.

(51) Int. Cl.
*G16H 50/30* (2018.01)
*G01N 33/50* (2006.01)
*G16B 40/00* (2019.01)

(52) U.S. Cl.
CPC ......... *G16H 50/30* (2018.01); *G01N 33/5008* (2013.01); *G16B 40/00* (2019.02)

(58) Field of Classification Search
CPC ........... G01N 2800/50; G01N 2800/56; G01N 2800/60; G01N 33/50; G01N 33/82; G01N 33/84; G01N 33/92; G01N 33/96; G01N 2560/00; G01N 2570/00; G16H 50/30; G16H 50/20; G16H 50/50; G16H 10/40; G16H 50/70; G16H 70/60; G16B 20/00; G16B 25/10; G16B 40/00; G16B 40/20; G16B 40/30; G16B 5/00; G16B 40/10; G16B 5/20; G16B 50/00; G16B 50/30; G16B 45/00; G16C 20/30; G16C 20/70; G16C 20/20; G16C 20/00; G16C 20/90; G06K 9/623; G06K 9/6256; G06K 9/6267; G06K 9/6262; G06K 9/6218; G06N 5/025; G06N 7/005; G06N 20/10; G06N 20/00; G06N 20/20; G06N 3/08; G06N 3/0895; G06N 3/09; G06F 18/213; G06F 18/2148; G06F 18/2163; G06F 18/24155; G06F 18/2415; G06F 17/10; G06F 17/16; G06F 17/18; G06F 17/14; G06F 17/11; G06F 18/2135

See application file for complete search history.

(56) References Cited

U.S. PATENT DOCUMENTS 10,533,989 B2 * 1/2020 Kellum ................ G01N 33/521
2009/0155826 A1 6/2009 Hu et al.
2009/0269796 A1 * 10/2009 Gerszten ............ G01N 33/6893 435/29
2015/0241406 A1 * 8/2015 Reszka ..................... G16B 5/00 506/6
2016/0195547 A1 * 7/2016 Cohen ..................... G01N 33/50 506/9
2016/0209428 A1 * 7/2016 Naviaux ............... A61K 31/185
2019/0156919 A1 * 5/2019 Magis .................... G16B 40/00

FOREIGN PATENT DOCUMENTS

CN       106581014       * 11/2011
CN       102243216       *  4/2017
WO   WO-2015157407 A1 * 10/2015 ......... G01N 30/7206

OTHER PUBLICATIONS

Mayr, A. (2014) Boosting the Concordance index for survival data—a unified framework to derive and evaluate biomarker combinations. PLOS One vol. 9, Issue 1, 10pages. (Year: 2014).*
Rizza S. et al. (2014) Metabolomics signature improves the prediction of cardiovascular events in elderly subjects. Atherosclerosis vol. 232 p. 260-264. (Year: 2014).*
Swan, A.L. et al. (2013) Application of Machine Learning to Proteomics Data: Classification and Biomarker Identification in Postgenomics Biology. OMICS: a journal of integrative biology, vol. 17, No. 12 p. 595-616. (Year: 2013).*
Heinemann, J. et al. (2014) Application of support vector machines to metabolomics experiments with limited replicates. Metabolomics vol. 10:1121-1128. (Year: 2014).*
Langley, R. J. (2013) An Integrated Clinico-Metabolomic Model Improves Prediction of Death in Sepsis. Science of translational medicine, vol. 5, issue 195, e195ra95 (18 pages). (Year: 2013).*
Human Metabolome Database Record alpha lactose, from online database hmdb. downloaded Nov. 2021 (Year: 2021).*
Human Metabolome Database Record methylcysteine, from online hmbd. downloaded Nov. 2021 (Year: 2021).*
Human Metabolome Database Record 2-aminoisobutyric acid, from online hmbd. downloaded Nov. 2021 (Year: 2021).*
Human Metabolome Database Record D-glucuronic acid, from online hmbd. downloaded Nov. 2021 (Year: 2021).*
Backlin, C., "Machine Learning Based Analysis of DNA Methylation Patterns in Pediatric Leukemia," Thesis, Digital Comprehensive Summaries of Uppsala Dissertations from the Faculty of Medicine, 1069, Uppsala Universitet, 2015. 70 pages.
Chen, B.H. et al., DNA Methylation-Based Measures of Biological Age: Meta-Analysis Predicting Time to Death, Aging, Sep. 2016, pp. 1844-1859, vol. 8, No. 9.
Dawber, T.R. et al., "Epidemiological Approaches to Heart Disease: The Framingham Study," Joint Session of the Epidemiology Health Officers, Medical Care, and Statistics Sections of the American Public Health Association, Seventy-eighth Annual Meeting, Nov. 3, 1950, pp. 279-286.
Horvath, S., "DNA Methylation Age of Human Tissues and Cell Types," Genome Biol., 2013, vol. 14, No. 10.

(Continued)

*Primary Examiner* — Mary K Zeman
(74) *Attorney, Agent, or Firm* — Fenwick & West LLP

(57) ABSTRACT

In various embodiments, the present description relates to the use of factors related to survival. The methods, compositions and systems described herein may be used to determine factors affecting survival, assess survival risk based on factors related to survival and/or make suggestions to increase the likelihood of survival longer than otherwise predicted.

18 Claims, 4 Drawing Sheets

(56) References Cited

OTHER PUBLICATIONS

Leisalu, L. et al., "Cohort Profile: Estonian Biobank of the Estonian Genome Center, University of Tartu," International Journal of Epidemiology, 2015, pp. 1137-1147.

Levine, M.E. et al., "DNA Methylation Age of Blood Predicts Future Onset of Lung Cancer in the Women's Health Initiative," Aging, Sep. 2015, pp. 690-700, vol. 7, No. 9.

Lossos, I.S. et al., "Prediction of Survival in Diffuse Large-B-Cell Lymphoma Based on the Expression of Six Genes," The New England Journal of Medicine, Apr. 29, 2004, pp. 1828-1837, vol. 350.

"Package 'glmnet," Apr. 2, 2018, 23 pages.

Pölsterl, S. et al., "Fast Training of Support Vector Machines for Survival Analysis," Machine Learning and Knowledge Discovery in Databases, ECML PKDD 2015, Part II, LNAI 9285, 2015, Appice et al. (Eds.), pp. 243-259.

Ridgeway, G., "Generalized Boosted Models: A Guide to the GBM Package," Aug. 3, 2007, 12 pages.

Simon, N., Friedman, J., Hastie, T., Tibshirani, R. (2011) Regularization Paths for Cox's Proportional Hazards Model via Coordinate Descent, Journal of Statistical Software, vol. 39(5) 1-13.

Spector, T. et al., "The UK Adult Twins Registry (TwinsUK)" Twin Research and Human Genetics, 2006, vol. 9, No. 6.

Van De Vijver, M.J., "A Gene-Expression Signature as a Predictor of Survival in Breast Cancer," The New England Journal of Medicine, Dec. 19, 2002, pp. 1999-2009, vol. 347.

Zhang, Y. et al., "DNA Methylation Signatures in Peripheral Blood Strongly Predict All-Cause Mortality," Nature Communications, Mar. 17, 2017, pp. 1-11.

\* cited by examiner

SURVIVAL PREDICTION USING METABOLOMIC PROFILES

CROSS REFERENCE TO RELATED APPLICATIONS

This application claims benefit to U.S. provisional application No. 62/572,378 filed Oct. 13, 2017 and U.S. provisional application No. 62/460,648 filed Feb. 17, 2017 each of which is hereby incorporated in its entirety by reference.

BACKGROUND

Predicting mortality, i.e. an individual's risk of death, and predicting related outcomes such as an individual's future risk of developing an age-related disease, remains very challenging. Human aging is complex and multiple factors play a role, including genetic and environmental factors that are integrated together in the metabolome. Predictive biomarkers of mortality are of substantial clinical and scientific interest. They can be applied to help doctors identify and treat populations at increased risk of dying, and to assess human frailty, pace of aging, and the effects of new therapies. Thus, there is a need to identify and use proxies for mortality and survival in many important applications. Specifically, there is a need to find metabolic factors that correlate with survival and/or mortality. There is a further need to have suitable methods to study survival and the effect of various factors on survival in shorter time periods. Also, there is a need to identify drugs and life-style choices that have a positive or negative effect on factors that correlate with survival and/or with mortality. Such drugs may be used to increase survival. The methods and systems described herein, in various embodiments, address these needs in novel and effective ways.

SUMMARY

In a first aspect, the methods, compositions and systems described herein relate to a method for determining a survival metric for a subject. The method may comprise obtaining a dataset associated with a sample from the subject comprising data representing presence or abundance of at least n survival biomarkers and generating, a survival metric value. The method may further comprise performing or having performed at least one survival biomarker detection assay. In some embodiments, the survival metric value is indicative of the subject's relative survival risk. In some embodiments, the survival metric value is indicative of the subject's relative likelihood of contracting an aging-related disease, chance of survival, or chance of death. In some embodiments, the relative survival risk is assessed with respect to a default state and the subject differs from the default state in the metabolic presence or amount of one or more compounds in the sample. In some embodiments, the method further comprises obtaining data representing at least one aging indicator from the subject. In some embodiments, the subject differs from the default state in the values of one or more aging indicators. In some embodiments, the aging indicators are selected from the list consisting of age, sex, race, ethnicity, smoking status, alcohol consumption status, diastolic blood pressure, systolic blood pressure, a family history parameter, a medical history parameter, a medical symptom parameter, height, weight, a body-mass index, and resting heart rate of a subject. In some embodiments, the method further comprises mathematically combining the value(s) for the at least one aging indicator with the value(s) for the n survival biomarkers, thereby generating the survival score. In some embodiments, the n survival biomarkers are selected from a list generated by obtaining a metabolite dataset associated with a sample from one or more subjects in a study group comprising data representing presence or abundance of at least m metabolites; obtaining a clinical factor dataset from the one or more subjects in a study group comprising data representing the value of at least 1 aging indicators; determining a list of k significant metabolites, wherein each significant metabolites significantly associates with one or more aging indicators of the at least 1 aging indicators; and selecting n metabolites from the list of significant metabolites as survival biomarkers. In some embodiments, the n survival biomarkers are selected from a list generated by obtaining a metabolite dataset associated with a sample from one or more subjects in a study group comprising data representing presence or abundance of at least m metabolites; obtaining a clinical factor dataset from the one or more subjects in a study group comprising data representing the value of at least 1 aging indicators; determining a list of k significant metabolites, wherein each significant metabolites significantly associates with all-cause mortality; and selecting n metabolites from the list of significant metabolites as survival biomarkers. In some embodiments, the n survival biomarkers are selected from a list consisting of the biomarkers having the m/z ratios listed in Table 1. In some embodiments, the n survival biomarkers are selected from a list consisting of the biomarkers having the m/z ratios listed in Table 2. In some embodiments, the n survival biomarkers are selected from a list consisting of the biomarkers having the m/z ratios listed in Table 3. In some embodiments, the n survival biomarkers are selected from a list consisting of the biomarkers having the m/z ratios listed in Table 4. In some embodiments, the n survival biomarkers are selected from a list consisting of the biomarkers having the m/z ratios listed in Table 5. In some embodiments, the n survival biomarkers are selected from a list consisting of the biomarkers having the m/z ratios listed in two or more of Table 1, Table 2, Table 3, Table 4, and Table 5. In some embodiments, selecting n metabolites comprises a random selection method. In some embodiments, determining a list of significant metabolites and selecting n metabolites comprise picking metabolites by metabolite identity or metabolite feature. In some embodiments, n is between 2 and 661, inclusive. In some embodiments, n is at least 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, is at least 10, 20, 30, 50, 100, 250, 500, 1000, 2000, 3000, 5000, or 10000. In some embodiments, k is at least 2, 3, 4, 5, 6, 7, 8, 9, 10, 11, 12, 13, 14, 15, 16, 17, 18, 19, 20, 50, 100, 150, 200, 250, 300, 400, 500, or 600. In some embodiments, wherein n is equal to k. In some embodiments, 1 is at least 2, 3, 4, 5, 6, 7, 8, 9, 10, 11, 12, 13, 14, 15, 16, 17, 18, 19, or 20. In some embodiments, a unit change in the value of at least one significant metabolite has an impact on the value of relative survival risk of higher than or equal to 1.001, 1.01, 1.015, 1.05, 1.1. 1.15, 1.2, 1,25, 1.3, 1.35, 1.4, 1.45, 1.5, 1.6, 1.7, 1.8, 1.9, 2.0, 2.1, 2.2, 2.13, 2.14, 2.3 2.4, 2.5, 2.55, 2.6, 2.7, 2.8, 2.9, 3.0, 3.1, 3.2, 3.3, 3.4, 3.5, 3.6, 3.7, 3.8, 3.9, 4.0, 4.1, 4.2, or 4.3 fold and the value of unit change is determined by a normalized distribution of each significant metabolite's values within the metabolite dataset. In some embodiments, a unit change in the value of each significant metabolite has an impact on the value of relative survival risk of higher than or equal to 1.001, 1.01, 1.015, 1.05, 1.1. 1.15, 1.2, 1.25, 1.3, 1.35, 1.4, 1.45, 1.5, 1.6, 1.7, 1.8, 1.9, 2.0, 2.1, 2.13, 2.14, 2.2, 2.3 2.4, 2.5, 2.55, 2.6, 2.7, 2.8, 2.9, 3.0, 3.1, 3.2, 3.3, 3.4, 3.5, 3.6, 3.7, 3.8, 3.9, 4.0, 4.1, 4.2, or 4.3 fold and the value of unit change is determined by a normalized distribution of each significant metabolite's values within the metabolite dataset. In some embodiments, a unit change in the value of at least one significant metabolite has an impact on the value of relative survival risk of lower than or equal to 0.999, 0.995, 0.99, 0.95, 0.90, 0.87, 0.85, 0.8, 0.75, 0.7, 0.65, 0.63, 0.60, 0.58, 0.56, 0.5, 0.53, 0.52, 0.5, 0.49, 0.48, 0.47, 0.46, 0.45, 0.44, 0.43, 0.42, 0.41, 0.4, 0.39, 0.38, 0.37, 0.36, 0.35, 0.34, 0.33, 0.32, 0.31, 0.3, 0.29, 0.28, 0.27, 0.26, 0.25, 0.24, or 0.23 fold and wherein the value of unit change is determined by a normalized distribution of each significant metabolite's values within the metabolite dataset. In some embodiments, a unit change in the value of each significant metabolite has an impact on the value of relative survival risk of lower than or equal to 0.999, 0.995, 0.99, 0.95, 0.90, 0.87, 0.85, 0.8, 0.75, 0.7, 0.65, 0.63, 0.60, 0.58, 0.56, 0.5, 0.53, 0.52, 0.5, 0.49, 0.48, 0.47, 0.46, 0.45, 0.44, 0.43, 0.42, 0.41, 0.4, 0.39, 0.38, 0.37, 0.36, 0.35, 0.34, 0.33, 0.32, 0.31, 0.3, 0.29, 0.28, 0.27, 0.26, 0.25, 0.24, or 0.23 fold and the value of unit change is determined by a normalized distribution of each significant metabolite's values within the metabolite dataset. In some embodiments, a unit change in the value of all n survival biomarkers together have an impact on the value of relative survival risk of higher than or equal to 1.01, 1.05, 1.1, 1.15, 1.2, 1.3, 1.4, 1.5, 1.6, 1.7, 1.8, 1.9, 2.0, 2.1, 2.2, 2.3 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, or 4.3 fold or more and the value of unit change is determined by a normalized distribution of each survival biomarker's values within the metabolite dataset. In some embodiments, a unit change in the value of all n survival biomarkers together have an impact on the value of relative survival risk of lower than or equal to 0.99, 0.95, 0.90, 0.87, 0.85, 0.8, 0.75, 0.7, 0.65, 0.60, 0.58, 0.5, 0.53, 0.52, 0.5, 0.49, 0.48, 0.47, 0.46, 0.45, 0.44, 0.43, 0.42, 0.41, 0.4, 0.39, 0.38, 0.37, 0.36, 0.35, 0.34, 0.33, 0.32, 0.31, 0.3, 0.29, 0.28, 0.27, 0.26, 0.25, 0.24, 0.23 fold or less and the value of unit change is determined by a normalized distribution of each survival biomarker's values within the metabolite dataset. In some embodiments, the survival metric value is generated by a survival predictor model. In some embodiments, the survival predictor model has been built using j biomarkers that, when tested against a dataset of at least 500 subjects, associate with all-cause mortality with a p-value of less than a threshold. In some embodiments, j is greater than or equal to n. In some embodiments, the threshold is set to be 0.2, 0.1, 0.05, 0.04, 0.03, 0.025, 0.01, 0.005, 0.0025, 0.001, 0.0005, 0.00025, 0.0001, 0.00005, 0.000025, 0.00001 or less. In some embodiments, j is at least 2, 3, 4, 5, 6, 7, 8, 9, 10, 11, 12, 13, 14, 15, 16, 17, 18, 19, 20, 25, or 30. In some embodiments, the survival predictor model's performance is characterized by Harrell's concordance index and wherein the Harrell's concordance index is at least 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99, for example for a dataset of at least 500 subjects. In some embodiments, the dataset of at least 500 subject comprises the study cohort described in Example 1. In some embodiments, the dataset of at least 500 subject consists of the study cohort described in Example 1. In some embodiments, the false discovery rate (FDR) for each of the j metabolites is less than 40%, 35%, 30%, 25%, 20%, 15%, 10%, 5%, 2.5%, 1%, 0.5%, or less. In some embodiments, the survival biomarker detection assay comprises a biological sample that is collected from a single cell, multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, a bodily fluid, a swab, or an extract thereof. In some embodiments, the subject comprises a mammal. In some embodiments, the subject is selected from the group consisting of a rat, a mouse, a monkey, a rabbit, a pig, and a human. In some embodiments, the data representing presence or abundance of at least n survival biomarkers comprises normalized metabolite values. In some embodiments, the cross-validated hazard ratio (HR) of the survival predictor model is greater than 1.1, 1.2, 1.3, 1.4, 1.5, 1.6, 1.7, 1.8, 1.9, 2, 2.02, 2.05, 2.1, 2.16, 2.2, 2.3, 2.4, 2.5, 2.6, 2.69, 2.7, 2.8, 2.9, 3, 3.1, 3.2, 3.3, 3.4, 3.5, 3.6, 3.7, 3.8, 3.9, 4, 4.1, 4.2, 4.3, 4.4, or higher. In some embodiments, the cross-validated hazard ratio (HR) of the survival predictor model is higher than any non-metabolite survival predictor model not comprising the use of metabolite biomarkers, wherein the non-metabolite survival predictor model is trained on the same dataset. In some embodiments, the n survival biomarkers comprise the biomarkers in Table 3. In some embodiments, the n survival biomarkers comprise the biomarkers in Table 4. In some embodiments, the n survival biomarkers comprise the biomarkers in Table 5. In some embodiments, the survival predictor comprises a Cox proportional hazards model.

In a second aspect, the methods, compositions and systems described herein relate to a computer module comprising a survival predictor model, wherein the survival predictor model is generated by a) obtaining a metabolite dataset associated with a sample from one or more subjects in a study group comprising data representing presence or abundance of at least m metabolites; b) obtaining a clinical factor dataset from the one or more subjects in a study group comprising data representing the value of at least 1 aging indicators; c) determining a list of k significant metabolites, wherein each significant metabolites significantly associates with all-cause mortality; and d) selecting n metabolites from the list of significant metabolites as survival biomarkers; wherein the survival predictor model generates a survival metric that is dependent on the value of the n survival biomarkers. In some embodiments, the survival predictor comprises a Cox proportional hazards model.

In a third aspect, the methods, compositions and systems described herein relate to a method of drug screening, the method comprising a) contacting one or more biological samples with a test compound; b) obtaining a metabolite dataset associated with the one or more biological samples representing presence or abundance of at least m metabolites in the one or more biological samples; c) calculating a survival metric that is dependent on the metabolite dataset; and d) designating the test compound as an anti-aging drug candidate, if the survival metric falls within a pre-designated range. In some embodiments, the method further comprises testing the anti-aging drug candidate in additional essays indicative of survival risk.

In a fourth aspect, the methods, compositions and systems described herein relate to a system for determining aging related disease risk in a subject, comprising: a) a storage memory for storing a dataset associated with a sample from the subject comprising metabolite values representing presence or abundance of one or more metabolites corresponding to at least two biomarkers selected from the list consisting of the metabolites in Table 1 and Table 2; and b) a processor communicatively coupled to the storage memory for generating a survival metric by mathematically combining the metabolite values, wherein a generated survival metric value that is greater than 1 indicates a decreased relative survival risk. In various embodiments, the sample comprises metabolites from a single cell, multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, a bodily fluid, or a swab of the subject or extracts thereof. In various embodiments, the survival metric value is generated by a survival predictor model and wherein the survival predictor model was generated using one or more of a partial least squares model, a logistic regression model, a linear regression model, a linear discriminant analysis model, a ridge regression model, a tree-based recursive partitioning model, a Cox proportional hazard model, an accelerated failure time model, a Weibull model, an exponential model, a Standard Gamma model, a log-normal model, a Generalized Gamma model, a log-logistic model, a Gompertz model, a frailty model, a ridge regression model, an elastic net regression model, a support network machine, a tree-based model, a tree-based recursive partitioning model, a regression tree, and a classification tree. In various embodiments, the subject is a human. In various embodiments, the system further comprises an apparatus for providing a readout that provides instructions for taking at least one action based on the survival metric. In some embodiments, the at least one action comprises treating the subject, advising lifestyle changes to the subject, performing a procedure on the subject, performing further diagnostics on the subject, assessing the subject's health further, or optimizing medical therapy. In some embodiments, the survival predictor model comprises a Cox proportional hazards model.

In a fifth aspect, the methods, compositions and systems described herein relate to a computer-readable storage medium storing computer-executable program code for determining a survival metric for a subject, comprising: a) program code for storing a dataset associated with a sample from the subject comprising metabolite values representing presence or abundance of one or more metabolites corresponding to at least two biomarkers selected from the list consisting of the metabolites in Table 1 and Table 2; and b) program code for generating a survival metric by mathematically combining the metabolite values, wherein a generated survival metric value that is greater than 1 indicates a decreased relative survival risk. In some embodiments, the computer-readable storage medium further comprises program code for storing instructions for taking at least one action based on the score. In some embodiments, the at least one action comprises treating the subject, advising lifestyle changes to the subject, performing a procedure on the subject, performing further diagnostics on the subject, assessing the subject's health further, or optimizing medical therapy.

In a sixth aspect, the methods, compositions and systems described herein relate to a kit for determining survival risk in a subject, comprising: a set of reagents for generating via at least one assay a dataset associated with a sample from the subject comprising metabolite values representing presence or abundance of one or more metabolites corresponding to at least two survival biomarkers selected from the list consisting of the metabolites in Table 1 and Table 2.

In certain embodiments of the methods described herein, the at least one of the survival biomarkers is glucuronate. In certain embodiments, the at least one of the survival biomarkers is citrate. In certain embodiments, the at least one of the survival biomarkers is adipic acid. In certain embodiments, the at least one of the survival biomarkers is isocitrate. In certain embodiments, the at least one of the survival biomarkers is lactate. In certain embodiments, the survival biomarkers comprises at least one subclass of lipids. In certain embodiments, the subclass of lipids comprises monoacylglycerols (MAG), diacylglycerols (DAG), triacylglycerols (TAG), phosphatidylethanolamine (PE), phsphatidylcholine (PC), phosphatidyl inositol (PI), phosphatidylserine (PS), ceramide (CE), 3,4,5-phosphorylated inositol lipids ($PIP_3$), 4,5-phosphorylated inositol lipids ($PIP_2$), plasmalogens or combinations thereof. In certain embodiments, the subclass of lipids is selected from the group consisting of: monoacylglycerols (MAG), diacylglycerols (DAG), triacylglycerols (TAG), phosphatidylethanolamine (PE), phsphatidylcholine (PC), phosphatidyl inositol (PI), phosphatidylserine (PS), ceramide (CE), 3,4,5-phosphorylated inositol lipids ($PIP_3$), 4,5-phosphorylated inositol lipids ($PIP_2$), plasmalogens and combinations thereof. In certain embodiments, the subclass of lipids is plasmalogens. In certain embodiments, the at least one of the survival biomarkers is a lipid listed in Table 9 and combinations thereof. In certain embodiments, the methods described herein further comprise administering a prophylactic regimen to prevent the onset or severity of the aging-related disease.

In an aspect, described herein is a method for determining a survival metric for a subject, comprising obtaining a dataset associated with a sample from the subject comprising data representing presence or abundance of an individual survival biomarker; inputting the dataset into a survival predictor model comprising coefficients for the survival biomarkers to generate a survival metric value; and providing the survival metric value. In an embodiment, the method further comprises performing or having performed a survival biomarker detection assay. In an embodiment, the survival metric value is indicative of the subject's relative survival risk. In an embodiment, the survival metric value is indicative of the subject's relative likelihood of contracting an aging-related disease, chance of survival, or chance of death. In an embodiment, the relative survival risk is assessed with respect to a default state and the subject differs from the default state in the metabolic presence or amount of one or more compounds in the sample. In an embodiment, the methods further comprise obtaining data representing at least one aging indicator from the subject. In an embodiment, the subject differs from the default state in the values of one or more aging indicators. In an embodiment, the aging indicators are selected from the list consisting of age, sex, race, ethnicity, smoking status, alcohol consumption status, diastolic blood pressure, systolic blood pressure, a family history parameter, a medical history parameter, a medical symptom parameter, height, weight, a body-mass index, and resting heart rate of a subject. In an embodiment, the method further comprises mathematically combining the value(s) for the at least one aging indicator with the metabolite value for the survival biomarker to generate the survival score. In an embodiment, the survival biomarker is selected from a list generated by obtaining a metabolite dataset associated with a sample from one or more subjects in a study group comprising data representing presence or abundance of at least m metabolites; obtaining a clinical factor dataset from the one or more subjects in a study group comprising data representing the value of at least 1 aging indicators; determining a list of k significant metabolites, wherein each significant metabolites significantly associates with one or more aging indicators of the at least 1 aging indicators; and selecting an individual metabolite from the list of significant metabolites as survival biomarkers. In certain embodiments, the survival biomarker is selected from a list generated by obtaining a metabolite dataset associated with a sample from one or more subjects in a study group comprising data representing presence or abundance of at least m metabolites; obtaining a clinical factor dataset from the one or more subjects in a study group comprising data representing the value of at least 1 aging indicators; determining a list of k significant metabolites, wherein each significant metabolites significantly associates with all-cause mortality; and selecting an individual metabolite from the list of significant metabolites as survival biomarkers. In certain embodiments, the survival biomarker detection assay comprises use of a biological sample that is collected from a single cell, multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, a bodily fluid, a swab, or an extract thereof. In an embodiment, the subject comprises a mammal. In certain embodiments, the subject is selected from the group consisting of a rat, a mouse, a monkey, a rabbit, a pig, and a human. In an embodiment, the subject is a human. In certain embodiments, the data representing presence or abundance of the individual survival biomarker comprises normalized metabolite values. In an embodiment, the cross-validated hazard ratio (HR) of the survival predictor model is greater than 1.1, 1.2, 1.3, 1.4, 1.5, 1.6, 1.7, 1.8, 1.9, 2, 2.02, 2.05, 2.1, 2.16, 2.2, 2.3, 2.4, 2.5, 2.6, 2.69, 2.7, 2.8, 2.9, 3, 3.1, 3.2, 3.3, 3.4, 3.5, 3.6, 3.7, 3.8, 3.9, 4, 4.1, 4.2, 4.3, or 4.4. In an embodiment, the survival predictor model comprises a Cox proportional hazards model. In an embodiment, the survival biomarker is glucuronate. In an embodiment, the survival biomarker is citrate. In an embodiment, the survival biomarker is adipic acid. In an embodiment, the survival biomarker is isocitrate. In an embodiment, the survival biomarker is lactate. In certain embodiments, the survival metric value is indicative of a subject's relative survival risk over a period of time. In an embodiment, the period of time is 17 years or less. In an embodiment, the period of time is 11 years or less.

In certain aspect, described herein are methods of diagnosing a subject's relative likelihood of contracting an aging-related disease, chance of survival, or chance of death; wherein the method comprises performing a survival biomarker detection assay to detect the presence or abundance of at least one survival biomarker in a sample obtained from the subject; generating a survival metric for a subject; and administering a prophylactic regimen to prevent the onset or severity of the aging-related disease. In an embodiment, the survival biomarker detection assay comprises performing mass spectrometry. In an embodiment, the subject is suspected of having a relatively high likelihood of contracting an aging-related disease. In an embodiment, the subject has a family history of an aging-related disease. In an embodiment, the at least one survival biomarkers is glucuronate. In an embodiment, the at least one survival biomarkers is citrate. In an embodiment, the at least one survival biomarkers is adipic acid. In an embodiment, the at least one survival biomarkers is isocitrate. In an embodiment, the at least one survival biomarkers is lactate. In an embodiment, the survival biomarkers comprises a subclass of lipids. In certain embodiments, the subclass of lipids comprises monoacylglycerols (MAG), diacylglycerols (DAG), triacylglycerols (TAG), phosphatidylethanolamine (PE), phsphatidylcholine (PC), phosphatidyl inositol (PI), phosphatidylserine (PS), ceramide (CE), 3,4,5-phosphorylated inositol lipids ($PIP_3$), 4,5-phosphorylated inositol lipids ($PIP_2$), plasmalogens or combinations thereof. In certain embodiments, the subclass of lipids is selected from the group consisting of: monoacylglycerols (MAG), diacylglycerols (DAG), triacylglycerols (TAG), phosphatidylethanolamine (PE), phsphatidylcholine (PC), phosphatidyl inositol (PI), phosphatidylserine (PS), ceramide (CE), 3,4,5-phosphorylated inositol lipids ($PIP_3$), 4,5-phosphorylated inositol lipids ($PIP_2$), plasmalogens and combinations thereof. In an embodiment, the subclass of lipids is plasmalogens. In certain embodiments, the at least one survival biomarkers is a lipid listed in Table 9 and combinations thereof. In certain embodiments, the method comprises detection of the presence or abundance of a plurality of survival biomarkers.

In certain embodiments, the methods described herein further comprise generating a life insurance policy for each of the subjects based on the survival metric.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

DETAILED DESCRIPTION OF THE PREFERRED EMBODIMENTS

Advantages and Utility

Figure 1:
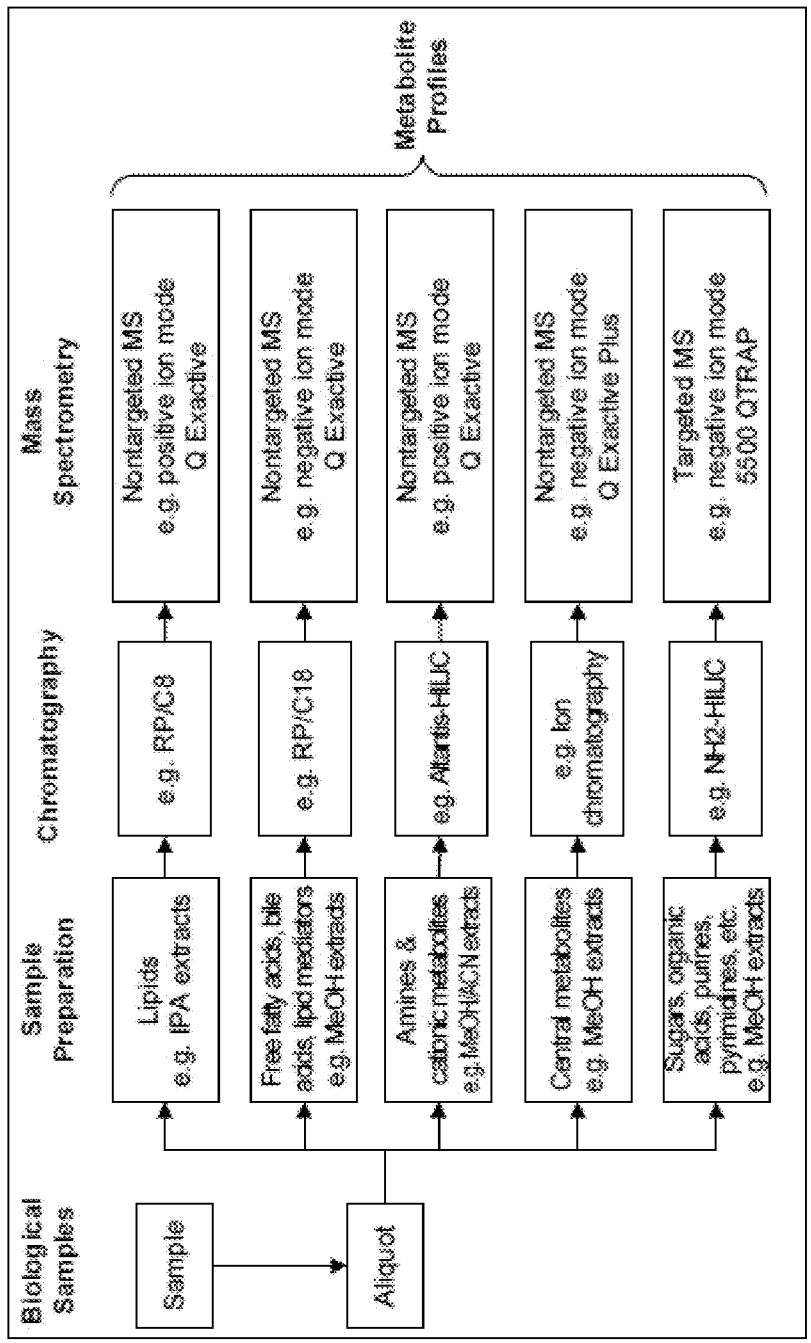
FIG. 1 depicts an exemplary illustration of a metabolomics study where metabolites can be tracked in samples from one or more subjects.

This description, in various embodiments, relate to identification of metabolic features and/or metabolite identities that correlate with all-cause mortality. Methods described herein allow for the selection of those biomarkers. Survival biomarkers may be used to build survival predictor models capable of determining the value for a survival metric given information regarding the abundance or presence (or absence) of those biomarkers in an individual, for example in a sample obtained from an individual. Survival metrics are used to predict survival related values, such as time to an aging event. An aging event may comprise the occurrence of an aging related condition, such as death or contraction of an aging related disease, including, without limitation, cardiovascular disease, angina, myocardial infarction, stroke, heart failure, hypertensive heart disease, hypertension, cardiomyopathy, heart arrhythmia, valvular heart disease, aortic aneurysms, peripheral artery disease, venous thrombosis, atherosclerosis, coronary artery disease, cancer, Type 1 diabetes, Type 2 diabetes, chronic obstructive pulmonary disease ("COPD"), stroke, arthritis, cataracts, macular degeneration, osteoporosis, fibrotic diseases, sarcopenia, osteoporosis, cognitive decline, dementia and/or Alzheimer's. Survival related values may be predicted in an absolute or relative fashion. This description also relates to determining the relative effect of a factor, such as, without limitation, a drug or a lifestyle choice, on a survival related value.

The principles described herein are useful for determining a survival metric for a subject from an analysis of a biological sample. The methods and compositions described herein may rely on one or more survival biomarker detection assays to analyze biological sample to identify information that can be used in determining the survival metric. The principles described herein are further useful for determining survival biomarkers and/or building survival predictor models that rely on those identified survival biomarkers for the prediction of the survival metric. Survival predictor models may be built with any plurality of biomarkers identified herein, in particular in Tables 1-10. The principles described herein are further useful for identifying drugs or life-style changes that have an effect on survival biomarkers and/or a survival metric predicted according to the methods and compositions described herein.

In addition to methods and compositions, embodiments include using a processor in conjunction with a non-transitory computer readable storage medium to create, store, process, access, and otherwise use data, models, and other computer instructions related to survival biomarkers or survival predictor models.

Definitions

Terms used in the claims and specification are defined as set forth below unless otherwise specified.

The term "ameliorating" refers to any therapeutically beneficial result in the treatment of a disease state, in extending life expectancy, or in decreasing the effect of a factor in all-cause mortality, e.g., an aging related disease state, including prophylaxis, lessening in the severity or progression, remission, or cure thereof.

The term "sufficient amount" means an amount sufficient to produce a desired effect, e.g., an amount sufficient to modulate survival of a subject.

The term "therapeutically effective amount" is an amount that is effective to ameliorate a symptom of a disease, a cause of mortality, aging or an aging related disease or a factor that correlates with mortality, aging or aging related disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

A "subject" or an "individual" in the context of the present teachings is generally an animal, e.g., a mammal. The subject can be a human patient, e.g., a human having an increased risk of mortality. The term "mammal" as used herein includes but is not limited to a human, non-human primate, canine, feline, murine, bovine, equine, and porcine.

Mammals other than humans can be advantageously used as subjects that represent animal models of, e.g., aging. A subject can be male or female. A subject can be one who has been previously diagnosed or identified as having an aging related disease. A subject can be one who has already undergone, or is undergoing, a therapeutic intervention for aging related disease. A subject can also be one who has not been previously diagnosed as having aging related disease; e.g., a subject can be one who exhibits one or more symptoms or risk factors for aging related disease, or a subject who does not exhibit symptoms or risk factors for aging related disease, or a subject who is asymptomatic for aging related disease.

A "sample" in the context of the present teachings refers to any biological sample that is isolated from a subject. A sample may comprise a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof. "Blood sample" can refer to whole blood or any fraction thereof, including blood cells, red blood cells, white blood cells or leucocytes, platelets, serum and plasma. Samples can be obtained from a subject by any suitable method, including but not limited to venipuncture, excretion, ejaculation, massage, biopsy, needle aspirate, lavage, scraping, surgical incision, or intervention or any other suitable method known in the art. In one embodiment the sample is a whole blood sample. A sample can include protein extracted from blood of a subject.

To "analyze" includes measurement and/or detection of data associated with a metabolite or biomarker (such as, e.g., presence or absence of a metabolite feature or metabolite) in the sample (or, e.g., by obtaining a dataset reporting such measurements, as described in further detail elsewhere herein). In some aspects, an analysis can include comparing the measurement and/or detection against a measurement and/or detection in a sample or set of samples from the same subject or other control subject(s). The metabolite features and metabolite identities of the present teachings can be analyzed by any of the various conventional methods known in the art.

Metabolite features may be used to track uncharacterized metabolites. A feature can be a collection of data points, e.g. a region in a mass spectrum and time. For example, a combination of mass measurements and LC retention time may be used to define chromatographic/ion features (m z, RT). These may be used as a substitute for a molecular identifier. Higher specificity features may be obtained through the addition of fragmentation data (m z parent, RT, m z daughters). In some cases, untargeted profiling experiments may utilize preferred or target lists to track, select, and/or relate to known compounds metabolite features of interest. Metabolite features may be obtained through standardized metabolomics methods and metabolomics data reporting. Metabolite features may also be linked to metabolite databases, e.g., METLIN (metlin.scripps.edu), KEGG (www.genome.ad.jp/kegg), MetaCyc (MetaCyc.org), HumanCyc (humancyc.org), the Golm Metabolome Database (http://gmd.mpimp-golm.mpg.de), HMDB (hmdb.ca), BMRB (bmrb.wisc.edu/metabolomics), mzCloud (www.mzcloud.org), LIPIDMAPS (lipidmaps.org), and MassBank (www.massbank.jp), BiGG (bigg.ucsd.edu), MetaboLights (www.ebi.ac.uk/metabolights), Reactome (reactome.org), or WikiPathways (wikipathways.org), to facilitate identification.

A "dataset" is a set of data (e.g., numerical values) resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" comprises obtaining a set of data determined from at least one sample. Obtaining a dataset may comprise obtaining a sample, and/or processing the sample to experimentally determine the data, e.g., via measuring, such as by mass spectrometry and/or computationally processing data that was measured from a sample. Obtaining a dataset associated with a sample may comprise receiving a set of data, e.g., from a third party that has processed the sample to experimentally determine the dataset. In some embodiments, obtaining a dataset associated with a sample comprises mining data from at least one database or at least one publication or a combination of at least one database and at least one publication.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control.

The term "FDR" means false discovery rate. FDR may be estimated by analyzing randomly-permuted datasets and tabulating the average number of metabolites at a given p-value threshold.

The term "subclass of lipids" refers to a plurality of lipid metabolites that are commonly grouped by chemical structure by those of skill in the art including, but not limited to, saturated and unsaturated fatty acid ester derivatives, which may or may not include a glycerol moiety. Specific examples of a lipid subclasses includes, but is not limited to: monoacylglycerols (MAG), diacylglycerols (DAG), triacylglycerols (TAG), phosphatidylethanolamine (PE), phsphatidylcholine (PC), phosphatidyl inositol (PI), phosphatidylserine (PS), ceramide (CE), 3,4,5-phosphorylated inositol lipids ($PIP_3$), 4,5-phosphorylated inositol lipids ($PIP_2$) and plasmalogens. Lipid subclasses can also comprise adducts of individual lipids. In certain embodiments, a subclass of lipids may be a subset of a subclass that is commonly grouped by chemical structure by those of skill in the art.

This description generally relates to identification of metabolic features and/or metabolite identities that correlate with all-cause mortality. Such metabolic features and/or metabolite identities may be determined by use of metabolomics analysis. Metabolomics analysis, in various embodiments, comprises detection of changes in presence or abundance of metabolites in subjects or groups of subjects that have differing survival periods, survival expectancies, and/or risk of death.

This description also relates to building of survival predictor models that output a survival metric. Such survival metrics may relate to survival related observables, such as survival expectancy and/or risk of death. In various embodiments, survival predictor models may be built by selecting metabolite features and/or metabolite identities that strongly associate with survival periods ("survival biomarkers") or other observables that relate to survival periods ("aging indicator"). Such aging indicators may comprise variables that correlate with all-cause mortality, such as certain clinical factors. In some embodiments, survival predictor models utilize one or a plurality of survival biomarkers together with one or more aging indicators to generate a survival metric.

Survival biomarkers may be selected by conducting a cohort study. The cohort study may be designed such that certain variables that strongly correlate with survival are absent from the study. For example, individuals with major age-related diseases, such as, without limitation, hypertensive heart disease, Type 2 diabetes, coronary artery disease, cancer, Type 1 diabetes, chronic obstructive pulmonary disease (COPD), history with stroke, and/or Alzheimer's, at the time of sample collection may be excluded from the study cohort. A range of data about the cohort subjects, such as, without limitation, information from their health history, such as age, gender, smoking status, alcohol consumption status, height, weight, BMI, and blood pressure metrics, may be used as aging indicators to build a survival predictor model and/or to select survival biomarkers. In various embodiments, a list of survival biomarkers is prepared by correlation with aging indicators and/or with survival.

Metabolomic Profiles

Metabolite features and/or identities may be determined using metabolomics profiling. Metabolomic profiling may comprise characterization and/or measurement of metabolites, such as small molecule metabolites, in a biological sample, according the methods and compositions described herein in various embodiments. Biological samples may include, without limitation, a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof.

A metabolite profile may include information such as the quantity and/or type of metabolites present in a sample. Metabolite profiles may vary in complexity and information content. In some embodiments, a metabolite profile can be determined using a single technique. In other cases, several different techniques may be used in combination to generate a metabolite profile.

The complexity and information content of a metabolite profile can be chosen to suit the intended use of the profile. For example, the complexity and information content may be chosen according to the disease state of the test individuals, the disease state to be predicted, the types of small molecules present in an assayed biological sample, such as, without limitation, a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof. The metabolite profile may comprise and/or be or have been created so as to give information about the presence and/or abundance of one or more metabolites or metabolite classes and/or to give information about the absolute or relative distribution of metabolites or metabolite classes. For example, the metabolite profile may comprise and/or be or have been created so as to give information about the pairwise ratios in the abundance of a plurality of metabolites or metabolite classes, for example, about or at least about 2, 3, 4, 5, 6, 7, 8, 9, 10, 12, 15, 20, 25, 30, 50, 75, 100 or more metabolites.

FIG. 1 illustrates an example for creation of metabolite profiles according to various embodiments. The creation of metabolic profiles may start with biological sample collection. Sample collection may take place immediately before subsequent analysis steps. In some embodiments, samples are collected over time. One or more samples may be collected from each individual. The samples collected from some or all of the individuals in a group of individuals may be collected as a time series to create longitudinal data about a subset or all of the individuals in the group. The time series may be set so as to start at a certain start time and comprise periodic intervals. The periodic intervals may be linear, semi-linear, comprise decreasing or increasing interval lengths, or be random. The start time may be set at a particular point in time, at a particular age, or be random for some or all of the individuals. About or at least about 1, 2, 3, 4, 5, 6, 7, 8, 9, 10, 12, 15, 20, 25, 30, 40, 50, 75, 100 or more samples may be collected from each individual. The biological sample may comprise any suitable sample type, such as, without limitation, a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof.

The analysis of the biological samples or specimens described herein may involve one or more analysis methods. In some embodiments, biological samples or specimens described herein may be split into aliquots. In various embodiments, a different analysis is performed on each aliquot or each of a subset of aliquots from a biological specimen or sample. The different analyses may be designed to target a subgroup of metabolites. For example, different chromatography set-ups may be used to target different metabolites or metabolite classes. For example, liquid chromatography columns suitable to adsorb and differentially elute metabolites may be utilized for different metabolites or metabolite classes. In some embodiments, a combination of liquid chromatography (LC) methods is used for complementary sets of metabolite classes, for example polar metabolites, such as organic acids, and non-polar lipids, such as triglycerides.

The metabolites that are separated and/or analyzed by LC, may be further analyzed using a suitable data analysis method, such as mass spectrometry (MS; in tandem: LC-MS). The MS data may be acquired using sensitive, high resolution mass spectrometers (e.g. Q Exactive, Thermo Scientific). In some embodiments, MS data acquisition comprises untargeted measurement of metabolites of known identity and/or heretofore unidentified metabolites in a set of data acquisition experiments.

Metabolite profiles may be generated by one or more suitable method, including, without limitation, Gas Chromatography (GC), Liquid Chromatography (LC), Mass Spectroscopy (MS), Chromatography-Flame Ionization Detection (GC-FID), Gas Chromatography-Thermal Conductivity Detection (GC-TCD), Gas Chromatography-Electron Capture Detection (GC-ECD), Gas Chromatography-Mass Spectrometry (GC-MS), Gas Chromatography-Tandem Mass Spectrometry (GC-MS/MS), Headspace Gas Chromatography (HS-GC), Thermal Desorption Gas Chromatography (TD-GC), Two Dimensional Gas Chromatography (2D GC, GC×GC), Pyrolysis Gas Chromatography, Solid Phase Microextraction-Gas Chromatography (SPME-GC), Headspace-Solid Phase Dynamic Extraction GC-MS (HS-SPDE-GC-MS), High Performance Liquid Chromatography-Ultraviolet and Visible Detection (HPLC-UV), High Performance Liquid Chromatography-Refractive Index Detection (HPLC-RI), High Performance Liquid Chromatography-Evaporative Laser Scattering Detection (HPLC-ELSD), High Performance Liquid Chromatography-Charged Aerosol Detection (HPLC-CAD), High Performance Liquid Chromatography-Photodiode Array Detection (HPLC-PDA), High Performance Liquid Chromatography-Fluorescence Detection (HPLC-FL), Reversed Phase Liquid Chromatography (RPLC), Normal Phase Liquid Chromatography (NPLC), Hydrophilic Interaction Liquid Chromatography (HILIC), Ion Exchange Chromatography (IEX), High Temperature Liquid Chromatography (HTLC), Flow Injection Analysis (FIA), Liquid Chromatography-Single Quadrupole Mass Spectrometry (LC-MS), Liquid Chromatography-Triple Quadrupole Tandem Mass Spectrometry (LC-MS/MS), Liquid Chromatography-Ion Trap Tandem Mass Spectrometry (LC-MS/MS), Liquid Chromatography-QToF Mass Spectrometry (LC-QTOF-MS), Liquid Chromatography-Orbitrap Mass Spectrometry (LC-Orbitrap-MS), Liquid Chromatography-Fourier Transform Ion Cyclotron Resonance Mass Spectrometry (LC-FTICR-MS), Two Dimensional Liquid Chromatography (2D LC, LC×LC), Supercritical Fluid Chromatography (SFC), Matrix Assisted Laser Desorption/Ionization-Mass Spectrometry (MALDI-MS), Surface Assisted Laser Desorption/Ionization-Mass Spectrometry (SALDI-MS), Desorption/Ionization on Silicon-Mass Spectrometry (DIOS-MS), Nanostructure Initiator Mass Spectrometry (NIMS), Microfluidic-Mass Spectrometry, Desorption Electrospray Ionization-Mass Spectrometry (ESI-MS), Electrospray Ionization-Mass Spectrometry (ESI-MS), Atmospheric Pressure Photoionization-Mass Spectrometry (APPI-MS), Atmospheric Pressure Chemical Ionization-Mass Spectrometry (APCI-MS), Electron Impact-Mass Spectrometry (EI-MS), Chemical Ionization-Mass Spectrometry (CI-MS), Nano Electrospray Ionization-Mass Spectrometry (nano-ESI-MS), Chip Nanoelectrospray Ionization-Mass Spectrometry (Chip nano-ESI-MS), Direct Infusion-Mass Spectrometry (DI-MS), Laser Ablation Electrospray Ionization-Mass Spectrometry (LAESI-MS), Direct Analysis in Real Time-Mass Spectrometry (DART-MS), Selected Ion Flow Tube-Mass Spectrometry (SIFT-MS), Tissue Spray Ionization-Mass Spectrometry (TSI-MS), Infrared Matrix Assisted Laser Desorption/Ionization-Mass Spectrometry (IR-MALDESI-MS), Nano-Desorption Electrospray Ionization-Mass Spectrometry (nano-DESI-MS), Droplet-liquid microjunction-surface sampling probe-Mass Spectrometry (droplet-LMJ-SSP-MS), Single Probe Mass Spectrometry (SP-MS), Traveling Wave Ion Mobility-Mass Spectrometry (TWIM-MS), Field Asymmetric Ion Mobility Spectrometry-Mass Spectrometry (FAIMS-MS), Drift Tube Ion Mobility Spectrometry-Mass Spectrometry (DTIMS-MS), Secondary Ion—Mass Spectrometry (SIMS), Chiral Chromatography, Thin Layer Chromatography (TLC), Thin Layer Chromatography-Densitometry, Thin Layer Chromatography-Immunodetection, High Performance Thin Layer Chromatography (HPTLC), Capillary Electrophoresis-Ultraviolet and Visible Detection (CE-UV), Capillary Electrophoresis-Mass Spectrometry (CE-MS), Capillary Electrophoresis-Tandem Mass Spectrometry (CE-MS/MS), Micellar Electrokinetic Chromatography (MEKC), Proton Nuclear Magnetic Resonance Spectroscopy (1H NMR), Carbon Nuclear Magnetic Resonance Spectroscopy (13C NMR), Two Dimensional Nuclear Magnetic Resonance Spectroscopy (2D NMR), 2D 1H J-Resolved NMR Spectroscopy (JRES), 2D 1H Chemical Shift Correlation NMR Spectroscopy (COSY), 2D 1H Total Correlation NMR Spectroscopy (TOCSY), 2D 13C, 1H Heteronuclear Multiple Bond Correlation NMR Spectroscopy (HMBC), Fourier Transform Infrared Spectroscopy (FTIR), Fourier Transform Attenuated Total Reflectance Spectroscopy (FT-ATR), Near Infrared Spectroscopy (NIR), Far Infrared Spectroscopy (Far IR), Mid IR Spectroscopy, Raman Spectroscopy, Ultraviolet and Visible Spectroscopy (UV-Vis), Fluorescence Spectroscopy, X-ray Fluorescence Spectroscopy (XRF), X-ray Diffraction Spectroscopy (XRD), X-ray Crystallography, Cyclic Voltammetry, Pulse Polarography, Hydrodynamic Voltammetry, Potentiometry, Coulometry, Radiochemical analysis, Thermogravimetric Analysis (TGA), Ab initio computational methods, Enzyme-Linked Immunosorbent Assay (ELISA), Immunoassay, Chemiluminescence Spectroscopy, Circular Dichroism Spectroscopy (CD), Polarimetry, Light Scattering Photon Correlation Spectroscopy, Surface Plasmon Resonance Spectroscopy (SPR), Fluorescence Resonance Energy Transfer (FRET) Spectroscopy and/or any other suitable methods known in the art or combinations thereof.

Data Cleaning

In some embodiments, certain metabolites may be filtered from the dataset. For example, a Gaussian Process (GP) regression model may be fit to data points corresponding to pooled samples. Such a fit may be used as a computational internal standard. Metabolite data having missing values more than a threshold amount, such as more than 1%, 2%, 5%, 10%, 15% of the time or more, may be removed from the metabolite dataset. The data in the dataset may be normalized, for example by taking the logarithm of the ratio of the measured values and the GP predicted values for each time point ("normalized metabolite values"). A suitable GP kernel parameter may be selected. After internal standard normalization, coefficients of variation (CV) may be computed for metabolite data, in some cases using non-missing values only. Data for metabolites having a CV over a threshold value, such as 0.1, 0.2, 0.3, 0.4, 0.5 or more may be removed. Data for metabolites having a CV below a threshold value, such as 0.1, 0.05, 0.01, 0.005 or less, may also be removed.

Methods

In various embodiments, the methods and compositions described herein comprise use of LC-MS methods alone or in combination. For example, aliquots of the same sample may be analyzed using each aliquot in a different LC-MS method. LC-MS methods may target different metabolites, metabolite types or classes; such as, without limitation, amines and/or polar metabolites that ionize in the positive ion mode of a MS; central metabolites and/or polar metabolites that ionize in the negative ion mode of a MS; free fatty acids, bile acids, and/or metabolites of intermediate polarity; and/or polar and/or non-polar lipids.

Metabolites in an aliquot may be separated using a suitable LC column, such as, without limitation, an affinity column, an ion exchange column, a size exclusion column, a reversed phase column, a hydrophilic interaction column (HILIC), or a chiral chromatography column. A reversed phase column may comprise, without limitation, a C4 column, a C8 column, or a C18 column. The separated metabolites may be fed into a MS as they are being eluted from the LC. The MS may be run in positive ion mode or negative ion mode.

For example, metabolites in an aliquot, such as, without limitation, metabolites comprising amines and/or polar metabolites that ionize in the positive ion mode, may be extracted using a mixture of non-polar and polar solvent, such as acetonitrile and methanol. The mixture of metabolites may be separated using a suitable LC column, such as a hydrophilic interaction liquid chromatography (HILIC) column, e.g., under acidic mobile phase conditions. The MS data acquisition may be conducted in the positive ionization mode. Suitable metabolites for analysis using the foregoing steps comprise amino acids, amino acid metabolites, dipeptides, and other cationic metabolites.

For another example, metabolites in an aliquot, such as, without limitation, metabolites comprising central metabolites and/or polar metabolites that ionize in the negative ion mode, may be extracted using a polar solvent, such as methanol. The extracted metabolites may be separated using a suitable LC method, such as, without limitation, HILIC chromatography. An amine column under basic conditions may be used in some cases. The MS data acquisition may be conducted in the negative ion mode. Suitable metabolites for analysis using the foregoing steps comprise sugars, sugar phosphates, organic acids, purine, and pyrimidines.

For a further example, metabolites in an aliquot, such as, without limitation, metabolites comprising free fatty acids, bile acids, and/or metabolites of intermediate polarity, may be extracted using a polar solvent, such as methanol. The extracted metabolites may be separated using a suitable LC method, such as, without limitation, reversed phase chromatography, e.g., with a T3 UPLC column (C18 chromatography). The MS data acquisition may be conducted in the negative ion mode. Suitable metabolites for analysis using the foregoing steps comprise free fatty acids, bile acids, S1P, fatty acid oxidation products, and similar metabolites.

For yet a further example, metabolites in an aliquot, such as, without limitation, polar and/or non-polar lipids, may be extracted using a polar solvent, such as isopropanol. The extracted metabolites may be separated using a suitable LC method, such as, without limitation, reversed phase chromatography, e.g., with a C4 column. The MS data acquisition may be conducted in the positive ion mode. Suitable metabolites for analysis using the foregoing steps comprise lipids including, without limitation lysophosphatidylcholines, lysophosphatidylethanolamines, phosphatidylcholines, phosphatidylethanolamines, phosphatidylinositols, sphingomyelins, cholesterol esters, diacyglycerols, and triglycerides.

Data acquisition on a mass spectrometer may result in data files comprising mass spectra. For LC-MS methods, data files may comprise mass spectra collected over time, such as over the elution period from the LC. Relative quantitation and/or identification of metabolites may comprise detecting the LC-MS peaks. Such peaks may be detected and/or integrated using suitable software. Metabolite identification may comprise matching measured retention times and masses to a database of previously characterized compounds comprising retention times and masses and/or matching masses to a database of metabolite masses.

Predictors

This section relates to generating a survival predictor model, as well as using the survival predictor model to determine the value for a survival metric for a subject based on the survival predictor model and at least one sample from a subject. Survival predictor models described herein may use one or more survival biomarkers and/or one or more aging indicators. In various embodiments, survival predictor models use at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more survival biomarkers.

Models of all-cause mortality are used to build predictors and/or to use predictors for survival. Suitable statistical models for the predictor models described herein can take a variety of forms, including, without limitation, survival models, such as a model based on a hazard function comprising a generalized gamma distribution, exponential distribution, a Weibull distribution, a Gompertz distribution, a gamma distribution, a log-logistic distribution, or an exponential-logarithmic distribution, with or without frailty. In various embodiments a Cox model, such as a Cox proportional hazards (CoxPH) or an accelerated failure time model is used for a survival predictor model. In some cases, tree-structured survival models comprising a regression tree or classification tree, such as a survival random forest can be used. Further, in some cases a predictor model is built using Support Vector Machines, quadratic discriminant analysis, a LASSO, ridge regression, or elastic net regression model, or neural networks.

Survival predictor models may be built in supervised or unsupervised fashion. Regularization and/or clustering methods may be used to build the predictor models described herein. Parametric or semiparametric mathematical models may be used to build predictor models. Mathematical models may be fit to a data set using any suitable method known to a person of ordinary skill, including without limitation, gradient-based optimization, constrained optimization, maximum likelihood optimization and variations thereof, Bayesian inference methods, Newton's method, gradient descent, batch gradient descent, stochastic gradient descent, cyclical coordinate descent, or a combination thereof.

Predictor Performance

The performance of a survival predictor model may be assessed using a suitable method known in the art. In various embodiments, two or more survival predictor models are compared based on their assessed performance.

A variety of measures can be used to quantify the predictive discrimination of the survival predictor models discussed herein, including, without limitation, Hazard Ratio ("R"), area under the curve (AUC), Akaike's Information Criterion (AIC), Harrell's concordance index c, or a likelihood-ratio based statistic such as a $\chi^2$ test, Z-test, or G-test, or any other suitable measure known to a skilled person in the art.

A suitable concordance measure may be used to evaluate the overall performance of the survival predictor model. The concordance measure may be based on an explicit loss function between the predictor model output and the dataset, such as the survival time or on rank correlations between these quantities. For example, Harrell's concordance index c may be used as a rank-correlation measure. In various embodiments, survival predictor models described herein have a Harrell's concordance index that is at least or at least about 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or higher. Survival predictor models may have a Harrell's concordance index of at most or at most about 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99. Survival times in the presence of censoring may be ordered by assigning probability scores to pairs in which ordering is not obvious due to censoring, for example by the use of a pooled Kaplan-Meier estimate for event times. Alternative statistics may consider only usable pairs of predicted and measured data and calculate the proportion of concordant pairs among them. Usable pairs maybe selected excluding ties and/or censored data.

In some embodiments, predictive model performance is characterized by an area under the curve (AUC). In some embodiments, predictor model performance is characterized by an AUC greater than or greater than about 0.50, 0.51, 0.52, 0.60, 0.68, 0.70, 0.75, 0.79, 0.80, 0.81, 0.85, 0.89, 0.90, 0.95, 0.99, or greater. In some embodiments, predictor model performance is characterized by an AUC less than or less than about 0.99, 0.95, 0.90, 0.89, 0.85, 0.81, 0.80, 0.79, 0.75, 0.70, 0.68, 0.60, 0.52, 0.51 or less. The AUC of a predictor model may fall in a range having upper and lower bounds defined by any of the foregoing values; e.g., the AUC of a predictor model may be between 0.51-0.95.

In various embodiments, Akaike's Information Criterion (AIC) can be used to measure a predictor model M's performance having k parameters to be estimated. AIC can be expressed as a function of the log likelihood, or deviance, of the model adjusted by the number of parameters in the model:

$$AIC = 2k - 2\ln(L),$$

wherein L represents the maximized value of the likelihood function of a model M, i.e. $L = p(x|\theta, M)$ where $\theta$ are the parameter values that maximize the likelihood function; x represents observed data; and k represents the number parameters in a model M. For survival predictor models, AIC can be expressed as $$AIC = -2\log(L) + 2(i + 2 + k),$$

where i=0 for the exponential model, i=1 for the Weibull, log-logistic and log-normal models, and i=2 for the generalized gamma model.

In some embodiments, a predictor model M's performance is expressed as a corrected AIC ($AIC_c$). Generally, $AIC_c$, as a correction for finite sample sizes, relates to AIC while imposing a penalty for extra parameters. Thus, model fitting methods using $AIC_c$ as a measure of model performance may have a decreased chance of selecting models that have too many parameters, i.e. of overfitting. Suitable expressions of AIC can be selected based on the type of the statistical model used and are known in the art.

In various embodiments, survival times are used as a metric for all-cause mortality in a group of subjects. The relationship of one or more covariates and the survival time T can be modeled using the Cox proportional hazards (CoxPH) function as $$h_i(t|\beta, h_0) = h_0(t)\exp(x_i'\beta)$$

where $h_0(\cdot) \geq 0$ is a baseline hazard function and $\beta = (\beta_1, \ldots, \beta_{p_x})'$ denotes the $p_x$-dimensional vector of regression coefficients associated to the time-independent covariates $x_i=(x_{i1}, \ldots, x p_x)' \subset vi$. The impact of the covariates is subsumed in the predictor $\eta=\eta_i(\beta)=x_i'\beta$, which acts through the exponential function. The hazard ratio of two individuals with covariates $x_i$, $x_j$, $i \neq j$ can be denoted as $$\frac{h_i(t \mid \beta, \lambda_0)}{h_j(t \mid \beta, \lambda_0)} = \exp(\eta_i - \eta_j) = \exp((x_i - x_j)'\beta)$$

Using CoxPH as the model function, some embodiments optimize a regularized objective function which can be expressed as follows:

$$\lambda\|\beta\|^2 + \sum_{i:C_i=1} \log\theta_i - \log\left(\sum_{j:Y_j \geq Y_i} \theta_j\right)$$

where $C_i$ is 1 for occurred events (e.g. deaths) and 0 for censored, $Y_i$ are the event times, x is the regularization coefficient, which can be chosen using cross validation, $\theta_i = \exp(\beta^T X_i)$, $\beta$ represent the Cox weights (that are being optimized, as introduced in the prior paragraph) for $X_i$, the independent variables for individual i. In various embodiments, the independent variables can represent values for clinical factors and/or metabolites, such as in the form of metabolite normalized scores, which may be obtained from one or more samples from one or more subjects.

In some embodiments, regularization penalties may use lasso or ridge regression penalty or a combination thereof, such as an elastic net penalty. An elastic net penalty may be expressed as follows:

$$\lambda p_\alpha(\beta) = \lambda\left(\alpha \sum_{i=1}^{p} |\beta_i| + \frac{1}{2}(1-\alpha) \sum_{i=1}^{p} \beta_i^2\right)$$

with $0 \leq \alpha \leq 1$, where $\alpha=1$ represents the lasso penalty, and $\alpha=0$ represents the ridge penalty.

Model Fitting

Maximum and Partial Likelihood

Under certain assumptions, a full likelihood for the hazard function can be expressed as:

$$L(\theta \mid \mathcal{D}) = \prod_{i=1}^{n} L_i(\theta \mid \mathcal{D}) = \prod_{i=1}^{n} h_i(\tilde{t}_i \mid \theta)^{d_i} \exp(-H_i(\tilde{t}_i \mid \theta))$$

where $\theta=(\beta', \alpha')$ denote the parameters of interest that the survival distribution depends on, $\mathcal{D}$ denotes the data, and H denotes the cumulative hazard function given as:

$$H_T(t) = \int_0^t h_T(s)ds, \ t \geq 0.$$

The inference of the regression coefficients $\beta$ in the semiparametric Cox proportional hazards model can also be carried out in terms of the partial likelihood without the need to specify a baseline hazard function. The partial likelihood function can be expressed as $$pL(\beta \mid \mathcal{D}) = \prod_{i=1}^{n} \left\{\frac{\exp(x_i'\beta)}{\sum_{k=1}^{n} 1_{(\tilde{t}_k \geq \tilde{t}_i)} \exp(x_i'\beta)}\right\}^{d_i}$$

where the indicator function 1 in the denominator is used to describe the risk set $$R(\tilde{t}_i) = \{k : \tilde{t}_k \geq \tilde{t}_i\}$$

at the observed survival times, which consists of all individuals who are event-free and still under observation just prior each such observed survival time. The partial likelihood pL can be treated as a regular likelihood function and an inference on $\beta$ can be made accordingly, by optimizing pL. Further, the log partial likelihood log pL can be treated as an ordinary log-likelihood to derive partial maximum likelihood estimates of $\beta$ absent ties in the data set. Where the data set contains ties, approximations to the partial log-likelihood, such as the Breslow or Efron approximations to the partial log-likelihood, may be used for fitting models.

Bayesian Inference

As an alternative to likelihood inference, Bayesian inference can be used to fit a survival function. Bayesian inference relies on the posterior distribution of the model parameters $\theta \in \Theta$ given the observed data set $\mathcal{D}$. Using Bayes theorem, the density of the posterior distribution $p(\theta \mid \mathcal{D})$ can be expressed as $$p(\theta \mid \mathcal{D}) = \frac{L(\theta \mid \mathcal{D})p(\theta)}{\int_\Theta L(\theta \mid \mathcal{D})p(\theta)d\theta} \propto L(\theta \mid \mathcal{D})p(\theta),$$

where the denominator $\int_\Theta L(\theta \mid \mathcal{D})p(\theta)d\theta$ represents evidence or marginal likelihood. As such, the posterior distribution can be expressed in terms of the prior density $p(\theta)$, which can be used to represent prior knowledge of the complete set of model parameters $\theta \in \Theta$ and the likelihood $L(\theta \mid \mathcal{D})$.

Bayesian analysis can also be carried out using partial likelihood, where the full likelihood $L(\theta \mid \mathcal{D})$ in is replaced by the partial likelihood $pL(\theta \mid \mathcal{D})$.

Incorporation of additional assumptions about the model parameters into the estimation problem allows for constrained exploration of model parameters in regularization approaches. In practice, regularized regression techniques can be used to add a penalty term to the estimation function to enforce that the solutions are determined with respect to these constraints. The resulting penalized log-likelihood $$\log L_{pen}(\beta, \lambda) = \log L(\beta \mid \mathcal{D}) - pen(\beta; \lambda),$$

where $\log L(P \mid \mathcal{D})$ denotes the logarithm of the model specific likelihood $L(\beta \mid \mathcal{D})$ and $pen(\mathcal{D}; \lambda)$ is the penalty term, can then be optimized. The penalty term may be split into two components $pen(\beta; \lambda) = \lambda pen(\beta)$, where $pen(\beta)$ can define the form of the penalty and $X > 0$ can be utilized as the regularization parameter to tune the impact of $pen(\beta)$ at the solution of the regularized optimization problem. In many cases, reasonable values for the regularization parameter $\lambda$ can be determined using cross validation.

Under certain conditions, the penalty terms correspond to log-prior terms that express specific information about the regression coefficients. Using the posterior definition under Bayes theorem with an informative prior $p(\beta \mid \lambda)$ for the regression coefficients given the tuning parameter $\lambda > 0$ and an additional prior $p(\lambda)$, the posterior for an observation model $L(\mathcal{D}|\beta)$ can be expressed as $$p(\beta,\lambda|\mathcal{D}) \propto L(\mathcal{D}|\beta)p(\beta|\lambda)p(\lambda)$$

with $\theta=(\beta',\lambda)'$ and $p(\theta)=p(\beta|\lambda)p(\lambda)$. If the regularization parameter X is assumed to be known or fixed, the prior $p(\lambda)$ can be negligible and the resulting optimization problem becomes $$\hat{\beta}(\lambda)=\arg\max_\beta\{\log L(\mathcal{D}|\beta)+\log p(\beta|\lambda)\}$$

In many optimization approaches, the tuning parameter X is not fixed. Further, many approaches specify a prior $p(\lambda)$. A full Bayesian inference approach can be used where all model parameters are simultaneously estimated. In some cases, the regression parameters $\beta$ and the tuning parameter $\lambda$ can be jointly estimated. Typical choices for a prior $p(\beta|\lambda)$ for the regression coefficients include, without limitation Gaussian priors, double exponential priors, exponential power priors, Laplace priors, gamma priors, bimodal spike-and-slab priors, or combinations thereof.

Elastic-net Penalized Cox Proportional Hazards Model Fit Using Coordinate Descent In an exemplary embodiment, an elastic-net penalized Cox proportional hazards model is fit using coordinate descent. Assuming no ties, an algorithm that is geared to finding p which maximizes the likelihood $$L(\beta) = \prod_{i=1}^m \frac{e^{x_{j(i)}^T \beta}}{\sum_{j \in R_i} e^{x_j^T \beta}}$$

may be found by maximizing a scaled log partial likelihood, which can be expressed as $$\frac{2}{n}\ell(\beta) = \frac{2}{n}\left[\sum_{i=1}^m x_{j(i)}^T \beta - \log\left(\sum_{j \in R_i} e^{x_j^T \beta}\right)\right]$$

using as a constraint $\alpha\Sigma|\beta_i|+(1-\alpha)\Sigma\beta_i^2 \le c$. Using the Lagrangian formulation, the problem can be reduced to $$\hat{\beta} = \arg\max_\beta\left[\frac{2}{n}\left(\sum_{i=1}^m x_{j(i)}^T \beta - \log\left(\sum_{j \in R_i} e^{x_j^T \beta}\right)\right) - \lambda P_\alpha(\beta)\right]$$

where $$\lambda P_\alpha(\beta) = \lambda\left(\alpha \sum_{i=1}^p |\beta_i| + \frac{1}{2}(1-\alpha)\sum_{i=1}^p \beta_i^2\right).$$

As described above, $\alpha$ is varied between 0 and 1, inclusive, where $\alpha=1$ represents the lasso penalty and $\alpha=0$ represents the ridge penalty.

A strategy that is similar to the standard Newton Raphson algorithm may be used to maximize $\hat{\beta}$. As an alternative, instead of solving a general least squares problem, a penalized reweighted least squares problem can be solved. The gradient and Hessian of the log-partial likelihood with respect to $\beta$ and $\eta$, respectively, can be denoted by $\dot{\ell}(\beta)$ $\ddot{\ell}(\beta)$, $\ell'(\eta)$, and $\ell''(\eta)$, where X denotes the design matrix, $\beta$ denotes the coefficient vector and $\eta=X\beta$. A two term Taylor series expansion of the log-partial likelihood centered at $\tilde{\beta}$ can be expressed as $$\ell(\beta) \approx \ell(\tilde{\beta}) + (\beta-\tilde{\beta})^T \dot{\ell}(\tilde{\beta}) + (\beta-\tilde{\beta})^T \ddot{\ell}(\tilde{\beta})(\beta-\tilde{\beta})/2 = $$
$$\ell(\tilde{\beta}) + (X\beta-\tilde{\eta})^T \ell'(\tilde{\eta}) + (X\beta-\tilde{\eta})^T \ell''(\tilde{\eta})(X\beta-\tilde{\eta})/2$$

where $\tilde{\eta}==X\tilde{\beta}$. $\ell(\beta)$ can be reduced to $$\ell(\beta) \approx \frac{1}{2}(z(\tilde{\eta}) - X\beta)^T \ell''(\tilde{\eta})(z(\tilde{\eta}) - X\beta) + C(\tilde{\eta}, \tilde{\beta})$$

where $$z(\tilde{\eta})=\tilde{\eta}-\ell''(\tilde{\eta})^{-1}\ell'(\tilde{\eta})$$

and $C(\tilde{\eta}, \tilde{\beta})$ does not depend on $\beta$. $\ell''(\tilde{\eta}) \ell''(\tilde{\eta}) \ell''(\tilde{\eta})$. can be replaced by a diagonal matrix with the diagonal entries of $\ell''(\tilde{\eta}) \ell''(\tilde{\eta})$, for example, to speed up the fitting algorithm, where the ith diagonal entry of $\ell''(\tilde{\eta})$ is denoted by $w(\tilde{\eta})_i \omega(\tilde{\eta})_i$. Thus, an exemplary fitting algorithm can comprise the steps of: 1) initializing $\tilde{\beta}$ and setting $\tilde{\eta}=X\tilde{\beta}$; 2) computing $\ell''(\tilde{\eta})$ and $z(\tilde{\eta})$; 3) finding $\beta$ minimizing $$M(\beta) = \frac{1}{n}\sum_{i=1}^n w(\tilde{\eta})_i(z(\tilde{\eta})_i - x_i^T \beta)^2 + \lambda P_\alpha(\beta);$$

4) setting $\tilde{\beta}=\hat{\beta}$ and, $\tilde{\eta}=X\hat{\beta}$; and 5) repeating steps 2-4 until convergence of $\hat{\beta}$.

The minimization in step 3 can be done by cyclical coordinate descent. With estimates for $\beta_l$ for all $l \ne k$, the derivative of $M(\beta)$ can be expressed as $$\frac{\partial M}{\partial \beta_k} = \frac{1}{n}\sum_{i=1}^n w(\tilde{\eta})_i x_{ik}(z(\tilde{\eta})_i - x_i^T \beta) + \lambda\alpha \cdot \text{sgn}(\beta_k) + \lambda(1-\alpha)\beta_k.$$

The coordinate solution can be expressed as $$\hat{\beta}_k = \frac{S\left(\frac{1}{n}\sum_{i=1}^n w(\tilde{\eta})_i x_{i,k}\left[z(\tilde{\eta})_i - \sum_{j \ne k} x_{ij}\beta_j\right], \lambda\alpha\right)}{\frac{1}{n}\sum_{i=1}^p w(\tilde{\eta})_i x_{ik}^2 + \lambda(1-\alpha)}$$

with $$S(x,\lambda)=\text{sgn}(x)(|x|-\Delta)+$$

$$w(\tilde{\eta})_k = \ell''(\tilde{\eta})_{k,k} = \sum_{i \in C_k}\left[\frac{e^{\tilde{\eta}_k}\sum_{j \in R_i} e^{\tilde{\eta}_j} - (e^{\tilde{\eta}_k})^2}{\left(\sum_{j \in R_i} e^{\tilde{\eta}_j}\right)^2}\right]$$

$$z(\tilde{\eta})_k = \tilde{\eta}_k - \frac{\ell'(\tilde{\eta})_k}{\ell''(\tilde{\eta})_{k,k}} = \tilde{\eta}_k + \frac{1}{w(\tilde{\eta})_k}\left[\delta_k - \sum_{i \in C_k}\left(\frac{e^{\tilde{\eta}_k}}{\sum_{j \in R_i} e^{\tilde{\eta}_j}}\right)\right]$$

and $C_k$ is the set of i with $t_i < y_k$ (the times for which observation k is still at risk).

By combining a usual least squares coordinate wise solution with proportional shrinkage from the ridge regression penalty and soft thresholding from the lasso penalty, a solution for $\beta_k$ may be reached by applying $$\hat{\beta}_k = \frac{S\left(\frac{1}{n}\sum_{i=1}^{n} w(\tilde{\eta})_i x_{i,k} \left[z(\tilde{\eta})_i - \sum_{j \neq k} x_{ij} \beta_j\right], \lambda\alpha\right)}{\frac{1}{n}\sum_{i=1}^{p} w(\tilde{\eta})_i x_{ik}^2 + \lambda(1-\alpha)}$$

to the coordinates of $\beta$ in a cyclic fashion until convergence minimizes $M(\beta)$.

To obtain models for more than one value of $\lambda$, the solutions for a path of $\lambda$ values may be computed for fixed $\alpha$. Beginning with $\lambda$ sufficiently large to set $\beta=0$, $\lambda$ may be decreased until arriving near the unregularized solution. The first $\lambda$ maybe set to $$\lambda_{max} = \max_j \frac{1}{n\alpha} \sum_{i=1}^{n} w_i(0) x_{ij} z(0)_i.$$

Solutions over a grid of m values between $\lambda_{min}$ and $\lambda_{max}$ may be computed by setting $\lambda_{min} = \epsilon \lambda_{max}$, where $\lambda_j = \lambda_{max} (\lambda_{min}/\lambda_{max})^{j/m}$ for j=0, . . . , m. A suitable value for m may be selected as appropriate in a given implementation, for example m=100. A suitable value of $\epsilon$ may also appropriately be selected in a given implementation; for example, $\epsilon=0.05$ for n<p or $\epsilon=0.0001$ for n≥p.

Further methods for the computation of $w_k$ and $z_k$ can be implemented as described in Simon et al. (Simon, N., Friedman, J., Hastie, T., Tibshirani, R. (2011) Regularization Paths for Cox's Proportional Hazards Model via Coordinate Descent, Journal of Statistical Software, Vol. 39(5) 1-13), which is herein incorporated by reference in its entirety. Weights and ties can be handled as described in Simon et al.

Support Vector Machines

In various embodiments, margin maximization algorithms of support vector machines (SVMs) may be implemented to model survival data. Under such an approach, a hyperplane {x' β=−bt} can be constructed separating the individual(s) deceased or having reached an observed event at time t from the individuals remaining in the risk set after time t, at every event time t, where $\beta \in \mathbb{R}^d$ are the coefficients. The margin may be maximized as in support vector classification machines. Using this approach, for different event times t, the hyperplanes can just be translated, keeping their orientation (determined by β) the same, in analogy to using the same β for all events under proportional hazards assumptions.

In this approach, the first hyperplane can be set to separate $\mathcal{D}_1 = \{i_1\}$ from $\mathcal{R}^+_1 := \{i_2, i_3, i_4, i_5, i_6\}$, i.e. the subject to experience an event (such as an aging event), from the remaining individuals which are still at risk right after t=1. Similarly, the second hyperplane can be set to separate $\mathcal{D}_2 := \{i_2\}$ from $\mathcal{R}^+_2 := \{i_3, i_4, i_5, i_6\}$; the third hyperplane can be set to separate $\mathcal{D}_5 := f\{i_5\}$ from $\mathcal{R}^+_5 := \{i_6\}$; etc.

Some modeling approaches may relax the condition that the hyperplanes achieve perfect separation. Similar to soft-margin SVMs, some observations may be allowed to lie on the 'wrong' side of the margin, with an associated penalty that is proportional to the distance $\xi_{ij}$ between the observation and the corresponding margin separating the individual i from a survivor j.

Survival support vector machines can take various forms, e.g. they may be ranking-based, regression-based, or can take the form of a hybrid of the ranking- and regression-based approaches. As an example, the objective function of a ranking-based linear survival support vector machine may be expressed as:

$$f(\beta) = \frac{1}{2}\beta^T\beta + \frac{\gamma}{2}\sum_{i,j\in\mathcal{P}} \max(0, 1 - (\beta^T x_i - \beta^T x_j))^2,$$

where γ>0 is a regularization parameter. A set of data points X can be ranked with respect to their predicted survival time according to elements of Xβ.

In some embodiments, Newton's method is applied to minimize the objective function. Where suitable, a truncated Newton method that uses a linear conjugate gradient method to compute the search direction may be applied. Use of survival support vector machines to model survival data is described in further detail in Polsterl et al. (S. Pölsterl, N. Navab, A. Katouzian. 2015. Fast Training of Support Vector Machines for Survival Analysis. Machine Learning and Knowledge Discovery in Databases), which is herein incorporated by reference in its entirety.

Survival predictor models built using any of the described methods or other suitable methods known in the art may have covariates comprising a representation of one or more survival biomarkers and/or one or more aging indicators.

Selection of Biomarkers

In some embodiments, significance associated with one or more metabolites and/or clinical factors is measured by its estimated impact on the value of a subject's survival metric, relative chance of survival, or chance of having and aging event (e.g., death or acquiring an aging-related disease) within an equivalent time period as compared to a default state ("relative survival risk"). The default state may relate to a subject having a normalized metabolite value at a unit amount lower. In cases tracking a metabolite's presence or absence only, a unit amount may mean the difference between having a metabolite present and absent. In some embodiments, the relative survival risk is measured with respect to a comparison group having, setting, representing, or approximating the default state. For example, a survival predictor model that is configured to calculate relative survival risk may have used data from samples from a comparison group. Such a survival predictor model may determine a value for relative survival risk based on the presence or abundance of one or more metabolites, such as survival biomarkers, and/or clinical factors. The unit amount for a normalized metabolite value may be determined based on the distribution of a metabolite's abundance within a set of samples from subjects. A unit amount of a significant metabolite may have an impact on the value of relative survival risk of at least or at least about 1.01, 1.05, 1.1. 1.15, 1.2, 1.3, 1.4, 1.5, 1.6, 1.7, 1.8, 1.9, 2.0, 2.1, 2.2, 2.3 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3 or greater. A unit amount of a significant metabolite may have an impact on the value of relative survival risk of at most or at most about 0.99, 0.95, 0.90, 0.87, 0.85, 0.8, 0.75, 0.7, 0.65, 0.60, 0.58, 0.5, 0.53, 0.52, 0.51, 0.49, 0.48, 0.47, 0.46, 0.45, 0.44, 0.43, 0.42, 0.41, 0.4, 0.39, 0.38, 0.37, 0.36, 0.35, 0.34, 0.33, 0.32, 0.31, 0.3, 0.29, 0.28, 0.27, 0.26, 0.25, 0.24, 0.23, or less. One or more survival biomarkers may be selected from metabolites having a threshold amount of significance.

A survival metric can be calculated by combining data representing presence and/or abundance of multiple survival biomarkers, such as at least or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75 or more biomarkers. A survival metric can be calculated by combining data representing presence and/or abundance of multiple protein markers, such as at least or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75 or more biomarkers with data representing one or more clinical factors (e.g., age, sex, race, ethnicity, smoking status, alcohol consumption status, diastolic blood pressure, systolic blood pressure, a family history parameter, a medical history parameter, a medical symptom parameter, height, weight, a body-mass index, or resting heart rate of a subject). Survival predictor models, described in further detail elsewhere herein, may be capable of combining selected survival biomarker(s) and clinical factor(s) to determine the survival metric.

A univariate or multivariate survival predictor model may be assessed for its estimated impact on the value of a subject's survival metric, relative chance of survival, or chance of having and aging event within an equivalent time period as compared to a default state. One way to assess a predictor's performance is to calculate a hazard ratio using a Cox proportional hazards model. In the case of a continuous univariate predictor, the hazard ratio reflects the change in the risk of death if the value of the predictor rises by one unit. In the case of a continuous multivariate survival predictor model, the hazard ratio reflects the change in the risk of death if the output of the multivariate model rises by one unit. The covariate vector used in a multivariate model may represent values of one or more aging indicators and/or one or more normalized metabolite values.

A score produced via a combination of data types can be useful in classifying, sorting, or rating a sample from which the score was generated.

Clinical Factors

In some embodiments, one or more clinical factors in a subject, can be assessed. In some embodiments, assessment of one or more clinical factors in a subject can be combined with a survival biomarker analysis in the subject to provide a survival metric for the subject.

The term "clinical factor" comprises a measure of a condition of a subject, e.g., disease activity or severity. "Clinical factor" comprises all indicators of a subject's health status, which may be obtained from a patient's health record and/or other characteristics of a subject, such as, without limitation, age and gender. A clinical factor can be a score, a value, or a set of values that can be obtained from evaluation of a sample (or population of samples) from a subject. A clinical factor can also be predicted by markers, including genetic markers, and/or other parameters such as gene expression profiles.

A clinical factor may comprise, age, sex, race, ethnicity, smoking status, alcohol consumption status, diastolic blood pressure, systolic blood pressure, a family history parameter, a medical history parameter, such as a disease diagnosis, a medical symptom parameter, height, weight, a body-mass index, or resting heart rate of a subject.

In some embodiments, one or more clinical factors are used to identify significant metabolites. In some embodiments, one or more clinical factors are used to select survival biomarkers to be used in a survival predictor model. In some embodiments, one or more clinical factors are used as covariates in a survival predictor model. In some embodiments, one or more clinical factors are used to include or exclude subjects from a study cohort, such as a study cohort for model testing or model cross-validation. In each case, the methods and compositions described herein may use at least or at least about 1, 2, 3, 4, 5, 6, 7, 8, 9, 10, 11, 12, 13, 14, 15, 16, 17, 18, 19, 20, or more clinical factors.

Computer Implementation

The methods and compositions described herein, including the methods of generating a prediction model and the methods of for determining a survival metric for a subject, may comprise a computer or use thereof.

In one embodiment, a computer comprises at least one processor coupled to a chipset. Also coupled to the chipset may be one or more of a memory, a storage device, a keyboard, a graphics adapter, a pointing device, and a network adapter. A display may be coupled to the graphics adapter. In one embodiment, the functionality of the chipset is provided by a memory controller hub and an I/O controller hub. In another embodiment, the memory is coupled directly to the processor instead of the chipset.

The storage device may be any device capable of holding data, like a hard drive, compact disk read-only memory (CD-ROM), DVD, or a solid-state memory device. The memory may be configured to hold instructions and data used by the processor. The pointing device may be a mouse, track ball, or other type of pointing device, and is used in combination with the keyboard to input data into the computer system. The graphics adapter may be configured to display images and other information on the display. The network adapter may be configured to couple the computer system to a local or wide area network.

As is known in the art, a suitable computer can have different and/or other components than those described previously. In addition, the computer can lack certain components. A storage device can be local and/or remote from the computer (such as embodied within a storage area network (SAN)).

In various embodiments, the computer is be adapted to execute computer program modules for providing functionality described herein. A computer module may comprise a computer program logic and/or computer program parameters utilized to provide the specified functionality. A module can be implemented in hardware, firmware, and/or software. Program modules may be stored on the storage device, loaded into the memory, and/or executed by the processor.

The methods and compositions described herein may comprise other and/or different modules than the ones described here. The functionality attributed to any module or modules may be performed by one or more other or different modules in other embodiments. This description may occasionally omit the term "modul" for purposes of clarity and convenience.

Methods of Therapy

In various embodiments, the methods and compositions described herein comprise treatment of subjects, such as a treatment of an aging related disease. A treatment may be applied following a diagnostic step performed according to the various embodiments described throughout, including those comprising determination of a survival metric.

In various embodiments, the methods and compositions described herein comprise a therapeutically effective amount of a drug, such as a drug that is identified through a drug screen as described in further detail elsewhere herein and/or administration or distribution thereof. These drugs may be formulated in pharmaceutical compositions. These compositions may comprise, in addition to one or more of the drugs identified through a drug screen, a pharmaceutically acceptable excipient, carrier, buffer, stabilizer or other materials well known to those skilled in the art. Such materials may be selected so that they are non-toxic and do not interfere with the efficacy of an active ingredient, such as a drug that is identified through a drug screen as described in further detail elsewhere herein. The precise nature of the carrier or other material may depend on the route of administration, e.g., oral, intravenous, cutaneous or subcutaneous, nasal, intramuscular, intraperitoneal routes.

Pharmaceutical compositions for oral administration may be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, and Lactated Ringer's Injection. Preservatives, stabilizers, buffers, antioxidants and/or other additives can be included, as required.

Whether it is a polypeptide, antibody, nucleic acid, small molecule or other pharmaceutically useful compound that is to be given to an individual, administration dose may be set to be in a "therapeutically effective amount," such as in a "prophylactically effective amount," the amount being sufficient to show benefit to the individual. The amount which will be therapeutically effective in the treatment of a particular individual's disorder or condition may depend on the symptoms and severity thereof. The appropriate dosage, e.g., a safe dosage or a therapeutically effective dosage, may be determined by any suitable clinical technique known in the art, e.g., without limitation in vitro and/or in vivo assays.

A composition can be administered alone or in combination with other treatments, either simultaneously or sequentially dependent upon the condition to be treated.

Suitable survival related therapies for a subject may comprise advising lifestyle changes, cessation of smoking, avoiding secondhand smoke, eating a healthy diet, regular exercise, achieving and/or maintaining a healthy weight, keeping a healthy mental attitude; weight management; reducing blood pressure; reducing cholesterol; managing diabetes; administration of therapeutics such as drugs, undertaking of one or more procedures; performing further diagnostics on the subject; assessing the subject's health further; or optimizing medical therapy.

Screens

In various embodiments, the methods and compositions described herein are used to identify one or more survival factors, such as outside factors, that have a positive or negative effect on a survival metric, time to aging event, chance of survival, life expectancy, chance of death, and/or another survival related outcome. In some embodiments, survival predictor model outputs are used to identify a survival factor. A test target, such as, without limitation, a subject, an organ, a tissue, a cell, or a portion thereof may be contacted by or interacted with one or more candidate factors. The test target may be derived from an animal, such as a mammal, e.g., a rat, a mouse, a monkey, a rabbit, a pig, or a human. One or more samples may be collected from the test target. A metabolite profile may be obtained from the test target or one or more samples. A survival predictor model may be used to obtain a survival metric based on the metabolite profile. Survival metrics of various candidate factors may be compared to identify candidate factors that have a high likelihood of having a significant relationship to survival related outcomes. In some embodiments, candidate factors comprise a library of test drugs. For example, if drug-tested test targets show significantly altered prediction for survival, the tested drug may be selected for use in aging relating applications, including therapeutic applications. Accordingly, a drug screen may be implemented screening test drugs for survival related outcomes.

Kits

Also disclosed herein are kits for obtaining a survival metric. Such kits may comprise one or more of a sample collection container, one or more reagents for detecting the presence and/or abundance of one or more survival biomarkers, instructions for calculating a survival metric based on the expression levels, and credentials to access a computer software. The computer software may be configured to intake survival biomarker data, determine a survival biometric, and/or store survival biomarker data and/or survival biometric.

In some embodiments, a kit comprises software for performing instructions included with the kit. The software and instructions may be provided together. For example, a kit can include software for generating a survival metric by mathematically combining data generated using the set of reagents.

A kit can include instructions for classifying a sample according to a score. A kit can include instructions for rating a survival related outcome, such as life expectancy, chance of survival, or risk of death using a survival metric. Rating may comprise a determination of an increase or decrease in a survival related outcome.

A kit may comprise instructions for obtaining data representing at least one survival biomarker and/or at least one clinical factor associated with a subject as described in further detail elsewhere herein. In certain embodiments, a kit can include instructions for mathematically combining the data representing at least one clinical factor with data representing the presence or abundance of one or more survival biomarkers to generate a score.

A kit may include instructions for taking at least one action based on a score for a subject, e.g., treating the subject, advising lifestyle changes to the subject, performing a procedure on the subject, performing further diagnostics on the subject, assessing the subject's health further, or optimizing medical therapy.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of metabolomics, protein chemistry, biochemistry, recombinant DNA techniques and pharmacology, within the skill of the art. Such techniques are explained fully in the literature. See, e.g., W. J. Griffiths, *Metabolomics, metabonomics and metabolite profiling* (Cambridge: Cambridge RSC Publishing, 2008); S. G. Villas-Bôas, et al., *Metabolome Analysis: An Introduction* (John Wiley & Sons, Inc., New Jersey, USA, 2007); U. Roessner and D. A. Dias, *Metabolomics Tools for Natural Product Discovery* (Springer Science bBusiness Media, LLC, Philadelphia, USA, 2013); M. Lammerhofer and W. Weckwerth, *Metabolomics in Practice: Successful Strategies to Generate and Analyze Metabolic Data* (John Wiley & Sons: Hoboken, NJ, USA, 2013); A. Sussulini, *Metabolomics: From Fundamentals to Clinical Applications* (Springer International Publishing, A G, 2017); T.E. Creighton, Proteins: *Structures and Molecular Properties* (W.H. Freeman and Company, 1993); A.L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B(1992).

Example 1: Estonian Study Cohort

In order to study biomarkers that are associated with aging, the Estonian study cohort was designed. Study subjects were drawn from the Estonian Biobank cohort (Liis Leitsalu, Toomas Haller, Tõnu Esko, Mari-Liis Tammesoo, Helene Alavere, Harold Snieder, Markus Perola, Pauline C Ng, Reedik Magi, Lili Milani, Krista Fischer, and Andres Metspalu. Cohort Profile: Estonian Biobank of the Estonian Genome Center, University of Tartu. Int. J. Epidemiol. first published online Feb. 11, 2014 doi:10.1093/ije/dyt268). 572 subjects were used for the study. The age of the subjected ranged from 70-79 years old. All subjects were free of certain major age-related diseases (Hypertensive heart disease, Type 2 diabetes, Coronary artery disease, Cancer, Type 1 diabetes, COPD, Stroke, Alzheimer's) at the time of sample collection. Each subject had between 8 and 14 years of follow up data available as electronic health records. For the 572 subjects in the study cohort, 133 deaths were recorded.

Example 2: Estonian Cohort Sample Collection

Biological samples were collected from the cohort subjects in Example 1 as 30-50 mL of venous blood into EDTA Vacutainers. Containers were transported to the central laboratory of the Estonian Biobank at +4 to +6° C. (within 6 to 36 hours) where DNA, plasma and WBCs were isolated immediately, packaged into CryoBioSystem high security straws (DNA in 10-14, plasma in 7, WBCs in 2 straws) and stored in liquid nitrogen.

Example 3: Estonian Cohort Metabolomics Protocols

Plasma samples from the 576 subjects were sent to the Broad institute and analyzed for metabolomics profiling using the Metabolite Profiling Platform (MPP). The MPP uses liquid chromatography (LC) coupled to mass spectrometry (MS; as coupled, LC-MS) to conduct metabolic profiling on biological samples, including plasma. A combination of four LC-MS methods is used on the MPP. The LC-MS methods measure complementary sets of metabolite classes, ranging from polar metabolites, such as organic acids, to non-polar lipids, such as triglycerides. In each method, the MS data are acquired using sensitive, high resolution mass spectrometers (e.g., Q Exactive, Thermo Scientific) that enable untargeted measurement of metabolites of known identity (>300 metabolites) and heretofore unidentified metabolites in the same set of data acquisition experiments. The four LC-MS methods are summarized as follows:

Amines and polar metabolites that ionize in the positive ion mode. In this LC-MS method, polar metabolites are extracted using a mixture of acetonitrile and methanol and the mixtures are separated using a hydrophilic interaction liquid chromatography (HILIC) column under acidic mobile phase conditions. The MS analyses are conducted in the positive ionization mode. Suitable metabolites measured using this method include, without limitation, amino acids, amino acid metabolites, dipeptides, and other cationic metabolites.

Central metabolites and polar metabolites that ionize in the negative ion mode. In this LC-MS method, metabolites are extracted using four volumes of 80% methanol and then separated using HILIC chromatography (amine column) under basic conditions. MS data are acquired in the negative ion mode. Suitable metabolites include, without limitation, sugars, sugar phosphates, organic acids, purine, and pyrimidines.

Free fatty acids, bile acids, and metabolites of intermediate polarity. In this LC-MS method, samples are extracted using 3 volumes of 100% methanol and then separated using reversed chromatography with a T3 UPLC column (C18 chromatography). The MS analyses are conducted in the negative ion mode. Suitable metabolites include, without limitation, free fatty acids, bile acids, S1P, fatty acid oxidation products, and similar metabolites.

Polar and non-polar lipids. In this LC-MS method, lipids are extracted using 19 volumes of 100% isopropanol and then separated using reversed phase chromatography with a C4 column. The MS data are acquired in the positive ion mode. Suitable lipids for this method include, without limitation, lysophosphatidylcholines, lysophosphatidylethanolamines, phosphatidylcholines, phosphatidylethanolamines, phosphatidylinositols, sphingomyelins, cholesterol esters, diacyglycerols, and triglycerides.

Example 4: Estonian Cohort LC-MS Data Processing

Metabolite relative quantitation and identification for MPP rely on a panel of four LC-MS methods that generate raw data files of high resolution mass spectra acquired over time. In each raw data file, LC-MS peaks are detected and integrated using Progenesis CoMet software (v 2.0, Nonlinear Dynamics) and identification is initially conducted by matching measured retention time and masses to a database of >500 characterized compounds and by matching exact masses to a database of >8000 metabolites.

Example 5: Estonian Cohort Quality Control for MS Data

The quality of the data processed as described in Example 4 is checked using several strategies.
  (i) Synthetic reference standards. For each of the LC-MS methods described in Example 3, purchased authentic reference standards from commercial sources were formulated into mixtures containing up to about 130 compounds in each. To assure analytical performance of the LC-MS system, typically the samples are analyzed before the initiation of the sample queue and the data are evaluated for reproducibility of chromatographic retention times, quality of chromatographic peak shapes, and LC-MS peak area (sensitivity of analysis). These samples are also monitored periodically during the analysis queue and at the end of the queue to assure that analytical performance is maintained.

(ii) Internal standards. Synthetic internal standards are typically introduced into each LC-MS sample during the extraction procedure for each LC-MS method described in Example 3. Standards include both stable isotope-labeled compounds and non-physiologic reference compounds. The internal standard signals in each sample are monitored as a function of analysis time to (1) ensure that each sample injected properly and (2) monitor LC-MS system performance over time. Samples with low measured internal standard signals are flagged for reanalysis.

(iii) Periodic analyses of external reference samples. In each analysis queue, a pooled-plasma reference sample is inserted after sets of about twenty study samples. The data from the pooled reference samples are evaluated to assure (1) maintenance of data quality (metabolite retention times and LC-MS peak shapes) and (2) the reproducibility of the data, by calculating coefficients of variation for each measured metabolite. If the pooled reference data indicate loss of analytical performance, the queue is stopped until the problem is corrected and the analysis queue is restarted from the last point at which data quality was acceptable.

Example 6: Data Cleaning—First Example

LC-MS data was received from the samples analyzed using Broad Institute's MPP. A Gaussian Process (GP) regression model was fit to data points corresponding to pooled samples (computational internal standard). Metabolite data having missing values more than 10% of the time were removed from the LC-MS data. The remaining data were normalized by taking the logarithm of the ratio of the measured values and the GP predicted values for each time point to account for instrument drift in a non-parametric way. The GP kernel parameter was set to $10^4$. After internal standard normalization, coefficients of variation (CV) were computed for all metabolite data using non-missing values only. Metabolite data having a CV over 0.2 or a standard deviation below 0.01 were removed. The remaining data were corrected for gender and time of last meal by linear regression, followed by rank-based inverse normal transformation (INT) and imputation. The imputation was done simultaneously with INT by setting missing values as the lowest rank prior to INT. The resulting data (corresponding to 13462 metabolites) have no missing values and follow a normal distribution per metabolite.

At a false discovery rate of 5%, 661 metabolites associate significantly with all-cause mortality (Table 1).

TABLE 1

| Compound | HMDB ID | Metabolite | Method | RT | m/z | log10_pval |
| --- | --- | --- | --- | --- | --- | --- |
| QI1972 | | | HIL-pos | 7.71 | 179.9824 | −8.5663 |
| QI11 | HMDB01906 | alpha-Aminoisobutyric acid | HIL-pos | 7.71 | 104.0711 | −8.0568 |
| QI3594 | | | HIL-pos | 8.63 | 264.1191 | −7.96361 |
| QI1322 | | | HIL-pos | 4.84 | 151.0615 | −7.72731 |
| QI3862 | | | HIL-pos | 4.82 | 283.1036 | −7.62064 |
| QI3933 | | | HIL-pos | 10.37 | 287.2442 | −7.4685 |
| QI4231 | | | HIL-pos | 5.41 | 312.1301 | −7.27946 |
| QI6954 | | | HIL-pos | 5.38 | 750.5432 | −7.14147 |
| cmp.QI77 | HMDB11420 | C38:7 PE plasmalogen | C8-pos | 8.67 | 748.5273 | −7.03813 |
| cmp.QI78 | HMDB11387 | C38:6 PE plasmalogen | C8-pos | 8.86 | 750.5431 | −6.76089 |
| cmp.QI4994 | | | C8-pos | 8.93 | 772.5239 | −6.67176 |
| cmp.QI2812 | | | C8-pos | 10.18 | 567.4561 | −6.62129 |
| cmp.QI2539 | | | C8-pos | 10.18 | 536.4373 | −6.53493 |
| QI6045 | | | HIL-pos | 1.65 | 550.4173 | −6.53367 |
| QI2665 | | | C18-neg | 1.01 | 283.9941 | −6.49773 |
| QI2020 | | | HIL-pos | 7.7 | 181.9804 | −6.47327 |
| cmp.QI6054 | | | C8-pos | 9.4 | 863.6231 | −6.39254 |
| cmp.QI2531 | | | C8-pos | 10.18 | 535.43 | −6.26371 |
| QI6382 | | | HIL-pos | 1.99 | 610.4678 | −6.15552 |
| cmp.QI3377 | | | C8-pos | 10.18 | 621.464 | −6.14621 |
| cmp.QI4972 | | | C8-pos | 8.67 | 770.5091 | −6.07414 |
| cmp.QI81 | HMDB11394 | C40:7 PE plasmalogen | C8-pos | 9.11 | 776.5583 | −6.02322 |
| QI5699 | | | HIL-pos | 2.39 | 491.3481 | −6.021 |
| cmp.QI6144 | | | C8-pos | 8.17 | 870.5224 | −5.99375 |
| QI7061 | | | HIL-pos | 7.04 | 773.6531 | −5.89817 |
| QI6994 | | | HIL-pos | 7.06 | 759.6373 | −5.848 |
| cmp.QI6343 | | | C8-pos | 9.5 | 889.6382 | −5.84128 |
| QI6945 | | | HIL-pos | 5.39 | 748.5274 | −5.7981 |
| cmp.QI5061 | | | C8-pos | 8.65 | 778.5737 | −5.73154 |
| cmp.QI5172 | | | C8-pos | 8.5 | 788.5561 | −5.7246 |
| QI1093 | | | C18-neg | 9.01 | 163.0751 | −5.72018 |
| QI2606 | | | HIL-pos | 5.47 | 208.072 | −5.71115 |
| QI6064 | | | HIL-pos | 1.65 | 552.433 | −5.70657 |
| cmp.QI5003 | | | C8-pos | 9.4 | 773.6529 | −5.69841 |
| QI7070 | | | HIL-pos | 5.35 | 776.5589 | −5.69011 |
| cmp.QI2203 | | | C8-pos | 9.78 | 491.8171 | −5.68964 |
| cmp.QI6754 | | | C8-pos | 8.17 | 938.5102 | −5.65111 |
| cmp.QI5286 | | | C8-pos | 9.11 | 798.5405 | −5.62842 |
| cmp.QI5307 | | | C8-pos | 9.5 | 799.6687 | −5.61567 |
| QI7056 | | | HIL-pos | 5.36 | 772.5265 | −5.59774 |
| cmp.QI5917 | | | C8-pos | 9.32 | 851.6254 | −5.58318 |
| cmp.QI4470 | | | C8-pos | 8.46 | 722.5103 | −5.56929 |
| QI6146 | | | HIL-pos | 1.61 | 570.4433 | −5.56864 |

TABLE 1-continued

| Compound | HMDB ID | Metabolite | Method | RT | m/z | log10_pval |
|---|---|---|---|---|---|---|
| cmp.QI47 | HMDB11221 | C36:5 PC plasmalogen-A | C8-pos | 8.49 | 766.5733 | −5.56574 |
| cmp.QI1603 | | | C8-pos | 8.17 | 410.2556 | −5.50011 |
| QI7082 | | | HIL-pos | 6.48 | 778.5742 | −5.46896 |
| cmp.QI5348 | | | C8-pos | 8.16 | 802.5349 | −5.44906 |
| cmp.QI5567 | | | C8-pos | 9.11 | 820.5228 | −5.4403 |
| QI6850 | | | HIL-pos | 5.41 | 722.5118 | −5.39814 |
| QI7013 | | | HIL-pos | 6.51 | 764.5587 | −5.37645 |
| QI2622 | | | HIL-pos | 4.28 | 209.0558 | −5.31253 |
| cmp.QI5335 | | | C8-pos | 9.78 | 801.6843 | −5.30718 |
| cmp.QI6367 | | | C8-pos | 9.78 | 891.6537 | −5.28839 |
| cmp.QI38 | HMDB08511 | C40:10 PC | C8-pos | 8.05 | 826.5353 | −5.26873 |
| cmp.QI5590 | | | C8-pos | 9.5 | 821.6505 | −5.26811 |
| QI123 | HMDB00767 | Pseudouridine | HIL-pos | 4.28 | 245.0768 | −5.26553 |
| QI3323 | | | HIL-pos | 4.28 | 246.0801 | −5.24295 |
| QI2497 | | | C18-neg | 7.6 | 264.1294 | −5.21814 |
| QI569 | | | HIL-pos | 5.45 | 112.0509 | −5.20531 |
| cmp.QI4910 | | | C8-pos | 8.46 | 764.5566 | −5.19519 |
| QI5268 | | | C18-neg | 10.82 | 498.32 | −5.13512 |
| TF42 | HMDB00127 | glucuronate | HILIC-neg | 5 | 193.0354 | −5.12363 |
| QI2222 | | | HIL-pos | 4.29 | 191.0452 | −5.11707 |
| cmp.QI4090 | | | C8-pos | 11.13 | 686.5867 | −5.10645 |
| cmp.QI5016 | | | C8-pos | 8.79 | 774.542 | −5.08479 |
| cmp.QI1672 | | | C8-pos | 9.78 | 420.821 | −5.07407 |
| QI7053 | | | C18-neg | 10.59 | 712.2604 | −5.06338 |
| QI1952 | | | HIL-pos | 4.28 | 179.0451 | −5.04837 |
| cmp.QI6202 | | | C8-pos | 9.28 | 875.6222 | −5.03076 |
| cmp.QI6398 | | | C8-pos | 8.05 | 894.5228 | −4.99605 |
| QI6939 | | | HIL-pos | 5.4 | 746.5112 | −4.97243 |
| QI3522 | | | C18-neg | 8.35 | 337.1661 | −4.96501 |
| cmp.QI104 | HMDB12102 | C20:0 SM | C8-pos | 9.17 | 759.6373 | −4.94598 |
| QI6145 | | | HIL-pos | 1.73 | 570.4427 | −4.94274 |
| cmp.QI6878 | | | C8-pos | 9.79 | 959.6415 | −4.9411 |
| QI7055 | | | HIL-pos | 7.04 | 771.6373 | −4.9259 |
| QI2265 | | | HIL-pos | 2.02 | 193.0862 | −4.92117 |
| cmp.QI5316 | | | C8-pos | 9.23 | 800.556 | −4.91448 |
| QI2494 | | | C18-neg | 7.6 | 263.6279 | −4.89983 |
| cmp.QI5667 | | | C8-pos | 7.95 | 829.5552 | −4.89063 |
| cmp.QI3920 | | | C8-pos | 11.43 | 671.5757 | −4.86444 |
| cmp.QI5618 | | | C8-pos | 9.78 | 823.6661 | −4.82324 |
| cmp.QI124 | HMDB06731 | C20:5 CE +NH4 | C8-pos | 11.43 | 688.6025 | −4.81632 |
| QI5948 | | | HIL-pos | 1.59 | 536.4381 | −4.80293 |
| TF35 | HMDB01999 | eicosapentaenoic acid | HILIC-neg | 3.1 | 301.2173 | −4.80241 |
| cmp.QI53 | HMDB11229 | C38:7 PC plasmalogen | C8-pos | 8.66 | 790.5737 | −4.79042 |
| cmp.QI5421 | | | C8-pos | 9.28 | 808.1368 | −4.76529 |
| QI5991 | | | HIL-pos | 7.74 | 542.3225 | −4.76141 |
| cmp.QI5103 | | | C8-pos | 9.17 | 781.6193 | −4.73766 |
| cmp.QI4789 | | | C8-pos | 8.7 | 751.5456 | −4.71242 |
| QI2981 | | | HIL-pos | 4.25 | 227.0662 | −4.70075 |
| QI2912 | | | C18-neg | 13.37 | 303.2232 | −4.69693 |
| QI1409 | | | HIL-pos | 4.28 | 155.0452 | −4.67547 |
| cmp.QI4890 | | | C8-pos | 9.3 | 762.6555 | −4.67128 |
| QI2503 | | | C18-neg | 1.54 | 265.0415 | −4.66499 |
| cmp.QI2142 | | | C8-pos | 9.28 | 483.8013 | −4.6621 |
| cmp.QI5414 | | | C8-pos | 9.28 | 807.635 | −4.66188 |
| QI6803 | | | C18-neg | 10.39 | 644.2724 | −4.65518 |
| cmp.QI5616 | | | C8-pos | 8.81 | 823.6029 | −4.65245 |
| QI2263 | | | HIL-pos | 1.98 | 193.086 | −4.64556 |
| QI7063 | | | HIL-pos | 5.35 | 774.5429 | −4.63317 |
| QI3208 | | | HIL-pos | 1.94 | 239.0913 | −4.63301 |
| cmp.QI1351 | | | C8-pos | 11.43 | 369.3513 | −4.6131 |
| QI5671 | | | C18-neg | 7.61 | 528.263 | −4.60659 |
| cmp.QI6794 | | | C8-pos | 9.28 | 943.6094 | −4.59928 |
| cmp.QI6867 | | | C8-pos | 9.51 | 957.6259 | −4.59916 |
| QI6551 | | | C18-neg | 10.39 | 600.3299 | −4.5891 |
| cmp.QI2583 | | | C8-pos | 4.43 | 542.3243 | −4.57361 |
| QI5906 | | | C18-neg | 7.59 | 550.2451 | −4.56771 |
| QI1441 | | | C18-neg | 2.38 | 197.0534 | −4.56124 |
| QI6899 | | | HIL-pos | 5.4 | 736.5277 | −4.56079 |
| cmp.QI5243 | | | C8-pos | 8.4 | 794.5675 | −4.52305 |
| cmp.QI5899 | | | C8-pos | 9.12 | 849.6071 | −4.52219 |
| QI2957 | | | HIL-pos | 5.46 | 226.0822 | −4.52023 |
| cmp.QI3478 | | | C8-pos | 4.43 | 632.2935 | −4.51425 |
| QI3209 | | | HIL-pos | 2.02 | 239.0913 | −4.50035 |
| cmp.QI6089 | | | C8-pos | 8.15 | 866.0272 | −4.49616 |
| cmp.QI2788 | | | C8-pos | 4.43 | 564.3061 | −4.48651 |
| QI2501 | | | HIL-pos | 8.2 | 203.1391 | −4.46336 |
| QI3635 | | | HIL-pos | 4.18 | 267.0587 | −4.44863 |
| QI1439 | | | C18-neg | 1 | 197.0534 | −4.4451 |

TABLE 1-continued

| Compound | HMDB ID | Metabolite | Method | RT | m/z | log10_pval |
|---|---|---|---|---|---|---|
| cmp.QI1375 | | | C8-pos | 11.43 | 371.358 | −4.44355 |
| cmp.QI1669 | | | C8-pos | 9.8 | 420.3193 | −4.43035 |
| QI6727 | | | HIL-pos | 2.41 | 694.5801 | −4.42669 |
| cmp.QI5379 | | | C8-pos | 9.93 | 804.7022 | −4.41538 |
| QI5980 | | | HIL-pos | 1.62 | 540.4694 | −4.40271 |
| cmp.QI5863 | | | C8-pos | 8.64 | 846.5394 | −4.40229 |
| cmp.QI4416 | | | C8-pos | 11.43 | 716.6332 | −4.39525 |
| cmp.QI5091 | | | C8-pos | 8.16 | 780.5533 | −4.38584 |
| cmp.QI4987 | | | C8-pos | 9.05 | 771.6365 | −4.35461 |
| QI5128 | | | C18-neg | 12.35 | 479.3375 | −4.34353 |
| cmp.QI7129 | | | C8-pos | 9.27 | 1011.597 | −4.33853 |
| cmp.QI6658 | | | C8-pos | 9.6 | 925.1411 | 4.32408 |
| cmp.QI271 | | C54:9 TAG +NH4 | C8-pos | 10.95 | 890.7247 | −4.31852 |
| cmp.QI1616 | | | C8-pos | 9.28 | 412.3036 | −4.31812 |
| cmp.QI4274 | | | C8-pos | 11.43 | 702.6174 | −4.31754 |
| cmp.QI2787 | | | C8-pos | 4.34 | 564.306 | −4.29495 |
| cmp.QI105 | HMDB12104 | C22:1 SM | C8-pos | 9.28 | 785.653 | −4.28779 |
| cmp.QI5169 | | | C8-pos | 7.91 | 788.5195 | −4.28582 |
| cmp.QI4929 | | | C8-pos | 7.91 | 766.5377 | −4.26937 |
| QI1348 | | | C18-neg | 10.55 | 183.1379 | −4.26748 |
| cmp.TF08 | | C54:10 TAG | C8-pos | 9.8 | 893.6624 | −4.26591 |
| QI5653 | | | C18-neg | 10.39 | 526.293 | −4.26497 |
| cmp.QI5710 | | | C8-pos | 8.17 | 832.5372 | −4.26271 |
| QI6804 | | | C18-neg | 10.6 | 644.273 | −4.26122 |
| QI4176 | | | HIL-pos | 2.5 | 307.2015 | −4.25307 |
| cmp.QI4798 | | | C8-pos | 7.65 | 752.5221 | −4.24859 |
| QI1306 | | | C18-neg | 17.87 | 180.0324 | −4.23561 |
| cmp.QI6058 | | | C8-pos | 10.02 | 863.6975 | −4.23455 |
| cmp.QI82 | | C42:11 PE plasmalogen | C8-pos | 8.79 | 796.5252 | −4.23408 |
| QI5426 | | | HIL-pos | 2.4 | 446.2903 | −4.23177 |
| QI12 | HMDB01999 | Eicosapentaenoic acid | C18-neg | 13.37 | 301.217 | −4.2275 |
| QI1 | HMDB03331 | 1-Methyladenosine | HIL-pos | 7.74 | 282.1195 | −4.2244 |
| cmp.QI1618 | | | C8-pos | 9.28 | 412.8053 | −4.22244 |
| QI2203 | | | HIL-pos | 9.84 | 189.1792 | −4.22121 |
| cmp.QI5670 | | | C8-pos | 10.14 | 829.7158 | −4.22025 |
| QI3536 | | | C18-neg | 2.77 | 339.0395 | −4.21087 |
| QI6198 | | | HIL-pos | 7.72 | 580.2799 | 4.20313 |
| cmp.QI5471 | | | C8-pos | 8.65 | 812.5578 | −4.20248 |
| QI2197 | | | HIL-pos | 9.25 | 189.1346 | −4.19916 |
| cmp.QI2922 | | | C8-pos | 6.17 | 578.4181 | −4.18598 |
| QI6459 | | | HIL-pos | 1.92 | 624.4469 | −4.17876 |
| cmp.QI5002 | | | C8-pos | 10.95 | 773.6192 | −4.17874 |
| QI2186 | | | HIL-pos | 9.84 | 188.1758 | −4.17265 |
| cmp.QI6917 | | | C8-pos | 8.66 | 966.5417 | −4.16998 |
| cmp.QI4734 | | | C8-pos | 8.92 | 745.6208 | −4.16599 |
| QI6739 | | | HIL-pos | 5.48 | 698.512 | −4.16241 |
| QI4244 | | | C18-neg | 2.77 | 413.0439 | −4.1488 |
| QI4191 | | | C18-neg | 2.75 | 407.0268 | −4.14639 |
| QI3811 | | | C18-neg | 13.37 | 369.2042 | −4.14359 |
| QI3157 | | | C18-neg | 2.77 | 323.0746 | −4.14288 |
| cmp.QI2199 | | | C8-pos | 9.79 | 491.3153 | −4.14217 |
| cmp.QI5506 | | | C8-pos | 9.55 | 816.152 | −4.14208 |
| QI3802 | | | HIL-pos | 1.94 | 279.0838 | −4.12668 |
| cmp.QI5682 | | | C8-pos | 8.65 | 830.5662 | −4.12093 |
| cmp.QI5354 | | | C8-pos | 8.17 | 803.037 | −4.10347 |
| QI1652 | | | C18-neg | 2.78 | 211.0968 | −4.09812 |
| cmp.QI5782 | | | C8-pos | 8.16 | 838.6065 | −4.09572 |
| TF84 | HMDB00262 | thymine | HILIC-neg | 1.35 | 125.0357 | −4.0929 |
| QI3080 | | | C18-neg | 13.8 | 315.2326 | −4.08932 |
| QI3908 | | | HIL-pos | 4.33 | 286.1033 | −4.08913 |
| cmp.QI5962 | | | C8-pos | 7.91 | 856.5065 | −4.08404 |
| QI7368 | | | C18-neg | 10.6 | 784.2594 | −4.07063 |
| QI1036 | | | HIL-pos | 5.83 | 139.0503 | −4.07048 |
| QI3061 | | | HIL-pos | 8.63 | 230.1863 | −4.06806 |
| QI3597 | | | C18-neg | 2.77 | 345.0564 | −4.06094 |
| QI6376 | | | HIL-pos | 5.37 | 609.5242 | −4.05505 |
| cmp.QI5655 | | | C8-pos | 9.77 | 827.7002 | −4.05499 |
| QI1672 | | | HIL-pos | 8.69 | 167.0217 | −4.05056 |
| QI2213 | | | HIL-pos | 4.04 | 190.1074 | −4.04841 |
| QI2719 | | | C18-neg | 5.28 | 285.9895 | −4.04789 |
| cmp.QI123 | HMDB06731 | C20:5 CE | C8-pos | 11.43 | 693.5575 | −4.04634 |
| QI6754 | | | C18-neg | 13.38 | 633.4913 | −4.04435 |
| QI2584 | | | C18-neg | 2.79 | 277.0691 | −4.04381 |
| cmp.QI6272 | | | C8-pos | 8.34 | 884.5369 | −4.04345 |
| QI10 | HMDB01182 | 6-8-Dihydroxypurine | HIL-pos | 4.44 | 153.0408 | −4.04208 |
| QI6851 | | | C18-neg | 10.4 | 654.3016 | −4.02843 |
| cmp.QI6096 | | | C8-pos | 8.64 | 866.638 | −4.02405 |
| QI1882 | | | HIL-pos | 7.25 | 175.0714 | −4.02244 |

TABLE 1-continued

| Compound | HMDB ID | Metabolite | Method | RT | m/z | log10_pval |
|---|---|---|---|---|---|---|
| QI2292 | | | HIL-pos | 5.41 | 194.1038 | −4.02124 |
| QI5791 | | | C18-neg | 2.75 | 533.1633 | −4.01738 |
| QI2356 | | | HIL-pos | 4.52 | 198.0431 | −4.01702 |
| cmp.QI5811 | | | C8-pos | 10.02 | 841.7165 | −4.01646 |
| QI590 | | | C18-neg | 17.93 | 134.8933 | −3.99799 |
| QI6919 | | | HIL-pos | 6.59 | 740.5584 | −3.99375 |
| QI1483 | | | HIL-pos | 4.26 | 158.0812 | −3.99353 |
| cmp.QI5493 | | | C8-pos | 8.69 | 814.5707 | −3.98887 |
| QI2268 | | | C18-neg | 2.78 | 255.0871 | −3.98596 |
| QI6080 | | | C18-neg | 10.4 | 576.2855 | −3.98323 |
| QI7155 | | | HIL-pos | 6.54 | 794.5699 | −3.97772 |
| cmp.QI3132 | | | C8-pos | 6.75 | 599.4279 | −3.97402 |
| QI1958 | | | HIL-pos | 2.57 | 179.1068 | −3.96782 |
| QI7133 | | | HIL-pos | 5.34 | 790.5745 | −3.96706 |
| QI7071 | | | C18-neg | 10.6 | 716.2717 | −3.96599 |
| QI3818 | | | HIL-pos | 13.03 | 279.6862 | −3.9495 |
| cmp.QI1601 | | | C8-pos | 8.17 | 409.7538 | −3.94924 |
| cmp.QI3310 | | | C8-pos | 6.98 | 615.4233 | −3.94792 |
| QI2028 | | | C18-neg | 17.93 | 236.0955 | −3.94348 |
| QI6907 | | | C18-neg | 10.59 | 668.317 | −3.9426 |
| QI6346 | | | C18-neg | 10.4 | 586.3141 | −3.92576 |
| QI7411 | | | C18-neg | 10.39 | 790.2769 | −3.91847 |
| QI3581 | | | C18-neg | 1 | 341.9995 | −3.9096 |
| cmp.QI6603 | | | C8-pos | 9.12 | 917.5944 | −3.90761 |
| cmp.QI72 | HMDB11410 | C36:5 PE plasmalogen | C8-pos | 8.74 | 724.5275 | −3.90537 |
| QI130 | HMDB00252 | sphingosine | HIL-pos | 2 | 300.2897 | −3.9052 |
| QI3725 | | | C18-neg | 13.37 | 359.1757 | −3.90454 |
| cmp.QI84 | HMDB12356 | C34:0 PS | C8-pos | 8.16 | 764.5474 | −3.90328 |
| QI7121 | | | C18-neg | 10.6 | 722.2892 | −3.90101 |
| cmp.QI2086 | | | C8-pos | 9.4 | 477.8015 | −3.89446 |
| QI6081 | | | C18-neg | 10.6 | 576.2855 | −3.89255 |
| QI6024 | | | C18-neg | 7.66 | 567.3164 | −3.89224 |
| QI7134 | | | HIL-pos | 6.46 | 790.5745 | −3.89114 |
| QI5310 | | | C18-neg | 13.38 | 505.179 | −3.88671 |
| cmp.QI5376 | | | C8-pos | 8.84 | 804.5877 | −3.88418 |
| QI4456 | | | C18-neg | 13.37 | 437.1915 | −3.86755 |
| cmp.QI6434 | | | C8-pos | 8.65 | 898.5538 | −3.86538 |
| cmp.QI515 | | | C8-pos | 2.9 | 239.0911 | −3.86373 |
| QI2154 | | | HIL-pos | 4.34 | 186.0761 | −3.85969 |
| QI4796 | | | HIL-pos | 7.09 | 364.3092 | −3.84819 |
| QI3092 | | | C18-neg | 11.97 | 317.2125 | −3.84411 |
| QI6850 | | | C18-neg | 10.6 | 654.3015 | −3.83925 |
| QI3962 | | | HIL-pos | 4.23 | 290.1346 | −3.83695 |
| cmp.QI5315 | | | C8-pos | 7.89 | 800.5195 | −3.82735 |
| QI1392 | | | HIL-pos | 4.34 | 154.0612 | −3.82049 |
| cmp.QI6623 | | | C8-pos | 10.15 | 919.6851 | −3.81642 |
| cmp.QI7182 | | | C8-pos | 8.66 | 1034.529 | −3.8158 |
| cmp.QI5233 | | | C8-pos | 8.59 | 793.5909 | −3.81355 |
| cmp.QI2650 | | | C8-pos | 8.95 | 550.2176 | −3.81071 |
| QI2193 | | | C18-neg | 10.55 | 251.1258 | −3.81017 |
| QI1310 | | | C18-neg | 18.61 | 180.0324 | −3.80943 |
| QI7014 | | | HIL-pos | 5.39 | 764.5588 | −3.80107 |
| QI2713 | | | C18-neg | 6.11 | 285.9895 | −3.78106 |
| QI7122 | | | C18-neg | 10.4 | 722.2892 | −3.78102 |
| QI571 | | | HIL-pos | 4.34 | 112.051 | −3.77333 |
| cmp.QI5058 | | | C8-pos | 7.89 | 778.5376 | −3.77137 |
| QI7410 | | | C18-neg | 10.6 | 790.2766 | −3.7585 |
| QI6733 | | | HIL-pos | 2.41 | 696.5959 | −3.75617 |
| QI7183 | | | C18-neg | 10.61 | 736.3046 | −3.75233 |
| cmp.QI4881 | | | C8-pos | 11.44 | 761.545 | −3.74773 |
| QI2913 | | | C18-neg | 13.88 | 303.2325 | −3.74491 |
| cmp.QI5690 | | | C8-pos | 8.65 | 831.0677 | −3.73537 |
| cmp.QI5475 | | | C8-pos | 8.66 | 813.0679 | −3.72835 |
| cmp.QI6920 | | | C8-pos | 11.12 | 966.7535 | −3.72238 |
| QI5962 | | | HIL-pos | 1.61 | 538.4535 | −3.72057 |
| QI5130 | | | HIL-pos | 6.92 | 406.1323 | −3.71929 |
| QI7153 | | | HIL-pos | 6.76 | 794.5671 | −3.71902 |
| cmp.QI5223 | | | C8-pos | 8.69 | 792.5886 | −3.71391 |
| cmp.QI7118 | | | C8-pos | 8.17 | 1006.497 | −3.71343 |
| QI5074 | | | HIL-pos | 2.55 | 397.383 | −3.70816 |
| cmp.QI5063 | | | C8-pos | 9.36 | 778.5745 | −3.70808 |
| QI3986 | | | C18-neg | 9.36 | 386.9171 | −3.70795 |
| QI6623 | | | C18-neg | 8 | 611.3427 | −3.7069 |
| QI7172 | | | C18-neg | 10.6 | 730.2874 | −3.70497 |
| QI964 | | | C18-neg | 1 | 157.0605 | −3.70246 |
| cmp.QI4904 | | | C8-pos | 8.16 | 764.0455 | −3.69774 |
| cmp.QI6807 | | | C8-pos | 10.97 | 945.694 | −3.69165 |
| QI6347 | | | C18-neg | 10.6 | 586.3141 | −3.68799 |

TABLE 1-continued

| Compound | HMDB ID | Metabolite | Method | RT | m/z | log10_pval |
|---|---|---|---|---|---|---|
| cmp.QI5260 | | | C8-pos | 9.18 | 796.1074 | −3.68686 |
| QI5677 | | | C18-neg | 6.97 | 528.2634 | −3.68149 |
| QI6550 | | | C18-neg | 10.6 | 600.3296 | −3.67447 |
| cmp.QI7167 | | | C8-pos | 9.78 | 1027.628 | −3.67413 |
| cmp.QI4565 | | | C8-pos | 13.08 | 729.6517 | −3.66445 |
| QI2605 | | | HIL-pos | 3.46 | 208.064 | −3.66407 |
| cmp.QI4995 | | | C8-pos | 8.85 | 772.5248 | −3.65313 |
| QI3569 | | | C18-neg | 15.46 | 341.197 | −3.65145 |
| cmp.QI4161 | | | C8-pos | 11.13 | 691.5421 | −3.64783 |
| cmp.QI4952 | | | C8-pos | 8.64 | 768.5874 | −3.64065 |
| QI5075 | | | HIL-pos | 2.01 | 397.383 | −3.63977 |
| cmp.QI5539 | | | C8-pos | 8.16 | 818.508 | −3.62931 |
| QI4153 | | | HIL-pos | 4.81 | 305.0855 | −3.62299 |
| cmp.QI4564 | | | C8-pos | 11.43 | 729.6286 | −3.61523 |
| cmp.QI6133 | | | C8-pos | 10.84 | 869.6633 | −3.60997 |
| QI3934 | | | C18-neg | 5.95 | 385.114 | −3.59992 |
| QI1296 | | | HIL-pos | 9.44 | 149.1196 | −3.59572 |
| cmp.QI1693 | | | C8-pos | 8.65 | 423.7695 | −3.59322 |
| QI6938 | | | HIL-pos | 7.1 | 745.6217 | −3.5828 |
| cmp.QI5816 | | | C8-pos | 7.66 | 842.4911 | −3.57702 |
| cmp.QI5978 | | | C8-pos | 9.6 | 857.1532 | −3.56523 |
| QI3646 | | | C18-neg | 13.51 | 347.2102 | −3.5549 |
| cmp.QI6099 | | | C8-pos | 9.95 | 866.6603 | −3.54883 |
| QI5091 | | | C18-neg | 2.77 | 475.014 | −3.53325 |
| QI7143 | | | HIL-pos | 6.46 | 792.5903 | −3.52508 |
| cmp.QI5218 | | | C8-pos | 8.65 | 792.0773 | −3.52105 |
| QI1260 | | | C18-neg | 1 | 175.0712 | −3.51338 |
| QI3707 | | | C18-neg | 2.84 | 355.0125 | −3.50739 |
| cmp.QI5906 | | | C8-pos | 7.97 | 850.5352 | −3.50655 |
| cmp.QI6363 | | | C8-pos | 9.6 | 891.1472 | −3.50284 |
| cmp.QI289 | HMDB10513 | C56:10 TAG | C8-pos | 11.12 | 921.6942 | −3.50237 |
| QI4335 | | | HIL-pos | 7.73 | 320.0754 | −3.49828 |
| cmp.QI6655 | | | C8-pos | 9.6 | 924.6394 | −3.48922 |
| QI3516 | | | HIL-pos | 4.25 | 259.0925 | −3.48866 |
| QI5479 | | | HIL-pos | 1.67 | 455.3731 | −3.47151 |
| cmp.QI4788 | | | C8-pos | 7.38 | 751.4967 | −3.47108 |
| cmp.QI5845 | | | C8-pos | 9.95 | 844.6785 | −3.4701 |
| QI608 | | | C18-neg | 17.74 | 136.8902 | −3.46972 |
| QI6865 | | | C18-neg | 10.6 | 658.2442 | −3.46843 |
| QI2247 | | | HIL-pos | 3.5 | 192.069 | −3.46752 |
| QI3309 | | | C18-neg | 14.37 | 327.2328 | −3.46086 |
| QI5450 | | | C18-neg | 13.28 | 517.389 | −3.45635 |
| QI3302 | | | C18-neg | 8.66 | 327.1636 | −3.44745 |
| cmp.QI6871 | | | C8-pos | 9.58 | 958.6323 | −3.44638 |
| QI2564 | | | C18-neg | 1.04 | 271.9258 | −3.44549 |
| cmp.QI7069 | | | C8-pos | 11.09 | 995.7095 | −3.43497 |
| cmp.QI5244 | | | C8-pos | 8.28 | 794.5703 | −3.43406 |
| QI1071 | | | C18-neg | 16.28 | 162.981 | −3.43233 |
| cmp.QI5524 | | | C8-pos | 8.38 | 817.5565 | −3.43206 |
| QI6644 | | | HIL-pos | 2.41 | 668.5646 | −3.41836 |
| QI6344 | | | C18-neg | 10.5 | 586.3138 | −3.4144 |
| QI931 | | | HIL-pos | 3.75 | 133.0497 | −3.39657 |
| QI6670 | | | HIL-pos | 7.22 | 677.5593 | −3.39569 |
| QI6686 | | | HIL-pos | 2.98 | 682.5613 | −3.39179 |
| QI2776 | | | C18-neg | 3.31 | 291.0832 | −3.39108 |
| QI1448 | | | HIL-pos | 3.57 | 156.102 | −3.38508 |
| QI1976 | | | HIL-pos | 4.73 | 180.0518 | −3.37644 |
| cmp.QI290 | | C56:10 TAG +NH4 | C8-pos | 11.12 | 916.739 | −3.3739 |
| QI5441 | | | C18-neg | 9.87 | 517.1133 | −3.37187 |
| cmp.QI5180 | | | C8-pos | 10.95 | 789.5931 | −3.37122 |
| cmp.QI5613 | | | C8-pos | 9.6 | 823.1596 | −3.36661 |
| cmp.QI6122 | | | C8-pos | 7.89 | 868.5069 | −3.36626 |
| QI6730 | | | HIL-pos | 7.31 | 695.5095 | −3.36328 |
| QI2847 | | | HIL-pos | 4.2 | 223.0714 | −3.36288 |
| cmp.QI106 | HMDB12103 | C22:0 SM | C8-pos | 9.57 | 787.6676 | −3.3613 |
| QI1237 | | | HIL-pos | 3.77 | 147.0765 | −3.35887 |
| QI3490 | | | C18-neg | 2.83 | 335.0279 | −3.35509 |
| QI6345 | | | C18-neg | 10.53 | 586.314 | −3.35497 |
| QI3028 | | | C18-neg | 2.82 | 313.0462 | −3.35124 |
| QI4735 | | | HIL-pos | 5.64 | 358.1708 | −3.34732 |
| QI1936 | | | HIL-pos | 9.43 | 178.0587 | −3.34597 |
| QI4370 | | | C18-neg | 7.28 | 427.1136 | −3.3367 |
| QI3659 | | | C18-neg | 13.85 | 349.2149 | −3.33518 |
| QI5652 | | | C18-neg | 10.6 | 526.2927 | −3.33483 |
| QI4907 | | | C18-neg | 9.38 | 460.9212 | −3.3286 |
| QI60 | HMDB10404 | C22:6 LPC | HIL-pos | 7.6 | 568.3396 | −3.32679 |
| cmp.QI5014 | | | C8-pos | 7.65 | 774.504 | −3.32388 |
| QI189 | | | C18-neg | 1 | 96.9586 | −3.32385 |

TABLE 1-continued

| Compound | HMDB ID | Metabolite | Method | RT | m/z | log10_pval |
|---|---|---|---|---|---|---|
| cmp.QI6320 | | | C8-pos | 11.04 | 887.6521 | −3.3191 |
| QI6545 | | | C18-neg | 1.03 | 600.0618 | −3.31905 |
| QI6059 | | | HIL-pos | 4.02 | 552.0604 | −3.3044 |
| QI5602 | | | HIL-pos | 2.42 | 475.2974 | −3.29928 |
| QI1953 | | | HIL-pos | 2.03 | 179.0704 | −3.2977 |
| QI628 | | | HIL-pos | 3.75 | 115.0506 | −3.29528 |
| QI2651 | | | HIL-pos | 2.52 | 210.1128 | −3.29346 |
| cmp.QI6717 | | | C8-pos | 11.6 | 934.7886 | −3.29262 |
| cmp.QI309 | HMDB10531 | C58:11 TAG | C8-pos | 11.25 | 947.7089 | −3.28907 |
| cmp.QI5800 | | | C8-pos | 9.11 | 840.5879 | −3.28659 |
| QI5936 | | | C18-neg | 10.72 | 553.3252 | −3.28359 |
| cmp.QI1726 | | | C8-pos | 7.26 | 427.2369 | −3.28001 |
| QI5331 | | | C18-neg | 10.72 | 507.3197 | −3.27436 |
| QI2495 | | | C18-neg | 7.03 | 263.6279 | −3.27126 |
| cmp.QI4988 | | | C8-pos | 9 | 771.6379 | −3.26609 |
| QI4419 | | | C18-neg | 13.86 | 434.2306 | −3.26375 |
| QI5126 | | | C18-neg | 10.92 | 479.3371 | −3.26353 |
| QI973 | | | C18-neg | 1.03 | 158.0639 | −3.25001 |
| QI1867 | | | HIL-pos | 3.84 | 174.1126 | −3.24558 |
| QI6262 | | | HIL-pos | 7.52 | 590.3217 | −3.245 |
| cmp.QI310 | HMDB10531 | C58:11 TAG +NH4 | C8-pos | 11.25 | 942.7547 | −3.24171 |
| cmp.QI118 | HMDB00610 | C18:2 CE +NH4 | C8-pos | 11.83 | 666.6182 | −3.24121 |
| QI1319 | | | HIL-pos | 8.69 | 151.0478 | −3.23985 |
| QI2826 | | | HIL-pos | 2.02 | 221.0809 | −3.23914 |
| QI3591 | | | C18-neg | 1 | 343.9945 | −3.23527 |
| QI5110 | | | HIL-pos | 1.72 | 402.2638 | −3.22874 |
| QI6766 | | | HIL-pos | 5.54 | 704.5593 | −3.21814 |
| QI6891 | | | HIL-pos | 5.41 | 734.5119 | −3.21717 |
| QI1025 | | | HIL-pos | 4.41 | 138.0551 | −3.21567 |
| QI4160 | | | HIL-pos | 2 | 305.186 | −3.21564 |
| QI6711 | | | C18-neg | 8.02 | 624.3381 | −3.21486 |
| cmp.QI5283 | | | C8-pos | 8.16 | 798.0388 | −3.21414 |
| QI4237 | | | C18-neg | 1.59 | 411.9823 | −3.21065 |
| cmp.QI5203 | | | C8-pos | 9.71 | 790.6865 | −3.2065 |
| QI4421 | | | C18-neg | 7.3 | 435.1455 | −3.20348 |
| QI4002 | | | HIL-pos | 2 | 293.186 | −3.20171 |
| QI6937 | | | C18-neg | 13.86 | 677.4539 | −3.20055 |
| cmp.QI5004 | | | C8-pos | 9.28 | 773.6529 | −3.20041 |
| QI5064 | | | HIL-pos | 2.56 | 395.3675 | −3.1992 |
| cmp.QI5971 | | | C8-pos | 9.6 | 856.6516 | −3.19405 |
| cmp.QI11 | HMDB10404 | C22:6 LPC | C8-pos | 4.67 | 568.34 | −3.19353 |
| QI6855 | | | HIL-pos | 5.41 | 724.5276 | −3.18714 |
| cmp.QI6605 | | | C8-pos | 9.77 | 917.6698 | −3.18152 |
| cmp.QI5623 | | | C8-pos | 9.79 | 824.1677 | −3.18048 |
| QI5642 | | | HIL-pos | 1.65 | 481.3888 | −3.17854 |
| QI4362 | | | C18-neg | 7.27 | 425.1167 | −3.17731 |
| QI3767 | | | C18-neg | 7.32 | 367.1582 | −3.17669 |
| QI6874 | | | C18-neg | 13.86 | 659.5066 | −3.1765 |
| QI5324 | | | HIL-pos | 1.75 | 432.3114 | −3.17333 |
| QI2518 | | | HIL-pos | 5.53 | 204.0868 | −3.16975 |
| cmp.QI5060 | | | C8-pos | 8.96 | 778.5717 | −3.16898 |
| cmp.QI4185 | | | C8-pos | 11.83 | 694.649 | −3.16307 |
| QI2380 | | | C18-neg | 13.38 | 257.2273 | −3.16118 |
| QI3394 | | | HIL-pos | 3.75 | 251.0776 | −3.16046 |
| QI5650 | | | C18-neg | 6.95 | 526.2483 | −3.15644 |
| QI2656 | | | C18-neg | 13.87 | 283.2427 | −3.15438 |
| QI2517 | | | HIL-pos | 1.63 | 204.0868 | −3.15339 |
| cmp.QI5571 | | | C8-pos | 8.62 | 820.5837 | −3.15158 |
| cmp.QI4909 | | | C8-pos | 8.72 | 764.5564 | −3.14943 |
| QI1151 | | | HIL-pos | 3.46 | 144.0656 | −3.14935 |
| QI4105 | | | C18-neg | 13.86 | 395.2197 | −3.14544 |
| cmp.QI108 | HMDB11697 | C24:0 SM | C8-pos | 9.99 | 815.6999 | −3.14441 |
| QI3939 | | | C18-neg | 13.86 | 385.191 | −3.14212 |
| cmp.QI5703 | | | C8-pos | 8.15 | 832.034 | −3.13916 |
| cmp.QI4748 | | | C8-pos | 8.74 | 746.5101 | −3.13771 |
| cmp.QI5195 | | | C8-pos | 8.2 | 790.5351 | −3.13767 |
| cmp.QI4412 | | | C8-pos | 8.26 | 716.5575 | −3.13559 |
| QI6360 | | | HIL-pos | 7.63 | 606.2956 | −3.13448 |
| QI6460 | | | HIL-pos | 2.27 | 624.4469 | −3.13288 |
| cmp.QI1950 | | | C8-pos | 8.29 | 456.75 | −3.12666 |
| cmp.QI1698 | | | C8-pos | 8.65 | 424.2713 | −3.1257 |
| QI5290 | | | C18-neg | 7.29 | 503.1328 | −3.12248 |
| QI6726 | | | HIL-pos | 1.99 | 694.58 | −3.11773 |
| cmp.QI5062 | | | C8-pos | 9.23 | 778.5743 | −3.11759 |
| QI5848 | | | HIL-pos | 1.73 | 519.1287 | −3.11333 |
| cmp.QI5515 | | | C8-pos | 9.56 | 816.6475 | −3.11225 |
| QI2266 | | | C18-neg | 1 | 255.0595 | −3.11192 |
| cmp.QI3025 | | | C8-pos | 4.67 | 590.3215 | −3.11134 |

TABLE 1-continued

| Compound | HMDB ID | Metabolite | Method | RT | m/z | log10_pval |
|---|---|---|---|---|---|---|
| cmp.QI1341 | | | C8-pos | 11.52 | 367.3357 | −3.10709 |
| QI4879 | | | HIL-pos | 7.06 | 371.8188 | −3.10653 |
| QI3344 | | | HIL-pos | 3.73 | 247.0924 | −3.10369 |
| cmp.QI4267 | | | C8-pos | 10 | 702.2849 | −3.09838 |
| QI7003 | | | HIL-pos | 5.37 | 762.5431 | −3.09665 |
| QI2580 | | | C18-neg | 12.86 | 275.2015 | −3.08367 |
| QI4176 | | | C18-neg | 12.34 | 403.1322 | −3.08304 |
| QI5755 | | | C18-neg | 1.54 | 529.952 | −3.08241 |
| QI3138 | | | C18-neg | 1.37 | 321.062 | −3.08062 |
| cmp.QI54 | HMDB11319 | C38:6 PC plasmalogen | C8-pos | 8.85 | 792.5884 | −3.07694 |
| cmp.QI4052 | | | C8-pos | 7.37 | 683.5096 | −3.06713 |
| cmp.QI270 | HMDB10498 | C54:9 TAG | C8-pos | 10.95 | 895.679 | −3.06095 |
| QI6786 | | | C18-neg | 5.41 | 640.3332 | −3.05863 |
| QI3347 | | | C18-neg | 13.87 | 330.2411 | −3.05569 |
| QI4256 | | | C18-neg | 6.58 | 413.2001 | −3.0554 |
| cmp.QI1205 | | | C8-pos | 7.35 | 350.2408 | −3.0521 |
| QI4124 | | | C18-neg | 7.66 | 397.205 | −3.0497 |
| QI3666 | | | C18-neg | 9.04 | 350.2099 | −3.04669 |
| QI6039 | | | C18-neg | 11.3 | 568.3394 | −3.04547 |
| QI4177 | | | HIL-pos | 2 | 307.2016 | −3.04358 |
| QI2775 | | | C18-neg | 3.6 | 291.0832 | −3.04339 |
| cmp.QI6900 | | | C8-pos | 11.25 | 963.6834 | −3.03887 |
| cmp.QI4345 | | | C8-pos | 11.43 | 709.5314 | −3.03165 |
| QI3325 | | | C18-neg | 1 | 329.0295 | −3.02425 |
| QI3431 | | | C18-neg | 1.38 | 331.091 | −3.02022 |
| cmp.QI6944 | | | C8-pos | 11.12 | 971.7095 | −3.01485 |
| QI6746 | | | HIL-pos | 7.24 | 699.5437 | −3.01213 |
| TF85 | HMDB00929 | tryptophan | HILIC-neg | 3.35 | 203.0826 | −3.01176 |
| QI2478 | | | C18-neg | 1.38 | 263.1035 | −3.00844 |
| QI6418 | | | C18-neg | 8.69 | 589.2987 | −3.00839 |
| cmp.QI3800 | | | C8-pos | 7.37 | 661.5277 | −3.00404 |
| QI1362 | | | HIL-pos | 5.96 | 153.0581 | −3.00209 |
| QI1725 | | | HIL-pos | 9.45 | 169.0948 | −2.99896 |
| QI7004 | | | HIL-pos | 7.07 | 762.646 | −2.99737 |
| cmp.QI6962 | | | C8-pos | 11.52 | 975.7404 | −2.98608 |
| cmp.QI5207 | | | C8-pos | 8.15 | 791.0369 | −2.98348 |
| QI5855 | | | C18-neg | 1.25 | 541.0361 | −2.98087 |
| QI3592 | | | C18-neg | 7.26 | 344.1567 | −2.98071 |
| QI7073 | | | HIL-pos | 7.05 | 776.662 | −2.97818 |
| QI15 | HMDB02183 | Docosahexaenoic acid | C18-neg | 13.86 | 327.2328 | −2.9768 |
| QI7477 | | | C18-neg | 17.76 | 814.5162 | −2.97475 |
| QI6749 | | | HIL-pos | 2.97 | 700.572 | −2.9745 |
| cmp.QI6289 | | | C8-pos | 9.79 | 885.6362 | −2.97317 |
| cmp.QI6622 | | | C8-pos | 10.88 | 919.6791 | −2.97265 |
| cmp.QI5889 | | | C8-pos | 9.07 | 848.6154 | −2.97253 |
| QI2583 | | | C18-neg | 1 | 277.0414 | −2.97143 |
| QI6853 | | | C18-neg | 13.86 | 655.4722 | −2.96685 |
| QI541 | | | HIL-pos | 9.42 | 110.0717 | −2.96598 |
| QI553 | | | C18-neg | 1 | 131.0812 | −2.96124 |
| QI7048 | | | C18-neg | 1.08 | 710.9785 | −2.95902 |
| QI6765 | | | HIL-pos | 6.69 | 704.5587 | −2.95872 |
| cmp.QI5757 | | | C8-pos | 8.4 | 836.0379 | −2.95852 |
| QI7361 | | | C18-neg | 11.04 | 782.3082 | −2.95796 |
| cmp.QI6251 | | | C8-pos | 8.13 | 882.521 | −2.95539 |
| QI1221 | | | C18-neg | 1.16 | 171.0762 | −2.9523 |
| cmp.QI4820 | | | C8-pos | 8.54 | 754.5738 | −2.94555 |
| cmp.QI3984 | | | C8-pos | 7.84 | 677.5588 | −2.94062 |
| cmp.QI6549 | | | C8-pos | 10.94 | 911.6523 | −2.93833 |
| cmp.QI6006 | | | C8-pos | 8.38 | 860.0368 | −2.93432 |
| cmp.QI80 | HMDB11384 | C38:3 PE plasmalogen | C8-pos | 8.95 | 756.5903 | −2.93356 |
| QI4975 | | | C18-neg | 13.86 | 463.2073 | −2.93066 |
| cmp.QI3897 | | | C8-pos | 7.09 | 669.4938 | −2.9305 |
| QI6844 | | | HIL-pos | 7.11 | 719.607 | −2.92917 |
| QI6576 | | | C18-neg | 16.28 | 605.4049 | −2.92907 |
| cmp.QI6265 | | | C8-pos | 11.03 | 883.6784 | −2.92499 |
| QI2516 | | | HIL-pos | 1.75 | 204.0868 | −2.92239 |
| QI5330 | | | HIL-pos | 1.66 | 433.3638 | −2.91825 |
| cmp.QI5442 | | | C8-pos | 9.57 | 809.6504 | −2.91516 |
| QI2506 | | | C18-neg | 1.39 | 265.1089 | −2.91248 |
| QI6689 | | | HIL-pos | 7.31 | 683.5095 | −2.91144 |
| cmp.QI1190 | | | C8-pos | 5.3 | 346.2739 | −2.90524 |
| QI1932 | | | HIL-pos | 1.72 | 177.1638 | −2.90416 |
| QI833 | | | HIL-pos | 3.59 | 128.0708 | −2.89944 |
| QI2659 | | | HIL-pos | 3.75 | 211.0716 | −2.89505 |
| QI3523 | | | C18-neg | 8.21 | 337.1674 | −2.89479 |
| QI5046 | | | HIL-pos | 5.54 | 393.2401 | −2.89456 |
| cmp.QI5927 | | | C8-pos | 8.19 | 852.5511 | −2.89298 |
| QI983 | | | C18-neg | 5.32 | 158.9772 | −2.88778 |

TABLE 1-continued

| Compound | HMDB ID | Metabolite | Method | RT | m/z | log10_pval |
|---|---|---|---|---|---|---|
| cmp.QI6218 | | | C8-pos | 9.56 | 877.6379 | −2.88728 |
| QI7179 | | | HIL-pos | 7.08 | 797.5932 | −2.88688 |
| cmp.QI5681 | | | C8-pos | 8.51 | 830.566 | −2.88002 |
| QI3741 | | | C18-neg | 13.86 | 363.2089 | −2.87792 |
| QI1995 | | | C18-neg | 1.92 | 230.9963 | −2.8774 |
| QI2031 | | | C18-neg | 18.6 | 236.0955 | −2.87587 |
| QI769 | | | C18-neg | 1.38 | 145.0605 | −2.87376 |
| cmp.QI6460 | | | C8-pos | 9.61 | 902.2303 | −2.87086 |
| cmp.QI1213 | | | C8-pos | 5.3 | 351.2293 | −2.87004 |
| QI5759 | | | C18-neg | 1.7 | 529.9523 | −2.86496 |
| QI6704 | | | HIL-pos | 7.25 | 687.5436 | −2.86196 |
| QI5188 | | | HIL-pos | 1.75 | 414.3003 | −2.85929 |
| cmp.QI4016 | | | C8-pos | 11.83 | 680.6333 | −2.85917 |
| QI4887 | | | HIL-pos | 1.99 | 372.2898 | −2.85548 |
| QI968 | | | C18-neg | 1.18 | 157.0857 | −2.8542 |
| QI605 | | | C18-neg | 18.65 | 135.9696 | −2.85114 |
| QI3960 | | | C18-neg | 7.37 | 386.9168 | −2.85012 |
| cmp.QI7057 | | | C8-pos | 11.25 | 992.769 | −2.85006 |
| cmp.QI2589 | | | C8-pos | 7.36 | 543.4185 | −2.84958 |
| cmp.QI5771 | | | C8-pos | 9.99 | 837.6817 | −2.84837 |
| QI6710 | | | HIL-pos | 7.62 | 690.2564 | −2.84515 |
| QI1320 | | | C18-neg | 17.94 | 180.9882 | −2.84235 |
| QI4148 | | | C18-neg | 1.38 | 399.0781 | −2.84228 |
| QI4364 | | | C18-neg | 8.66 | 425.2002 | −2.83893 |
| cmp.QI5677 | | | C8-pos | 9.77 | 830.1675 | −2.83757 |
| QI3340 | | | C18-neg | 8.5 | 329.2332 | −2.83666 |
| QI3610 | | | C18-neg | 12.86 | 345.2432 | −2.83207 |
| cmp.QI5969 | | | C8-pos | 8.34 | 856.5849 | −2.83086 |
| QI4427 | | | C18-neg | 2.78 | 436.8765 | −2.83004 |
| QI1865 | | | HIL-pos | 3.19 | 174.0762 | −2.82974 |
| cmp.QI5076 | | | C8-pos | 9.15 | 779.5763 | −2.82668 |
| QI3336 | | | C18-neg | 8.77 | 329.233 | −2.82507 |
| QI7079 | | | HIL-pos | 6.57 | 778.5382 | −2.8235 |
| QI7205 | | | C18-neg | 11.21 | 742.2872 | −2.82239 |
| QI3805 | | | C18-neg | 7.56 | 369.1738 | −2.82202 |
| QI7081 | | | C18-neg | 15.7 | 717.5182 | −2.82105 |
| QI2283 | | | C18-neg | 14.37 | 255.2325 | −2.819 |
| cmp.QI1632 | | | C8-pos | 9.57 | 413.8131 | −2.81591 |
| QI4232 | | | C18-neg | 1.75 | 411.9822 | −2.8071 |
| QI3310 | | | C18-neg | 14.21 | 327.2329 | −2.80458 |
| cmp.QI3674 | | | C8-pos | 11.84 | 649.5916 | −2.80411 |
| QI4234 | | | C18-neg | 1.34 | 411.9822 | −2.80363 |
| cmp.QI4272 | | | C8-pos | 7.42 | 702.5067 | −2.80355 |
| cmp.QI3927 | | | C8-pos | 9.84 | 672.6249 | −2.80259 |
| cmp.QI6528 | | | C8-pos | 9.11 | 908.575 | −2.80151 |
| QI493 | | | HIL-pos | 5.61 | 106.0503 | −2.80079 |
| QI7005 | | | HIL-pos | 7 | 762.6565 | −2.80004 |
| QI3325 | | | HIL-pos | 8.28 | 246.0909 | −2.79858 |
| cmp.QI3649 | | | C8-pos | 7.1 | 647.5121 | −2.79739 |
| QI6135 | | | HIL-pos | 1.77 | 568.4276 | −2.79669 |
| QI6933 | | | HIL-pos | 7.1 | 743.6061 | −2.79617 |
| QI1933 | | | HIL-pos | 2 | 177.1639 | −2.79611 |
| QI96 | HMDB00177 | histidine | HIL-pos | 9.42 | 156.0768 | −2.79422 |
| QI107 | | | C18-neg | 18.97 | 84.0075 | −2.79392 |
| QI4450 | | | C18-neg | 6.29 | 437.106 | −2.7936 |
| QI4699 | | | HIL-pos | 4.52 | 354.279 | −2.79326 |
| QI6826 | | | HIL-pos | 7.17 | 715.5743 | −2.78927 |
| QI6491 | | | C18-neg | 8.9 | 595.3492 | −2.78829 |
| cmp.QI5551 | | | C8-pos | 8.59 | 819.0672 | −2.78815 |
| cmp.QI5385 | | | C8-pos | 8.4 | 805.0525 | −2.78667 |
| QI2800 | | | C18-neg | 11.8 | 293.212 | −2.78662 |
| QI3654 | | | C18-neg | 1.01 | 348.9981 | −2.78386 |
| QI4516 | | | HIL-pos | 4.41 | 338.057 | −2.7794 |
| QI7518 | | | C18-neg | 17.73 | 824.5438 | −2.77552 |
| cmp.QI5329 | | | C8-pos | 11.83 | 801.531 | −2.77383 |
| QI5105 | | | C18-neg | 13.86 | 477.2223 | −2.77316 |
| QI879 | | | HIL-pos | 9.44 | 130.0865 | −2.76221 |
| QI1847 | | | HIL-pos | 2.55 | 173.1174 | −2.75748 |
| cmp.QI3671 | | | C8-pos | 7.34 | 649.5276 | −2.7549 |
| QI1455 | | | HIL-pos | 9.42 | 157.0802 | −2.7519 |
| cmp.QI1352 | | | C8-pos | 11.83 | 369.3514 | −2.75033 |
| cmp.QI6955 | | | C8-pos | 9.99 | 973.6566 | −2.74932 |
| QI4173 | | | C18-neg | 2.78 | 403.0149 | −2.7493 |
| cmp.QI4649 | | | C8-pos | 7.1 | 737.4813 | −2.74827 |
| QI2873 | | | C18-neg | 16.36 | 297.2795 | −2.74722 |
| QI3029 | | | C18-neg | 2.84 | 313.0463 | −2.74643 |
| cmp.QI1661 | | | C8-pos | 9.51 | 419.3122 | −2.7462 |
| QI5947 | | | HIL-pos | 1.66 | 536.4359 | −2.74533 |

TABLE 1-continued

| Compound | HMDB ID | Metabolite | Method | RT | m/z | log10_pval |
|---|---|---|---|---|---|---|
| QI4208 | | | C18-neg | 13.86 | 409.2354 | −2.74286 |
| cmp.QI34 | HMDB07991 | C38:6 PC | C8-pos | 8.38 | 806.5686 | −2.74061 |
| QI5481 | | | C18-neg | 6.2 | 520.9094 | −2.74016 |
| QI4826 | | | HIL-pos | 1.67 | 367.3574 | −2.73687 |
| cmp.QI41 | HMDB11214 | C34:5 PC plasmalogen | C8-pos | 8.97 | 738.5433 | −2.73647 |
| cmp.QI331 | | | C8-pos | 11.83 | 203.1794 | −2.7358 |
| QI1271 | | | HIL-pos | 9.44 | 148.1161 | −2.73321 |
| cmp.QI6091 | | | C8-pos | 8.24 | 866.5215 | −2.73228 |
| cmp.QI4226 | | | C8-pos | 10.12 | 698.642 | −2.72889 |
| QI6348 | | | C18-neg | 10.8 | 586.3145 | −2.72849 |
| QI669 | | | C18-neg | 17.6 | 141.0156 | −2.72724 |
| QI4262 | | | C18-neg | 6.18 | 415.1243 | −2.72634 |
| QI1661 | | | C18-neg | 5.21 | 213.0218 | −2.72607 |
| QI2155 | | | HIL-pos | 5.53 | 186.0762 | −2.7253 |
| QI6985 | | | HIL-pos | 7.06 | 757.6216 | −2.72513 |
| QI7593 | | | C18-neg | 17.84 | 838.5601 | −2.72504 |
| cmp.QI6906 | | | C8-pos | 8.38 | 964.5255 | −2.72123 |
| QI2696 | | | C18-neg | 5.37 | 285.9894 | −2.71782 |
| QI4006 | | | C18-neg | 1.37 | 389.0498 | −2.71565 |
| QI4095 | | | HIL-pos | 2.42 | 300.2897 | −2.70929 |
| QI6595 | | | HIL-pos | 1.58 | 656.5247 | −2.70783 |
| QI309 | | | HIL-pos | 9.44 | 84.0815 | −2.70397 |
| cmp.QI6537 | | | C8-pos | 11.18 | 909.6936 | −2.69892 |
| QI899 | | | HIL-pos | 9.44 | 131.0898 | −2.69853 |
| cmp.QI4725 | | | C8-pos | 8.74 | 744.5891 | −2.68943 |
| cmp.QI6076 | | | C8-pos | 10.84 | 864.7083 | −2.68843 |
| QI6799 | | | HIL-pos | 7.26 | 711.5406 | −2.68481 |
| cmp.QI1691 | | | C8-pos | 8.38 | 423.2633 | −2.68246 |
| QI805 | | | HIL-pos | 4.55 | 126.0222 | −2.68126 |
| QI4740 | | | HIL-pos | 1.71 | 358.2952 | −2.67933 |
| QI6882 | | | C18-neg | 14.22 | 661.5228 | −2.67682 |
| QI7008 | | | HIL-pos | 7.31 | 763.497 | −2.67649 |
| cmp.QI2843 | | | C8-pos | 4.81 | 570.3552 | −2.67588 |
| QI3512 | | | HIL-pos | 5.67 | 258.2176 | −2.67499 |
| cmp.QI5490 | | | C8-pos | 8.14 | 814.5354 | −2.67238 |
| QI554 | | | C18-neg | 1 | 132.0288 | −2.67058 |
| QI209 | | | C18-neg | 18.94 | 98.9542 | −2.66711 |
| QI3015 | | | C18-neg | 9.87 | 311.2229 | −2.66595 |
| QI6156 | | | HIL-pos | 1.73 | 573.4659 | −2.66375 |
| cmp.QI6716 | | | C8-pos | 11.71 | 934.7867 | −2.66236 |
| cmp.QI1200 | | | C8-pos | 5.49 | 348.2895 | −2.66159 |
| QI3233 | | | HIL-pos | 3.9 | 241.0931 | −2.66157 |
| QI5758 | | | C18-neg | 1.58 | 529.9523 | −2.66132 |
| cmp.QI5007 | | | C8-pos | 8.72 | 774.0611 | −2.66094 |
| cmp.QI3043 | | | C8-pos | 4.81 | 592.3372 | −2.66079 |
| QI6660 | | | HIL-pos | 7.29 | 673.5276 | −2.65849 |
| QI103 | HMDB00182 | lysine | HIL-pos | 9.44 | 147.1128 | −2.65812 |
| cmp.QI5714 | | | C8-pos | 8.33 | 832.5843 | −2.65808 |
| QI4846 | | | C18-neg | 13.77 | 455.4102 | −2.6562 |
| QI4354 | | | C18-neg | 13.85 | 423.2205 | −2.65614 |
| QI4453 | | | C18-neg | 7.56 | 437.1612 | −2.65591 |
| QI6817 | | | C18-neg | 6.63 | 646.3203 | −2.65473 |
| QI4174 | | | C18-neg | 2.84 | 403.0153 | −2.65075 |
| QI858 | | | HIL-pos | 9.44 | 129.1025 | −2.64637 |
| QI4851 | | | C18-neg | 1.37 | 457.0367 | −2.64578 |
| QI518 | | | C18-neg | 1.37 | 127.0499 | −2.64564 |
| QI2433 | | | C18-neg | 1.32 | 259.0133 | −2.64508 |
| QI4428 | | | HIL-pos | 5.65 | 330.1395 | −2.64109 |
| QI6770 | | | HIL-pos | 7.47 | 705.9492 | −2.63862 |
| QI7164 | | | HIL-pos | 7.05 | 795.6353 | −2.63621 |
| cmp.QI7068 | | | C8-pos | 11.51 | 994.7853 | −2.6358 |
| cmp.QI6414 | | | C8-pos | 8.38 | 896.5381 | −2.63423 |
| cmp.QI2821 | | | C8-pos | 4.57 | 568.3402 | −2.63214 |
| cmp.QI5943 | | | C8-pos | 8.19 | 854.5681 | −2.63006 |
| QI1077 | | | HIL-pos | 3.18 | 141.0183 | −2.62678 |
| QI1214 | | | HIL-pos | 3.51 | 146.0812 | −2.62599 |
| QI2837 | | | HIL-pos | 5.55 | 222.0971 | −2.62405 |
| QI1027 | | | HIL-pos | 4.63 | 138.0911 | −2.62157 |
| QI1438 | | | C18-neg | 2.05 | 197.0533 | −2.61617 |
| QI2286 | | | HIL-pos | 3.22 | 194.0483 | −2.61484 |
| QI3026 | | | HIL-pos | 3.75 | 229.0819 | −2.61119 |
| cmp.QI632 | | | C8-pos | 11.83 | 259.2419 | −2.61031 |

(HMDB ID: Human Metabolome Database ID,
Method: LC-MS method where the metabolite was measured,
RT: Retention Time,
m/z: mass over charge,
log10_pval: Logarithm of the p value measuring association with all-cause mortality.)

Example 7: Data Cleaning—Second Example

The data cleaning methods in Example 6 can be repeated with many variations. As a more permissive method of data cleaning, the procedure in Example 6 was repeated setting missingness=0.25 and CV=1.0. At a false discovery rate of 5%, 717 metabolites were identified to associate significantly with all-cause mortality (Table 2).

TABLE 2

(HMDB ID: Human Metabolome Database ID, Method: LC-MS method where the metabolite was measured, RT: Retention Time, m/z: mass over charge, log10_pval: Logarithm of the p value measuring association with all-cause mortality.)

| Compound | HMDB ID | Metabolite | Method | RT | m/z | log10_pval |
|---|---|---|---|---|---|---|
| QI1972 | | | HIL-pos | 7.71 | 179.9824 | −8.5663 |
| QI11 | HMDB01906 | alpha-Aminoisobutyric acid | HIL-pos | 7.71 | 104.0711 | −8.0568 |
| QI3594 | | | HIL-pos | 8.63 | 264.1191 | −7.96361 |
| QI1322 | | | HIL-pos | 4.84 | 151.0615 | −7.72731 |
| QI3862 | | | HIL-pos | 4.82 | 283.1036 | −7.62064 |
| QI3933 | | | HIL-pos | 10.37 | 287.2442 | −7.4685 |
| cmp.QI2854 | | | C8-pos | 9.98 | 571.4876 | −7.41949 |
| QI4231 | | | HIL-pos | 5.41 | 312.1301 | −7.27946 |
| QI6954 | | | HIL-pos | 5.38 | 750.5432 | −7.14147 |
| cmp.QI77 | HMDB11420 | C38:7 PE plasmalogen | C8-pos | 8.67 | 748.5273 | −7.03813 |
| cmp.QI2813 | | | C8-pos | 9.67 | 567.4562 | −7.00079 |
| cmp.QI78 | HMDB11387 | C38:6 PE plasmalogen | C8-pos | 8.86 | 750.5431 | −6.76089 |
| cmp.QI4994 | | | C8-pos | 8.93 | 772.5239 | −6.67176 |
| cmp.QI2812 | | | C8-pos | 10.18 | 567.4561 | −6.62129 |
| cmp.QI2539 | | | C8-pos | 10.18 | 536.4373 | −6.53493 |
| QI6045 | | | HIL-pos | 1.65 | 550.4173 | −6.53367 |
| QI2665 | | | C18-neg | 1.01 | 283.9941 | −6.49773 |
| QI2020 | | | HIL-pos | 7.7 | 181.9804 | −6.47327 |
| cmp.QI6054 | | | C8-pos | 9.4 | 863.6231 | −6.39254 |
| cmp.QI3122 | | | C8-pos | 10.18 | 598.4733 | −6.36237 |
| cmp.QI2531 | | | C8-pos | 10.18 | 535.43 | −6.26371 |
| cmp.QI3406 | | | C8-pos | 9.96 | 625.4955 | −6.20528 |
| QI6382 | | | HIL-pos | 1.99 | 610.4678 | −6.15552 |
| cmp.QI3377 | | | C8-pos | 10.18 | 621.464 | −6.14621 |
| cmp.QI4972 | | | C8-pos | 8.67 | 770.5091 | −6.07414 |
| cmp.QI81 | HMDB11394 | C40:7 PE plasmalogen | C8-pos | 9.11 | 776.5583 | −6.02322 |
| QI5699 | | | HIL-pos | 2.39 | 491.3481 | −6.021 |
| cmp.QI6144 | | | C8-pos | 8.17 | 870.5224 | −5.99375 |
| QI7061 | | | HIL-pos | 7.04 | 773.6531 | −5.89817 |
| QI6994 | | | HIL-pos | 7.06 | 759.6373 | −5.848 |
| cmp.QI6343 | | | C8-pos | 9.5 | 889.6382 | −5.84128 |
| QI6945 | | | HIL-pos | 5.39 | 748.5274 | −5.7981 |
| cmp.QI3104 | | | C8-pos | 10.18 | 597.4667 | −5.74353 |
| cmp.QI5061 | | | C8-pos | 8.65 | 778.5737 | −5.73154 |
| cmp.QI5172 | | | C8-pos | 8.5 | 788.5561 | −5.7246 |
| QI1093 | | | C18-neg | 9.01 | 163.0751 | −5.72018 |
| QI2606 | | | HIL-pos | 5.47 | 208.072 | −5.71115 |
| QI6064 | | | HIL-pos | 1.65 | 552.433 | −5.70657 |
| cmp.QI5003 | | | C8-pos | 9.4 | 773.6529 | −5.69841 |
| QI7070 | | | HIL-pos | 5.35 | 776.5589 | −5.69011 |
| cmp.QI2203 | | | C8-pos | 9.78 | 491.8171 | −5.68964 |
| cmp.QI6754 | | | C8-pos | 8.17 | 938.5102 | −5.65111 |
| cmp.QI5286 | | | C8-pos | 9.11 | 798.5405 | −5.62842 |
| cmp.QI5307 | | | C8-pos | 9.5 | 799.6687 | −5.61567 |
| QI7056 | | | HIL-pos | 5.36 | 772.5265 | −5.59774 |
| cmp.QI5917 | | | C8-pos | 9.32 | 851.6254 | −5.58318 |
| cmp.QI4470 | | | C8-pos | 8.46 | 722.5103 | −5.56929 |
| QI6146 | | | HIL-pos | 1.61 | 570.4433 | −5.56864 |
| cmp.QI47 | HMDB11221 | C36:5 PC plasmalogen-A | C8-pos | 8.49 | 766.5733 | −5.56574 |
| cmp.QI1603 | | | C8-pos | 8.17 | 410.2556 | −5.50011 |
| QI7082 | | | HIL-pos | 6.48 | 778.5742 | −5.46896 |
| cmp.QI5348 | | | C8-pos | 8.16 | 802.5349 | −5.44906 |
| cmp.QI5567 | | | C8-pos | 9.11 | 820.5228 | −5.4403 |
| QI6850 | | | HIL-pos | 5.41 | 722.5118 | −5.39814 |
| QI3235 | | | HIL-pos | 2.05 | 241.096 | −5.39622 |
| QI7013 | | | HIL-pos | 6.51 | 764.5587 | −5.37645 |
| QI2622 | | | HIL-pos | 4.28 | 209.0558 | −5.31253 |
| cmp.QI5335 | | | C8-pos | 9.78 | 801.6843 | −5.30718 |
| cmp.QI6367 | | | C8-pos | 9.78 | 891.6537 | −5.28839 |
| QI3236 | | | HIL-pos | 2.11 | 241.0962 | −5.27147 |
| cmp.QI5590 | | | C8-pos | 9.5 | 821.6505 | −5.26914 |
| cmp.QI38 | HMDB08511 | C40:10 PC | C8-pos | 8.05 | 826.5353 | −5.26873 |
| QI123 | HMDB00767 | Pseudouridine | HIL-pos | 4.28 | 245.0768 | −5.26553 |
| QI3323 | | | HIL-pos | 4.28 | 246.0801 | −5.24295 |
| QI2497 | | | C18-neg | 7.6 | 264.1294 | −5.21814 |
| QI569 | | | HIL-pos | 5.45 | 112.0509 | −5.20531 |
| cmp.QI4910 | | | C8-pos | 8.46 | 764.5566 | −5.19519 |
| QI5268 | | | C18-neg | 10.82 | 498.32 | −5.13512 |

TABLE 2-continued (HMDB ID: Human Metabolome Database ID, Method: LC-MS method
where the metabolite was measured, RT: Retention Time, m/z: mass over charge, log10_pval:
Logarithm of the p value measuring association with all-cause mortality.)

| Compound | HMDB ID | Metabolite | Method | RT | m/z | log10_pval |
| --- | --- | --- | --- | --- | --- | --- |
| TF42 | HMDB00127 | glucuronate | HILIC-neg | 5 | 193.0354 | −5.12363 |
| QI2222 | | | HIL-pos | 4.29 | 191.0452 | −5.11707 |
| cmp.QI4090 | | | C8-pos | 11.13 | 686.5867 | −5.10645 |
| cmp.QI5016 | | | C8-pos | 8.79 | 774.542 | −5.08479 |
| cmp.QI1672 | | | C8-pos | 9.78 | 420.821 | −5.07407 |
| QI7053 | | | C18-neg | 10.59 | 712.2604 | −5.06338 |
| QI1952 | | | HIL-pos | 4.28 | 179.0451 | −5.04837 |
| cmp.QI6202 | | | C8-pos | 9.28 | 875.6222 | −5.03076 |
| cmp.QI6398 | | | C8-pos | 8.05 | 894.5228 | −4.99605 |
| QI6939 | | | HIL-pos | 5.4 | 746.5112 | −4.97243 |
| QI3522 | | | C18-neg | 8.35 | 337.1661 | −4.96501 |
| cmp.QI104 | HMDB12102 | C20:0 SM | C8-pos | 9.17 | 759.6373 | −4.94598 |
| QI6145 | | | HIL-pos | 1.73 | 570.4427 | −4.94274 |
| cmp.QI6878 | | | C8-pos | 9.79 | 959.6415 | −4.9411 |
| QI7055 | | | HIL-pos | 7.04 | 771.6373 | −4.9259 |
| QI2265 | | | HIL-pos | 2.02 | 193.0862 | −4.92117 |
| cmp.QI5316 | | | C8-pos | 9.23 | 800.556 | −4.91448 |
| QI2494 | | | C18-neg | 7.6 | 263.6279 | −4.89983 |
| cmp.QI5667 | | | C8-pos | 7.95 | 829.5552 | −4.89063 |
| cmp.QI3920 | | | C8-pos | 11.43 | 671.5757 | −4.86444 |
| QI5592 | | | HIL-pos | 1.99 | 473.3263 | −4.86357 |
| cmp.QI5618 | | | C8-pos | 9.78 | 823.6661 | −4.82324 |
| cmp.QI124 | HMDB06731 | C20:5 CE +NH4 | C8-pos | 11.43 | 688.6025 | −4.81632 |
| QI5948 | | | HIL-pos | 1.59 | 536.4381 | −4.80293 |
| TF35 | HMDB01999 | eicosapentaenoic acid | HILIC-neg | 3.1 | 301.2173 | −4.80241 |
| cmp.QI53 | HMDB11229 | C38:7 PC plasmalogen | C8-pos | 8.66 | 790.5737 | −4.79042 |
| cmp.QI5421 | | | C8-pos | 9.28 | 808.1368 | −4.76529 |
| QI5991 | | | HIL-pos | 7.74 | 542.3225 | −4.76141 |
| cmp.QI5103 | | | C8-pos | 9.17 | 781.6193 | −4.73766 |
| cmp.QI4789 | | | C8-pos | 8.7 | 751.5456 | −4.71242 |
| QI2981 | | | HIL-pos | 4.25 | 227.0662 | −4.70075 |
| QI2912 | | | C18-neg | 13.37 | 303.2232 | −4.69693 |
| QI1409 | | | HIL-pos | 4.28 | 155.0452 | −4.67547 |
| cmp.QI4890 | | | C8-pos | 9.3 | 762.6555 | −4.67128 |
| QI2503 | | | C18-neg | 1.54 | 265.0415 | −4.66499 |
| cmp.QI2142 | | | C8-pos | 9.28 | 483.8013 | −4.6621 |
| cmp.QI5414 | | | C8-pos | 9.28 | 807.635 | −4.66188 |
| QI6803 | | | C18-neg | 10.39 | 644.2724 | −4.65518 |
| cmp.QI5616 | | | C8-pos | 8.81 | 823.6029 | −4.65245 |
| QI2263 | | | HIL-pos | 1.98 | 193.086 | −4.64556 |
| QI7063 | | | HIL-pos | 5.35 | 774.5429 | −4.63317 |
| QI3208 | | | HIL-pos | 1.94 | 239.0913 | −4.63301 |
| cmp.QI1351 | | | C8-pos | 11.43 | 369.3513 | −4.6131 |
| QI6677 | | | HIL-pos | 1.58 | 680.525 | −4.60824 |
| QI5671 | | | C18-neg | 7.61 | 528.263 | −4.60659 |
| cmp.QI6794 | | | C8-pos | 9.28 | 943.6094 | −4.59928 |
| cmp.QI6867 | | | C8-pos | 9.51 | 957.6259 | −4.59916 |
| QI6551 | | | C18-neg | 10.39 | 600.3299 | −4.5891 |
| cmp.QI2583 | | | C8-pos | 4.43 | 542.3243 | −4.57361 |
| QI5906 | | | C18-neg | 7.59 | 550.2451 | −4.56771 |
| QI1441 | | | C18-neg | 2.38 | 197.0534 | −4.56124 |
| QI6899 | | | HIL-pos | 5.4 | 736.5277 | −4.56079 |
| cmp.QI5243 | | | C8-pos | 8.4 | 794.5675 | −4.52305 |
| cmp.QI5899 | | | C8-pos | 9.12 | 849.6071 | −4.52219 |
| QI2957 | | | HIL-pos | 5.46 | 226.0822 | −4.52023 |
| cmp.QI3478 | | | C8-pos | 4.43 | 632.2935 | −4.51425 |
| QI3209 | | | HIL-pos | 2.02 | 239.0913 | −4.50035 |
| cmp.QI6089 | | | C8-pos | 8.15 | 866.0272 | −4.49616 |
| cmp.QI2788 | | | C8-pos | 4.43 | 564.3061 | −4.48651 |
| QI2501 | | | HIL-pos | 8.2 | 203.1391 | −4.46336 |
| QI3635 | | | HIL-pos | 4.18 | 267.0587 | −4.44863 |
| QI1439 | | | C18-neg | 1 | 197.0534 | −4.4451 |
| cmp.QI1375 | | | C8-pos | 11.43 | 371.358 | −4.44355 |
| cmp.QI1669 | | | C8-pos | 9.8 | 420.3193 | −4.43035 |
| QI6727 | | | HIL-pos | 2.41 | 694.5801 | −4.42669 |
| cmp.QI5379 | | | C8-pos | 9.93 | 804.7022 | −4.41538 |
| QI5980 | | | HIL-pos | 1.62 | 540.4694 | −4.40271 |
| cmp.QI5863 | | | C8-pos | 8.64 | 846.5394 | −4.40229 |
| cmp.QI4416 | | | C8-pos | 11.43 | 716.6332 | −4.39525 |
| QI3714 | | | C18-neg | 2.83 | 357.0125 | −4.39433 |
| cmp.QI5091 | | | C8-pos | 8.16 | 780.5533 | −4.38584 |
| cmp.QI4987 | | | C8-pos | 9.05 | 771.6365 | −4.35461 |

TABLE 2-continued (HMDB ID: Human Metabolome Database ID, Method: LC-MS method
where the metabolite was measured, RT: Retention Time, m/z: mass over charge, log10_pval:
Logarithm of the p value measuring association with all-cause mortality.)

| Compound | HMDB ID | Metabolite | Method | RT | m/z | log10_pval |
|---|---|---|---|---|---|---|
| QI5128 | | | C18-neg | 12.35 | 479.3375 | −4.34353 |
| cmp.QI7129 | | | C8-pos | 9.27 | 1011.597 | −4.33853 |
| cmp.QI6658 | | | C8-pos | 9.6 | 925.1411 | −4.32408 |
| cmp.QI271 | | C54:9 TAG +NH4 | C8-pos | 10.95 | 890.7247 | −4.31852 |
| cmp.QI1616 | | | C8-pos | 9.28 | 412.3036 | −4.31812 |
| cmp.QI4274 | | | C8-pos | 11.43 | 702.6174 | −4.31754 |
| cmp.QI2787 | | | C8-pos | 4.34 | 564.306 | −4.29495 |
| cmp.QI105 | HMDB12104 | C22:1 SM | C8-pos | 9.28 | 785.653 | −4.28779 |
| cmp.QI5169 | | | C8-pos | 7.91 | 788.5195 | −4.28582 |
| cmp.QI4929 | | | C8-pos | 7.91 | 766.5377 | −4.26937 |
| QI1348 | | | C18-neg | 10.55 | 183.1379 | −4.26748 |
| cmp.TF08 | | C54:10 TAG | C8-pos | 9.8 | 893.6624 | −4.26591 |
| QI5653 | | | C18-neg | 10.39 | 526.293 | −4.26497 |
| cmp.QI5710 | | | C8-pos | 8.17 | 832.5372 | −4.26271 |
| QI6804 | | | C18-neg | 10.6 | 644.273 | −4.26122 |
| QI4176 | | | HIL-pos | 2.5 | 307.2015 | −4.25307 |
| cmp.QI4798 | | | C8-pos | 7.65 | 752.5221 | −4.24859 |
| QI1306 | | | C18-neg | 17.87 | 180.0324 | −4.23561 |
| cmp.QI6058 | | | C8-pos | 10.02 | 863.6975 | −4.23455 |
| cmp.QI82 | | C42:11 PE plasmalogen | C8-pos | 8.79 | 796.5252 | −4.23408 |
| QI5426 | | | HIL-pos | 2.4 | 446.2903 | −4.23177 |
| QI12 | HMDB01999 | Eicosapentaenoic acid | C18-neg | 13.37 | 301.217 | −4.2275 |
| QI1 | HMDB03331 | 1-Methyladenosine | HIL-pos | 7.74 | 282.1195 | −4.2244 |
| cmp.QI1618 | | | C8-pos | 9.28 | 412.8053 | −4.22244 |
| QI2203 | | | HIL-pos | 9.84 | 189.1792 | −4.22121 |
| cmp.QI5670 | | | C8-pos | 10.14 | 829.7158 | −4.22025 |
| QI3536 | | | C18-neg | 2.77 | 339.0395 | −4.21087 |
| QI6198 | | | HIL-pos | 7.72 | 580.2799 | −4.20313 |
| cmp.QI5471 | | | C8-pos | 8.65 | 812.5578 | −4.20248 |
| QI2197 | | | HIL-pos | 9.25 | 189.1346 | −4.19916 |
| cmp.QI2922 | | | C8-pos | 6.17 | 578.4181 | −4.18598 |
| QI6459 | | | HIL-pos | 1.92 | 624.4469 | −4.17876 |
| cmp.QI5002 | | | C8-pos | 10.95 | 773.6192 | −4.17874 |
| QI2186 | | | HIL-pos | 9.84 | 188.1758 | −4.17265 |
| cmp.QI6917 | | | C8-pos | 8.66 | 966.5417 | −4.16998 |
| cmp.QI4734 | | | C8-pos | 8.92 | 745.6208 | −4.16599 |
| QI6739 | | | HIL-pos | 5.48 | 698.512 | −4.16241 |
| QI4244 | | | C18-neg | 2.77 | 413.0439 | −4.1488 |
| QI4191 | | | C18-neg | 2.75 | 407.0268 | −4.14639 |
| QI3811 | | | C18-neg | 13.37 | 369.2042 | −4.14359 |
| QI3157 | | | C18-neg | 2.77 | 323.0746 | −4.14288 |
| cmp.QI2199 | | | C8-pos | 9.79 | 491.3153 | −4.14217 |
| cmp.QI5506 | | | C8-pos | 9.55 | 816.152 | −4.14208 |
| QI3802 | | | HIL-pos | 1.94 | 279.0838 | −4.12668 |
| cmp.QI5682 | | | C8-pos | 8.65 | 830.5662 | −4.12093 |
| cmp.QI5354 | | | C8-pos | 8.17 | 803.037 | −4.10347 |
| QI1652 | | | C18-neg | 2.78 | 211.0968 | −4.09812 |
| cmp.QI5782 | | | C8-pos | 8.16 | 838.6065 | −4.09572 |
| TF84 | HMDB00262 | thymine | HILIC-neg | 1.35 | 125.0357 | −4.0929 |
| QI3080 | | | C18-neg | 13.8 | 315.2326 | −4.08932 |
| QI3908 | | | HIL-pos | 4.33 | 286.1033 | −4.08913 |
| cmp.QI5962 | | | C8-pos | 7.91 | 856.5065 | −4.08404 |
| QI7368 | | | C18-neg | 10.6 | 784.2594 | −4.07063 |
| QI1036 | | | HIL-pos | 5.83 | 139.0503 | −4.07048 |
| QI3061 | | | HIL-pos | 8.63 | 230.1863 | −4.06806 |
| QI3597 | | | C18-neg | 2.77 | 345.0564 | −4.06094 |
| QI6376 | | | HIL-pos | 5.37 | 609.5242 | −4.05505 |
| cmp.QI5655 | | | C8-pos | 9.77 | 827.7002 | −4.05499 |
| QI1672 | | | HIL-pos | 8.69 | 167.0217 | −4.05056 |
| QI2213 | | | HIL-pos | 4.04 | 190.1074 | −4.04841 |
| QI2719 | | | C18-neg | 5.28 | 285.9895 | −4.04789 |
| QI4381 | | | HIL-pos | 7.53 | 326.1461 | −4.04699 |
| cmp.QI123 | HMDB06731 | C20:5 CE | C8-pos | 11.43 | 693.5575 | −4.04634 |
| QI6754 | | | C18-neg | 13.38 | 633.4913 | −4.04435 |
| QI2584 | | | C18-neg | 2.79 | 277.0691 | −4.04381 |
| cmp.QI6272 | | | C8-pos | 8.34 | 884.5369 | −4.04345 |
| QI10 | HMDB01182 | 6-8-Dihydroxypurine | HIL-pos | 4.44 | 153.0408 | −4.04208 |
| QI6851 | | | C18-neg | 10.4 | 654.3016 | −4.02843 |
| cmp.QI6096 | | | C8-pos | 8.64 | 866.638 | −4.02405 |
| QI1882 | | | HIL-pos | 7.25 | 175.0714 | −4.02244 |
| QI2292 | | | HIL-pos | 5.41 | 194.1038 | −4.02124 |
| QI5791 | | | C18-neg | 2.75 | 533.1633 | −4.01738 |
| QI2356 | | | HIL-pos | 4.52 | 198.0431 | −4.01702 |

TABLE 2-continued (HMDB ID: Human Metabolome Database ID, Method: LC-MS method where the metabolite was measured, RT: Retention Time, m/z: mass over charge, log10_pval: Logarithm of the p value measuring association with all-cause mortality.)

| Compound | HMDB ID | Metabolite | Method | RT | m/z | log10_pval |
|---|---|---|---|---|---|---|
| cmp.QI5811 | | | C8-pos | 10.02 | 841.7165 | −4.01646 |
| QI6732 | | | HIL-pos | 1.99 | 696.5958 | −4.00478 |
| QI590 | | | C18-neg | 17.93 | 134.8933 | −3.99799 |
| QI6919 | | | HIL-pos | 6.59 | 740.5584 | −3.99375 |
| QI1483 | | | HIL-pos | 4.26 | 158.0812 | −3.99353 |
| cmp.QI5493 | | | C8-pos | 8.69 | 814.5707 | −3.98887 |
| QI2268 | | | C18-neg | 2.78 | 255.0871 | −3.98596 |
| QI6080 | | | C18-neg | 10.4 | 576.2855 | −3.98323 |
| QI7155 | | | HIL-pos | 6.54 | 794.5699 | −3.97772 |
| cmp.QI3132 | | | C8-pos | 6.75 | 599.4279 | −3.97402 |
| QI1958 | | | HIL-pos | 2.57 | 179.1068 | −3.96782 |
| QI7133 | | | HIL-pos | 5.34 | 790.5745 | −3.96706 |
| QI7071 | | | C18-neg | 10.6 | 716.2717 | −3.96599 |
| QI2493 | | | C18-neg | 7.96 | 263.6279 | −3.9586 |
| QI3818 | | | HIL-pos | 13.03 | 279.6862 | −3.9495 |
| cmp.QI1601 | | | C8-pos | 8.17 | 409.7538 | −3.94924 |
| cmp.QI3310 | | | C8-pos | 6.98 | 615.4233 | −3.94792 |
| QI2028 | | | C18-neg | 17.93 | 236.0955 | −3.94348 |
| QI6907 | | | C18-neg | 10.59 | 668.317 | −3.9426 |
| QI6346 | | | C18-neg | 10.4 | 586.3141 | −3.92576 |
| QI7411 | | | C18-neg | 10.39 | 790.2769 | −3.91847 |
| QI3581 | | | C18-neg | 1 | 341.9995 | −3.9096 |
| cmp.QI6603 | | | C8-pos | 9.12 | 917.5944 | −3.90761 |
| cmp.QI72 | HMDB11410 | C36:5 PE plasmalogen | C8-pos | 8.74 | 724.5275 | −3.90537 |
| QI130 | HMDB00252 | sphingosine | HIL-pos | 2 | 300.2897 | −3.9052 |
| QI3725 | | | C18-neg | 13.37 | 359.1757 | −3.90454 |
| cmp.QI84 | HMDB12356 | C34:0 PS | C8-pos | 8.16 | 764.5474 | −3.90328 |
| QI7121 | | | C18-neg | 10.6 | 722.2892 | −3.90101 |
| cmp.QI2086 | | | C8-pos | 9.4 | 477.8015 | −3.89446 |
| QI6081 | | | C18-neg | 10.6 | 576.2855 | −3.89255 |
| QI6024 | | | C18-neg | 7.66 | 567.3164 | −3.89224 |
| QI7134 | | | HIL-pos | 6.46 | 790.5745 | −3.89114 |
| QI5310 | | | C18-neg | 13.38 | 505.179 | −3.88671 |
| QI3234 | | | HIL-pos | 2.03 | 241.0958 | −3.88567 |
| cmp.QI5376 | | | C8-pos | 8.84 | 804.5877 | −3.88418 |
| QI4456 | | | C18-neg | 13.37 | 437.1915 | −3.86755 |
| cmp.QI6434 | | | C8-pos | 8.65 | 898.5538 | −3.86538 |
| cmp.QI515 | | | C8-pos | 2.9 | 239.0911 | −3.86373 |
| QI2154 | | | HIL-pos | 4.34 | 186.0761 | −3.85969 |
| QI4796 | | | HIL-pos | 7.09 | 364.3092 | −3.84819 |
| QI3092 | | | C18-neg | 11.97 | 317.2125 | −3.84411 |
| QI6850 | | | C18-neg | 10.6 | 654.3015 | −3.83925 |
| QI3962 | | | HIL-pos | 4.23 | 290.1346 | −3.83695 |
| cmp.QI5315 | | | C8-pos | 7.89 | 800.5195 | −3.82735 |
| QI1392 | | | HIL-pos | 4.34 | 154.0612 | −3.82049 |
| cmp.QI6623 | | | C8-pos | 10.15 | 919.6851 | −3.81642 |
| cmp.QI7182 | | | C8-pos | 8.66 | 1034.529 | −3.8158 |
| cmp.QI5233 | | | C8-pos | 8.59 | 793.5909 | −3.81355 |
| cmp.QI2650 | | | C8-pos | 8.95 | 550.2176 | −3.81071 |
| QI2193 | | | C18-neg | 10.55 | 251.1258 | −3.81017 |
| QI1310 | | | C18-neg | 18.61 | 180.0324 | −3.80943 |
| QI7014 | | | HIL-pos | 5.39 | 764.5588 | −3.80107 |
| QI2713 | | | C18-neg | 6.11 | 285.9895 | −3.78106 |
| QI7122 | | | C18-neg | 10.4 | 722.2892 | −3.78102 |
| QI571 | | | HIL-pos | 4.34 | 112.051 | −3.77333 |
| cmp.QI5058 | | | C8-pos | 7.89 | 778.5376 | −3.77137 |
| QI7410 | | | C18-neg | 10.6 | 790.2766 | −3.7585 |
| QI6733 | | | HIL-pos | 2.41 | 696.5959 | −3.75617 |
| QI7183 | | | C18-neg | 10.61 | 736.3046 | −3.75233 |
| cmp.QI4881 | | | C8-pos | 11.44 | 761.545 | −3.74773 |
| QI2913 | | | C18-neg | 13.88 | 303.2325 | −3.74491 |
| cmp.QI5690 | | | C8-pos | 8.65 | 831.0677 | −3.73537 |
| cmp.QI5475 | | | C8-pos | 8.66 | 813.0679 | −3.72835 |
| cmp.QI6920 | | | C8-pos | 11.12 | 966.7535 | −3.72238 |
| QI5962 | | | HIL-pos | 1.61 | 538.4535 | −3.72057 |
| QI5130 | | | HIL-pos | 6.92 | 406.1323 | −3.71929 |
| QI7153 | | | HIL-pos | 6.76 | 794.5671 | −3.71902 |
| cmp.QI4275 | | | C8-pos | 11.62 | 702.6175 | −3.71734 |
| QI5790 | | | HIL-pos | 8.28 | 509.3352 | −3.71618 |
| cmp.QI5223 | | | C8-pos | 8.69 | 792.5886 | −3.71391 |
| cmp.QI7118 | | | C8-pos | 8.17 | 1006.497 | −3.71343 |
| QI5074 | | | HIL-pos | 2.55 | 397.383 | −3.70816 |
| cmp.QI5063 | | | C8-pos | 9.36 | 778.5745 | −3.70808 |
| QI3986 | | | C18-neg | 9.36 | 386.9171 | −3.70795 |

TABLE 2-continued (HMDB ID: Human Metabolome Database ID, Method: LC-MS method
where the metabolite was measured, RT: Retention Time, m/z: mass over charge, log10_pval:
Logarithm of the p value measuring association with all-cause mortality.)

| Compound | HMDB ID | Metabolite | Method | RT | m/z | log10_pval |
|---|---|---|---|---|---|---|
| QI6623 | | | C18-neg | 8 | 611.3427 | −3.7069 |
| QI7172 | | | C18-neg | 10.6 | 730.2874 | −3.70497 |
| QI964 | | | C18-neg | 1 | 157.0605 | −3.70246 |
| cmp.QI4904 | | | C8-pos | 8.16 | 764.0455 | −3.69774 |
| cmp.QI6807 | | | C8-pos | 10.97 | 945.694 | −3.69165 |
| QI6347 | | | C18-neg | 10.6 | 586.3141 | −3.68799 |
| cmp.QI5260 | | | C8-pos | 9.18 | 796.1074 | −3.68686 |
| QI5677 | | | C18-neg | 6.97 | 528.2634 | −3.68149 |
| QI6550 | | | C18-neg | 10.6 | 600.3296 | −3.67447 |
| cmp.QI7167 | | | C8-pos | 9.78 | 1027.628 | −3.67413 |
| cmp.QI4565 | | | C8-pos | 13.08 | 729.6517 | −3.66445 |
| QI2605 | | | HIL-pos | 3.46 | 208.064 | −3.66407 |
| cmp.QI4995 | | | C8-pos | 8.85 | 772.5248 | −3.65313 |
| QI3569 | | | C18-neg | 15.46 | 341.197 | −3.65145 |
| cmp.QI4161 | | | C8-pos | 11.13 | 691.5421 | −3.64783 |
| cmp.QI4952 | | | C8-pos | 8.64 | 768.5874 | −3.64065 |
| QI5075 | | | HIL-pos | 2.01 | 397.383 | −3.63977 |
| cmp.QI5539 | | | C8-pos | 8.16 | 818.508 | −3.62931 |
| QI4153 | | | HIL-pos | 4.81 | 305.0855 | −3.62299 |
| QI3129 | | | C18-neg | 6.76 | 319.6632 | −3.61565 |
| cmp.QI4564 | | | C8-pos | 11.43 | 729.6286 | −3.61523 |
| cmp.QI6133 | | | C8-pos | 10.84 | 869.6633 | −3.60997 |
| QI3934 | | | C18-neg | 5.95 | 385.114 | −3.59992 |
| QI1296 | | | HIL-pos | 9.44 | 149.1196 | −3.59572 |
| cmp.QI1693 | | | C8-pos | 8.65 | 423.7695 | −3.59322 |
| QI6938 | | | HIL-pos | 7.1 | 745.6217 | −3.5828 |
| cmp.QI5816 | | | C8-pos | 7.66 | 842.4911 | −3.57702 |
| cmp.QI5978 | | | C8-pos | 9.6 | 857.1532 | −3.56523 |
| QI3646 | | | C18-neg | 13.51 | 347.2102 | −3.5549 |
| cmp.QI6099 | | | C8-pos | 9.95 | 866.6603 | −3.54883 |
| QI5091 | | | C18-neg | 2.77 | 475.014 | −3.53325 |
| QI7143 | | | HIL-pos | 6.46 | 792.5903 | −3.52508 |
| cmp.QI5218 | | | C8-pos | 8.65 | 792.0773 | −3.52105 |
| cmp.QI2411 | | | C8-pos | 4.67 | 520.3078 | −3.5204 |
| QI1260 | | | C18-neg | 1 | 175.0712 | −3.51338 |
| QI3707 | | | C18-neg | 2.84 | 355.0125 | −3.50739 |
| cmp.QI5906 | | | C8-pos | 7.97 | 850.5352 | −3.50655 |
| cmp.QI6363 | | | C8-pos | 9.6 | 891.1472 | −3.50284 |
| cmp.QI289 | HMDB10513 | C56:10 TAG | C8-pos | 11.12 | 921.6942 | −3.50237 |
| cmp.QI2592 | | | C8-pos | 7.36 | 543.9203 | −3.50133 |
| QI4335 | | | HIL-pos | 7.73 | 320.0754 | −3.49828 |
| QI6843 | | | C18-neg | 8.41 | 651.3592 | −3.49636 |
| cmp.QI1038 | | | C8-pos | 5.03 | 320.2559 | −3.48958 |
| cmp.QI6655 | | | C8-pos | 9.6 | 924.6394 | −3.48922 |
| QI3516 | | | HIL-pos | 4.25 | 259.0925 | −3.48866 |
| QI5479 | | | HIL-pos | 1.67 | 455.3731 | −3.47151 |
| cmp.QI4788 | | | C8-pos | 7.38 | 751.4967 | −3.47108 |
| cmp.QI5845 | | | C8-pos | 9.95 | 844.6785 | −3.4701 |
| QI608 | | | C18-neg | 17.74 | 136.8902 | −3.46972 |
| QI6865 | | | C18-neg | 10.6 | 658.2442 | −3.46843 |
| QI2247 | | | HIL-pos | 3.5 | 192.069 | −3.46752 |
| QI3309 | | | C18-neg | 14.37 | 327.2328 | −3.46086 |
| QI5450 | | | C18-neg | 13.28 | 517.389 | −3.45635 |
| cmp.QI6715 | | | C8-pos | 9.96 | 934.6483 | −3.45225 |
| QI3302 | | | C18-neg | 8.66 | 327.1636 | −3.44745 |
| cmp.QI6871 | | | C8-pos | 9.58 | 958.6323 | −3.44638 |
| QI2564 | | | C18-neg | 1.04 | 271.9258 | −3.44549 |
| cmp.QI7069 | | | C8-pos | 11.09 | 995.7095 | −3.43497 |
| cmp.QI5244 | | | C8-pos | 8.28 | 794.5703 | −3.43406 |
| QI1071 | | | C18-neg | 16.28 | 162.981 | −3.43233 |
| cmp.QI5524 | | | C8-pos | 8.38 | 817.5565 | −3.43206 |
| QI5673 | | | C18-neg | 6.44 | 528.263 | −3.42659 |
| QI6644 | | | HIL-pos | 2.41 | 668.5646 | −3.41836 |
| QI6344 | | | C18-neg | 10.5 | 586.3138 | −3.4144 |
| QI931 | | | HIL-pos | 3.75 | 133.0497 | −3.39657 |
| QI6670 | | | HIL-pos | 7.22 | 677.5593 | −3.39569 |
| QI6686 | | | HIL-pos | 2.98 | 682.5613 | −3.39179 |
| QI5548 | | | HIL-pos | 1.71 | 466.2989 | −3.39174 |
| QI2776 | | | C18-neg | 3.31 | 291.0832 | −3.39108 |
| QI1448 | | | HIL-pos | 3.57 | 156.102 | −3.38508 |
| QI1976 | | | HIL-pos | 4.73 | 180.0518 | −3.37644 |
| cmp.QI290 | | C56:10 TAG +NH4 | C8-pos | 11.12 | 916.739 | −3.3739 |
| cmp.QI6389 | | | C8-pos | 10.77 | 893.6638 | −3.37309 |
| QI5441 | | | C18-neg | 9.87 | 517.1133 | −3.37187 |

TABLE 2-continued (HMDB ID: Human Metabolome Database ID, Method: LC-MS method
where the metabolite was measured, RT: Retention Time, m/z: mass over charge, log10_pval:
Logarithm of the p value measuring association with all-cause mortality.)

| Compound | HMDB ID | Metabolite | Method | RT | m/z | log10_pval |
|---|---|---|---|---|---|---|
| cmp.QI5180 | | | C8-pos | 10.95 | 789.5931 | −3.37122 |
| cmp.QI5613 | | | C8-pos | 9.6 | 823.1596 | −3.36661 |
| cmp.QI6122 | | | C8-pos | 7.89 | 868.5069 | −3.36626 |
| QI6730 | | | HIL-pos | 7.31 | 695.5095 | −3.36328 |
| QI2847 | | | HIL-pos | 4.2 | 223.0714 | −3.36288 |
| cmp.QI106 | HMDB12103 | C22:0 SM | C8-pos | 9.57 | 787.6676 | −3.3613 |
| QI1237 | | | HIL-pos | 3.77 | 147.0765 | −3.35887 |
| cmp.QI5928 | | | C8-pos | 7.9 | 852.5536 | −3.35585 |
| QI3490 | | | C18-neg | 2.83 | 335.0279 | −3.35509 |
| QI6345 | | | C18-neg | 10.53 | 586.314 | −3.35497 |
| QI3028 | | | C18-neg | 2.82 | 313.0462 | −3.35124 |
| QI4735 | | | HIL-pos | 5.64 | 358.1708 | −3.34732 |
| QI1936 | | | HIL-pos | 9.43 | 178.0587 | −3.34597 |
| QI4370 | | | C18-neg | 7.28 | 427.1136 | −3.3367 |
| QI3659 | | | C18-neg | 13.85 | 349.2149 | −3.33518 |
| QI5652 | | | C18-neg | 10.6 | 526.2927 | −3.33483 |
| QI4907 | | | C18-neg | 9.38 | 460.9212 | −3.3286 |
| QI60 | HMDB10404 | C22:6 LPC | HIL-pos | 7.6 | 568.3396 | −3.32679 |
| cmp.QI6773 | | | C8-pos | 10.98 | 940.7401 | −3.32553 |
| cmp.QI5014 | | | C8-pos | 7.65 | 774.504 | −3.32388 |
| QI189 | | | C18-neg | 1 | 96.9586 | −3.32385 |
| cmp.QI6320 | | | C8-pos | 11.04 | 887.6521 | −3.3191 |
| QI6545 | | | C18-neg | 1.03 | 600.0618 | −3.31905 |
| QI6059 | | | HIL-pos | 4.02 | 552.0604 | −3.3044 |
| QI5602 | | | HIL-pos | 2.42 | 475.2974 | −3.29928 |
| QI1953 | | | HIL-pos | 2.03 | 179.0704 | −3.2977 |
| QI628 | | | HIL-pos | 3.75 | 115.0506 | −3.29528 |
| QI2651 | | | HIL-pos | 2.52 | 210.1128 | −3.29346 |
| cmp.QI6717 | | | C8-pos | 11.6 | 934.7886 | −3.29262 |
| cmp.QI309 | HMDB10531 | C58:11 TAG | C8-pos | 11.25 | 947.7089 | −3.28907 |
| cmp.QI5800 | | | C8-pos | 9.11 | 840.5879 | −3.28659 |
| QI5936 | | | C18-neg | 10.72 | 553.3252 | −3.28359 |
| cmp.QI1726 | | | C8-pos | 7.26 | 427.2369 | −3.28001 |
| QI5331 | | | C18-neg | 10.72 | 507.3197 | −3.27436 |
| QI2495 | | | C18-neg | 7.03 | 263.6279 | −3.27126 |
| cmp.QI4988 | | | C8-pos | 9 | 771.6379 | −3.26609 |
| QI4419 | | | C18-neg | 13.86 | 434.2306 | −3.26375 |
| QI5126 | | | C18-neg | 10.92 | 479.3371 | −3.26353 |
| QI973 | | | C18-neg | 1.03 | 158.0639 | −3.25001 |
| QI1867 | | | HIL-pos | 3.84 | 174.1126 | −3.24558 |
| QI6262 | | | HIL-pos | 7.52 | 590.3217 | −3.245 |
| QI4003 | | | HIL-pos | 2.49 | 293.186 | −3.24392 |
| cmp.QI310 | HMDB10531 | C58:11 TAG +NH4 | C8-pos | 11.25 | 942.7547 | −3.24171 |
| QI5155 | | | C18-neg | 11.99 | 481.3532 | −3.24126 |
| cmp.QI118 | HMDB00610 | C18:2 CE +NH4 | C8-pos | 11.83 | 666.6182 | −3.24121 |
| QI1319 | | | HIL-pos | 8.69 | 151.0478 | −3.23985 |
| QI2826 | | | HIL-pos | 2.02 | 221.0809 | −3.23914 |
| QI5065 | | | HIL-pos | 2.01 | 395.3675 | −3.23736 |
| QI3591 | | | C18-neg | 1 | 343.9945 | −3.23527 |
| QI5110 | | | HIL-pos | 1.72 | 402.2638 | −3.22874 |
| QI6766 | | | HIL-pos | 5.54 | 704.5593 | −3.21814 |
| QI6891 | | | HIL-pos | 5.41 | 734.5119 | −3.21717 |
| QI1025 | | | HIL-pos | 4.41 | 138.0551 | −3.21567 |
| QI4160 | | | HIL-pos | 2 | 305.186 | −3.21564 |
| QI6711 | | | C18-neg | 8.02 | 624.3381 | −3.21486 |
| cmp.QI5283 | | | C8-pos | 8.16 | 798.0388 | −3.21414 |
| QI4113 | | | C18-neg | 2.85 | 396.9982 | −3.21393 |
| cmp.QI4880 | | | C8-pos | 8.15 | 761.5391 | −3.21082 |
| QI4237 | | | C18-neg | 1.59 | 411.9823 | −3.21065 |
| cmp.QI5203 | | | C8-pos | 9.71 | 790.6865 | −3.2065 |
| QI4421 | | | C18-neg | 7.3 | 435.1455 | −3.20348 |
| QI4002 | | | HIL-pos | 2 | 293.186 | −3.20171 |
| QI6937 | | | C18-neg | 13.86 | 677.4539 | −3.20055 |
| cmp.QI5004 | | | C8-pos | 9.28 | 773.6529 | −3.20041 |
| QI5064 | | | HIL-pos | 2.56 | 395.3675 | −3.1992 |
| cmp.QI5971 | | | C8-pos | 9.6 | 856.6516 | −3.19405 |
| cmp.QI11 | HMDB10404 | C22:6 LPC | C8-pos | 4.67 | 568.34 | −3.19353 |
| QI6855 | | | HIL-pos | 5.41 | 724.5276 | −3.18714 |
| cmp.QI6605 | | | C8-pos | 9.77 | 917.6698 | −3.18152 |
| cmp.QI5623 | | | C8-pos | 9.79 | 824.1677 | −3.18048 |
| QI5642 | | | HIL-pos | 1.65 | 481.3888 | −3.17854 |
| QI4362 | | | C18-neg | 7.27 | 425.1167 | −3.17731 |
| QI3767 | | | C18-neg | 7.32 | 367.1582 | −3.17669 |
| QI6874 | | | C18-neg | 13.86 | 659.5066 | −3.1765 |

TABLE 2-continued (HMDB ID: Human Metabolome Database ID, Method: LC-MS method
where the metabolite was measured, RT: Retention Time, m/z: mass over charge, log10_pval:
Logarithm of the p value measuring association with all-cause mortality.)

| Compound | HMDB ID | Metabolite | Method | RT | m/z | log10_pval |
|---|---|---|---|---|---|---|
| QI5324 | | | HIL-pos | 1.75 | 432.3114 | −3.17333 |
| QI2518 | | | HIL-pos | 5.53 | 204.0868 | −3.16975 |
| cmp.QI5060 | | | C8-pos | 8.96 | 778.5717 | −3.16898 |
| cmp.QI4185 | | | C8-pos | 11.83 | 694.649 | −3.16307 |
| QI2380 | | | C18-neg | 13.38 | 257.2273 | −3.16118 |
| QI3394 | | | HIL-pos | 3.75 | 251.0776 | −3.16046 |
| QI5650 | | | C18-neg | 6.95 | 526.2483 | −3.15644 |
| QI2656 | | | C18-neg | 13.87 | 283.2427 | −3.15438 |
| QI2517 | | | HIL-pos | 1.63 | 204.0868 | −3.15339 |
| cmp.QI5571 | | | C8-pos | 8.62 | 820.5837 | −3.15158 |
| cmp.QI4909 | | | C8-pos | 8.72 | 764.5564 | −3.14943 |
| QI1151 | | | HIL-pos | 3.46 | 144.0656 | −3.14935 |
| QI4105 | | | C18-neg | 13.86 | 395.2197 | −3.14544 |
| cmp.QI108 | HMDB11697 | C24:0 SM | C8-pos | 9.99 | 815.6999 | −3.14441 |
| QI3939 | | | C18-neg | 13.86 | 385.191 | −3.14212 |
| cmp.QI5703 | | | C8-pos | 8.15 | 832.034 | −3.13916 |
| cmp.QI4748 | | | C8-pos | 8.74 | 746.5101 | −3.13771 |
| cmp.QI5195 | | | C8-pos | 8.2 | 790.5351 | −3.13767 |
| cmp.QI4412 | | | C8-pos | 8.26 | 716.5575 | −3.13559 |
| QI6360 | | | HIL-pos | 7.63 | 606.2956 | −3.13448 |
| QI6460 | | | HIL-pos | 2.27 | 624.4469 | −3.13288 |
| cmp.QI1950 | | | C8-pos | 8.29 | 456.75 | −3.12666 |
| cmp.QI1698 | | | C8-pos | 8.65 | 424.2713 | −3.1257 |
| QI5290 | | | C18-neg | 7.29 | 503.1328 | −3.12248 |
| cmp.QI6290 | | | C8-pos | 10.84 | 885.6364 | −3.12184 |
| QI6726 | | | HIL-pos | 1.99 | 694.58 | −3.11773 |
| cmp.QI5062 | | | C8-pos | 9.23 | 778.5743 | −3.11759 |
| QI5848 | | | HIL-pos | 1.73 | 519.1287 | −3.11333 |
| cmp.QI5515 | | | C8-pos | 9.56 | 816.6475 | −3.11225 |
| QI2266 | | | C18-neg | 1 | 255.0595 | −3.11192 |
| cmp.QI3025 | | | C8-pos | 4.67 | 590.3215 | −3.11134 |
| cmp.QI1341 | | | C8-pos | 11.52 | 367.3357 | −3.10709 |
| QI4879 | | | HIL-pos | 7.06 | 371.8188 | −3.10653 |
| QI3344 | | | HIL-pos | 3.73 | 247.0924 | −3.10369 |
| cmp.QI4267 | | | C8-pos | 10 | 702.2849 | −3.09838 |
| QI7003 | | | HIL-pos | 5.37 | 762.5431 | −3.09665 |
| QI2580 | | | C18-neg | 12.86 | 275.2015 | −3.08367 |
| QI4176 | | | C18-neg | 12.34 | 403.1322 | −3.08304 |
| QI5755 | | | C18-neg | 1.54 | 529.952 | −3.08241 |
| QI3138 | | | C18-neg | 1.37 | 321.062 | −3.08062 |
| cmp.QI54 | HMDB11319 | C38:6 PC plasmalogen | C8-pos | 8.85 | 792.5884 | −3.07694 |
| cmp.QI4052 | | | C8-pos | 7.37 | 683.5096 | −3.06713 |
| cmp.QI6115 | | | C8-pos | 10.62 | 867.6473 | −3.06474 |
| cmp.QI270 | HMDB10498 | C54:9 TAG | C8-pos | 10.95 | 895.679 | −3.06095 |
| QI6786 | | | C18-neg | 5.41 | 640.3332 | −3.05863 |
| QI3347 | | | C18-neg | 13.87 | 330.2411 | −3.05569 |
| QI4256 | | | C18-neg | 6.58 | 413.2001 | −3.0554 |
| cmp.QI1205 | | | C8-pos | 7.35 | 350.2408 | −3.0521 |
| QI7022 | | | HIL-pos | 6.57 | 766.5383 | −3.05181 |
| QI4124 | | | C18-neg | 7.66 | 397.205 | −3.0497 |
| QI3666 | | | C18-neg | 9.04 | 350.2099 | −3.04669 |
| QI6039 | | | C18-neg | 11.3 | 568.3394 | −3.04547 |
| QI4177 | | | HIL-pos | 2 | 307.2016 | −3.04358 |
| QI2775 | | | C18-neg | 3.6 | 291.0832 | −3.04339 |
| cmp.QI6900 | | | C8-pos | 11.25 | 963.6834 | −3.03887 |
| cmp.QI4345 | | | C8-pos | 11.43 | 709.5314 | −3.03165 |
| QI3325 | | | C18-neg | 1 | 329.0295 | −3.02425 |
| QI3431 | | | C18-neg | 1.38 | 331.091 | −3.02022 |
| cmp.QI6944 | | | C8-pos | 11.12 | 971.7095 | −3.01485 |
| QI5997 | | | HIL-pos | 7.6 | 543.3267 | −3.0136 |
| QI6746 | | | HIL-pos | 7.24 | 699.5437 | −3.01213 |
| TF85 | HMDB00929 | tryptophan | HILIC-neg | 3.35 | 203.0826 | −3.01176 |
| QI2478 | | | C18-neg | 1.38 | 263.1035 | −3.00844 |
| QI6418 | | | C18-neg | 8.69 | 589.2987 | −3.00839 |
| cmp.QI3800 | | | C8-pos | 7.37 | 661.5277 | −3.00404 |
| QI1362 | | | HIL-pos | 5.96 | 153.0581 | −3.00209 |
| QI1725 | | | HIL-pos | 9.45 | 169.0948 | −2.99896 |
| QI7004 | | | HIL-pos | 7.07 | 762.646 | −2.99737 |
| cmp.QI6962 | | | C8-pos | 11.52 | 975.7404 | −2.98608 |
| cmp.QI5207 | | | C8-pos | 8.15 | 791.0369 | −2.98348 |
| QI5855 | | | C18-neg | 1.25 | 541.0361 | −2.98087 |
| QI3592 | | | C18-neg | 7.26 | 344.1567 | −2.98071 |
| QI7073 | | | HIL-pos | 7.05 | 776.662 | −2.97818 |

TABLE 2-continued (HMDB ID: Human Metabolome Database ID, Method: LC-MS method where the metabolite was measured, RT: Retention Time, m/z: mass over charge, log10_pval: Logarithm of the p value measuring association with all-cause mortality.)

| Compound | HMDB ID | Metabolite | Method | RT | m/z | log10_pval |
|---|---|---|---|---|---|---|
| QI15 | HMDB02183 | Docosahexaenoic acid | C18-neg | 13.86 | 327.2328 | −2.9768 |
| QI7477 | | | C18-neg | 17.76 | 814.5162 | −2.97475 |
| QI6749 | | | HIL-pos | 2.97 | 700.572 | −2.9745 |
| cmp.QI6289 | | | C8-pos | 9.79 | 885.6362 | −2.97317 |
| cmp.QI6622 | | | C8-pos | 10.88 | 919.6791 | −2.97265 |
| cmp.QI5889 | | | C8-pos | 9.07 | 848.6154 | −2.97253 |
| QI2583 | | | C18-neg | 1 | 277.0414 | −2.97143 |
| QI6853 | | | C18-neg | 13.86 | 655.4722 | −2.96685 |
| QI541 | | | HIL-pos | 9.42 | 110.0717 | −2.96598 |
| QI553 | | | C18-neg | 1 | 131.0812 | −2.96124 |
| QI7048 | | | C18-neg | 1.08 | 710.9785 | −2.95902 |
| QI6765 | | | HIL-pos | 6.69 | 704.5587 | −2.95872 |
| cmp.QI5757 | | | C8-pos | 8.4 | 836.0379 | −2.95852 |
| QI7361 | | | C18-neg | 11.04 | 782.3082 | −2.95796 |
| cmp.QI6251 | | | C8-pos | 8.13 | 882.521 | −2.95539 |
| QI1221 | | | C18-neg | 1.16 | 171.0762 | −2.9523 |
| cmp.QI4820 | | | C8-pos | 8.54 | 754.5738 | −2.94555 |
| cmp.QI3984 | | | C8-pos | 7.84 | 677.5588 | −2.94062 |
| cmp.QI6549 | | | C8-pos | 10.94 | 911.6523 | −2.93833 |
| cmp.QI6006 | | | C8-pos | 8.38 | 860.0368 | −2.93432 |
| cmp.QI80 | HMDB11384 | C38:3 PE plasmalogen | C8-pos | 8.95 | 756.5903 | −2.93356 |
| QI4975 | | | C18-neg | 13.86 | 463.2073 | −2.93066 |
| cmp.QI3897 | | | C8-pos | 7.09 | 669.4938 | −2.9305 |
| QI6844 | | | HIL-pos | 7.11 | 719.607 | −2.92917 |
| QI6576 | | | C18-neg | 16.28 | 605.4049 | −2.92907 |
| cmp.QI6265 | | | C8-pos | 11.03 | 883.6784 | −2.92499 |
| QI2516 | | | HIL-pos | 1.75 | 204.0868 | −2.92239 |
| QI5330 | | | HIL-pos | 1.66 | 433.3638 | −2.91825 |
| QI2744 | | | C18-neg | 6.73 | 288.6193 | −2.9155 |
| cmp.QI5442 | | | C8-pos | 9.57 | 809.6504 | −2.91516 |
| QI2506 | | | C18-neg | 1.39 | 265.1089 | −2.91248 |
| QI6689 | | | HIL-pos | 7.31 | 683.5095 | −2.91144 |
| cmp.QI1190 | | | C8-pos | 5.3 | 346.2739 | −2.90524 |
| QI1932 | | | HIL-pos | 1.72 | 177.1638 | −2.90416 |
| QI833 | | | HIL-pos | 3.59 | 128.0708 | −2.89944 |
| QI2659 | | | HIL-pos | 3.75 | 211.0716 | −2.89505 |
| QI3523 | | | C18-neg | 8.21 | 337.1674 | −2.89479 |
| QI5046 | | | HIL-pos | 5.54 | 393.2401 | −2.89456 |
| cmp.QI5927 | | | C8-pos | 8.19 | 852.5511 | −2.89298 |
| QI983 | | | C18-neg | 5.32 | 158.9772 | −2.88778 |
| cmp.QI6218 | | | C8-pos | 9.56 | 877.6379 | −2.88728 |
| QI7179 | | | HIL-pos | 7.08 | 797.5932 | −2.88688 |
| cmp.QI5681 | | | C8-pos | 8.51 | 830.566 | −2.88002 |
| QI3741 | | | C18-neg | 13.86 | 363.2089 | −2.87792 |
| QI1995 | | | C18-neg | 1.92 | 230.9963 | −2.8774 |
| QI2031 | | | C18-neg | 18.6 | 236.0955 | −2.87587 |
| QI769 | | | C18-neg | 1.38 | 145.0605 | −2.87376 |
| cmp.QI6460 | | | C8-pos | 9.61 | 902.2303 | −2.87086 |
| cmp.QI1213 | | | C8-pos | 5.3 | 351.2293 | −2.87004 |
| cmp.QI4329 | | | C8-pos | 11.61 | 707.5729 | −2.86785 |
| QI5759 | | | C18-neg | 1.7 | 529.9523 | −2.86496 |
| QI6704 | | | HIL-pos | 7.25 | 687.5436 | −2.86196 |
| QI5188 | | | HIL-pos | 1.75 | 414.3003 | −2.85929 |
| cmp.QI4016 | | | C8-pos | 11.83 | 680.6333 | −2.85917 |
| QI4887 | | | HIL-pos | 1.99 | 372.2898 | −2.85548 |
| QI968 | | | C18-neg | 1.18 | 157.0857 | −2.8542 |
| cmp.QI7077 | | | C8-pos | 11.62 | 996.7996 | −2.85287 |
| QI605 | | | C18-neg | 18.65 | 135.9696 | −2.85114 |
| QI3960 | | | C18-neg | 7.37 | 386.9168 | −2.85012 |
| cmp.QI7057 | | | C8-pos | 11.25 | 992.769 | −2.85006 |
| cmp.QI2589 | | | C8-pos | 7.36 | 543.4185 | −2.84958 |
| cmp.QI5771 | | | C8-pos | 9.99 | 837.6817 | −2.84837 |
| QI6710 | | | HIL-pos | 7.62 | 690.2564 | −2.84515 |
| QI1320 | | | C18-neg | 17.94 | 180.9882 | −2.84235 |
| QI4148 | | | C18-neg | 1.38 | 399.0781 | −2.84228 |
| QI4364 | | | C18-neg | 8.66 | 425.2002 | −2.83893 |
| cmp.QI5677 | | | C8-pos | 9.77 | 830.1675 | −2.83757 |
| QI3340 | | | C18-neg | 8.5 | 329.2332 | −2.83666 |
| QI3610 | | | C18-neg | 12.86 | 345.2432 | −2.83207 |
| QI6367 | | | HIL-pos | 5.38 | 607.5087 | −2.8314 |
| cmp.QI5969 | | | C8-pos | 8.34 | 856.5849 | −2.83086 |
| QI4427 | | | C18-neg | 2.78 | 436.8765 | −2.83004 |
| QI1865 | | | HIL-pos | 3.19 | 174.0762 | −2.82974 |
| cmp.QI5076 | | | C8-pos | 9.15 | 779.5763 | −2.82668 |

TABLE 2-continued (HMDB ID: Human Metabolome Database ID, Method: LC-MS method
where the metabolite was measured, RT: Retention Time, m/z: mass over charge, log10_pval:
Logarithm of the p value measuring association with all-cause mortality.)

| Compound | HMDB ID | Metabolite | Method | RT | m/z | log10_pval |
|---|---|---|---|---|---|---|
| QI3336 | | | C18-neg | 8.77 | 329.233 | −2.82507 |
| QI7079 | | | HIL-pos | 6.57 | 778.5382 | −2.8235 |
| QI7205 | | | C18-neg | 11.21 | 742.2872 | −2.82239 |
| QI3805 | | | C18-neg | 7.56 | 369.1738 | −2.82202 |
| QI7081 | | | C18-neg | 15.7 | 717.5182 | −2.82105 |
| QI2283 | | | C18-neg | 14.37 | 255.2325 | −2.819 |
| cmp.QI1632 | | | C8-pos | 9.57 | 413.8131 | −2.81591 |
| QI4232 | | | C18-neg | 1.75 | 411.9822 | −2.8071 |
| QI3310 | | | C18-neg | 14.21 | 327.2329 | −2.80458 |
| cmp.QI3674 | | | C8-pos | 11.84 | 649.5916 | −2.80411 |
| QI4234 | | | C18-neg | 1.34 | 411.9822 | −2.80363 |
| cmp.QI4272 | | | C8-pos | 7.42 | 702.5067 | −2.80355 |
| cmp.QI3927 | | | C8-pos | 9.84 | 672.6249 | −2.80259 |
| cmp.QI6528 | | | C8-pos | 9.11 | 908.575 | −2.80151 |
| QI493 | | | HIL-pos | 5.61 | 106.0503 | −2.80079 |
| QI7005 | | | HIL-pos | 7 | 762.6565 | −2.80004 |
| QI3325 | | | HIL-pos | 8.28 | 246.0909 | −2.79858 |
| cmp.QI3649 | | | C8-pos | 7.1 | 647.5121 | −2.79739 |
| QI6135 | | | HIL-pos | 1.77 | 568.4276 | −2.79669 |
| QI6933 | | | HIL-pos | 7.1 | 743.6061 | −2.79617 |
| QI1933 | | | HIL-pos | 2 | 177.1639 | −2.79611 |
| QI96 | HMDB00177 | histidine | HIL-pos | 9.42 | 156.0768 | −2.79422 |
| QI107 | | | C18-neg | 18.97 | 84.0075 | −2.79392 |
| QI4450 | | | C18-neg | 6.29 | 437.106 | −2.7936 |
| QI4699 | | | HIL-pos | 4.52 | 354.279 | −2.79326 |
| QI6826 | | | HIL-pos | 7.17 | 715.5743 | −2.78927 |
| QI6491 | | | C18-neg | 8.9 | 595.3492 | −2.78829 |
| cmp.QI5551 | | | C8-pos | 8.59 | 819.0672 | −2.78815 |
| cmp.QI5385 | | | C8-pos | 8.4 | 805.0525 | −2.78667 |
| QI2800 | | | C18-neg | 11.8 | 293.212 | −2.78662 |
| QI3654 | | | C18-neg | 1.01 | 348.9981 | −2.78386 |
| QI4516 | | | HIL-pos | 4.41 | 338.057 | −2.7794 |
| QI7518 | | | C18-neg | 17.73 | 824.5438 | −2.77552 |
| cmp.QI5329 | | | C8-pos | 11.83 | 801.531 | −2.77383 |
| QI5105 | | | C18-neg | 13.86 | 477.2223 | −2.77316 |
| QI879 | | | HIL-pos | 9.44 | 130.0865 | −2.76221 |
| QI3419 | | | HIL-pos | 10.35 | 252.1343 | −2.75843 |
| QI1847 | | | HIL-pos | 2.55 | 173.1174 | −2.75748 |
| QI5400 | | | C18-neg | 10.75 | 510.3196 | −2.7553 |
| cmp.QI3671 | | | C8-pos | 7.34 | 649.5276 | −2.7549 |
| QI3081 | | | C18-neg | 13.83 | 315.233 | −2.75379 |
| QI1455 | | | HIL-pos | 9.42 | 157.0802 | −2.7519 |
| cmp.QI1352 | | | C8-pos | 11.83 | 369.3514 | −2.75033 |
| cmp.QI6955 | | | C8-pos | 9.99 | 973.6566 | −2.74932 |
| QI4173 | | | C18-neg | 2.78 | 403.0149 | −2.7491 |
| cmp.QI4649 | | | C8-pos | 7.1 | 737.4813 | −2.74827 |
| QI2873 | | | C18-neg | 16.36 | 297.2795 | −2.74722 |
| QI3029 | | | C18-neg | 2.84 | 313.0463 | −2.74643 |
| cmp.QI1661 | | | C8-pos | 9.51 | 419.3122 | −2.7462 |
| QI5947 | | | HIL-pos | 1.66 | 536.4359 | −2.74533 |
| QI4208 | | | C18-neg | 13.86 | 409.2354 | −2.74286 |
| cmp.QI34 | HMDB07991 | C38:6 PC | C8-pos | 8.38 | 806.5686 | −2.74061 |
| QI6134 | | | HIL-pos | 7.85 | 568.3403 | −2.74041 |
| QI5481 | | | C18-neg | 6.2 | 520.9094 | −2.74016 |
| QI4826 | | | HIL-pos | 1.67 | 367.3574 | −2.73687 |
| cmp.QI41 | HMDB11214 | C34:5 PC plasmalogen | C8-pos | 8.97 | 738.5433 | −2.73647 |
| cmp.QI331 | | | C8-pos | 11.83 | 203.1794 | −2.7358 |
| QI1271 | | | HIL-pos | 9.44 | 148.1161 | −2.73321 |
| cmp.QI6091 | | | C8-pos | 8.24 | 866.5215 | −2.73228 |
| QI6784 | | | C18-neg | 6.55 | 640.3327 | −2.73127 |
| cmp.QI4226 | | | C8-pos | 10.12 | 698.642 | −2.72889 |
| QI6348 | | | C18-neg | 10.8 | 586.3145 | −2.72849 |
| QI669 | | | C18-neg | 17.6 | 141.0156 | −2.72724 |
| QI4262 | | | C18-neg | 6.18 | 415.1243 | −2.72634 |
| QI1661 | | | C18-neg | 5.21 | 213.0218 | −2.72607 |
| QI2155 | | | HIL-pos | 5.53 | 186.0762 | −2.7253 |
| QI6985 | | | HIL-pos | 7.06 | 757.6216 | −2.72513 |
| QI7593 | | | C18-neg | 17.84 | 838.5601 | −2.72504 |
| cmp.QI6906 | | | C8-pos | 8.38 | 964.5255 | −2.72123 |
| QI2696 | | | C18-neg | 5.37 | 285.9894 | −2.71782 |
| QI4006 | | | C18-neg | 1.37 | 389.0498 | −2.71565 |
| QI4095 | | | HIL-pos | 2.42 | 300.2897 | −2.70929 |
| QI6595 | | | HIL-pos | 1.58 | 656.5247 | −2.70783 |
| QI309 | | | HIL-pos | 9.44 | 84.0815 | −2.70397 |

TABLE 2-continued (HMDB ID: Human Metabolome Database ID, Method: LC-MS method where the metabolite was measured, RT: Retention Time, m/z: mass over charge, log10_pval: Logarithm of the p value measuring association with all-cause mortality.)

| Compound | HMDB ID | Metabolite | Method | RT | m/z | log10_pval |
|---|---|---|---|---|---|---|
| cmp.QI6537 | | | C8-pos | 11.18 | 909.6936 | −2.69892 |
| QI899 | | | HIL-pos | 9.44 | 131.0898 | −2.69853 |
| cmp.QI4725 | | | C8-pos | 8.74 | 744.5891 | −2.68943 |
| cmp.QI6076 | | | C8-pos | 10.84 | 864.7083 | −2.68843 |
| QI6799 | | | HIL-pos | 7.26 | 711.5406 | −2.68481 |
| QI6719 | | | HIL-pos | 1.18 | 692.3601 | −2.6829 |
| cmp.QI1691 | | | C8-pos | 8.38 | 423.2633 | −2.68246 |
| QI805 | | | HIL-pos | 4.55 | 126.0222 | −2.68126 |
| QI4740 | | | HIL-pos | 1.71 | 358.2952 | −2.67933 |
| QI6882 | | | C18-neg | 14.22 | 661.5228 | −2.67682 |
| QI7008 | | | HIL-pos | 7.31 | 763.497 | −2.67649 |
| cmp.QI2843 | | | C8-pos | 4.81 | 570.3552 | −2.67588 |
| QI3512 | | | HIL-pos | 5.67 | 258.2176 | −2.67499 |
| cmp.QI5695 | | | C8-pos | 10.8 | 831.6462 | −2.67425 |
| cmp.QI5490 | | | C8-pos | 8.14 | 814.5354 | −2.67238 |
| QI554 | | | C18-neg | 1 | 132.0288 | −2.67058 |
| QI209 | | | C18-neg | 18.94 | 98.9542 | −2.66711 |
| QI5924 | | | HIL-pos | 10.26 | 531.2897 | −2.66683 |
| QI3015 | | | C18-neg | 9.87 | 311.2229 | −2.66595 |
| QI6156 | | | HIL-pos | 1.73 | 573.4659 | −2.66375 |
| cmp.QI6716 | | | C8-pos | 11.71 | 934.7867 | −2.66236 |
| cmp.QI1200 | | | C8-pos | 5.49 | 348.2895 | −2.66159 |
| QI3233 | | | HIL-pos | 3.9 | 241.0931 | −2.66157 |
| QI5758 | | | C18-neg | 1.58 | 529.9523 | −2.66132 |
| cmp.QI5007 | | | C8-pos | 8.72 | 774.0611 | −2.66094 |
| cmp.QI3043 | | | C8-pos | 4.81 | 592.3372 | −2.66079 |
| QI6660 | | | HIL-pos | 7.29 | 673.5276 | −2.65849 |
| QI103 | HMDB00182 | lysine | HIL-pos | 9.44 | 147.1128 | −2.65812 |
| cmp.QI5714 | | | C8-pos | 8.33 | 832.5843 | −2.65808 |
| QI4846 | | | C18-neg | 13.77 | 455.4102 | −2.6562 |
| QI4354 | | | C18-neg | 13.85 | 423.2205 | −2.65614 |
| QI4453 | | | C18-neg | 7.56 | 437.1612 | −2.65591 |
| QI6817 | | | C18-neg | 6.63 | 646.3203 | −2.65473 |
| QI4174 | | | C18-neg | 2.84 | 403.0153 | −2.65075 |
| QI858 | | | HIL-pos | 9.44 | 129.1025 | −2.64637 |
| QI4851 | | | C18-neg | 1.37 | 457.0367 | −2.64578 |
| QI518 | | | C18-neg | 1.37 | 127.0499 | −2.64564 |
| QI2433 | | | C18-neg | 1.32 | 259.0133 | −2.64508 |
| QI4428 | | | HIL-pos | 5.65 | 330.1395 | −2.64109 |
| QI4395 | | | C18-neg | 1.71 | 431.1189 | −2.63957 |
| QI6770 | | | HIL-pos | 7.47 | 705.9492 | −2.63862 |
| QI7164 | | | HIL-pos | 7.05 | 795.6353 | −2.63621 |
| QI6643 | | | HIL-pos | 1.99 | 668.5645 | −2.63618 |
| cmp.QI7068 | | | C8-pos | 11.51 | 994.7853 | −2.6358 |
| cmp.QI6414 | | | C8-pos | 8.38 | 896.5381 | −2.63423 |
| cmp.QI2821 | | | C8-pos | 4.57 | 568.3402 | −2.63214 |
| cmp.QI5943 | | | C8-pos | 8.19 | 854.5681 | −2.63006 |
| QI1077 | | | HIL-pos | 3.18 | 141.0183 | −2.62678 |
| QI1214 | | | HIL-pos | 3.51 | 146.0812 | −2.62599 |
| QI2837 | | | HIL-pos | 5.55 | 222.0971 | −2.62405 |
| QI1027 | | | HIL-pos | 4.63 | 138.0911 | −2.62157 |
| QI1438 | | | C18-neg | 2.05 | 197.0533 | −2.61617 |
| QI2286 | | | HIL-pos | 3.22 | 194.0483 | −2.61484 |
| QI3026 | | | HIL-pos | 3.75 | 229.0819 | −2.61119 |
| cmp.QI632 | | | C8-pos | 11.83 | 259.2419 | −2.61031 |
| cmp.QI1376 | | | C8-pos | 11.83 | 371.358 | −2.60918 |
| QI2028 | | | HIL-pos | 5.86 | 182.0483 | −2.60691 |
| cmp.QI4912 | | | C8-pos | 5.57 | 765.0885 | −2.60582 |
| QI3299 | | | C18-neg | 1.34 | 327.0007 | −2.60581 |
| QI402 | | | HIL-pos | 3.18 | 96.0086 | −2.60533 |
| cmp.QI6046 | | | C8-pos | 9.13 | 862.6297 | −2.60532 |

Predictor models using one or more biomarkers can be built using a variety of modeling approaches. The following few examples illustrate a few of those approaches.

Example 8: Building Predictor Models Via a Forward Selection Procedure

A multi-metabolite survival predictor model of all-cause mortality was built iteratively using forward selection procedures. First, the metabolite with the smallest P value in a CoxPH model adjusted for sex and smoking status was identified and included in the model as a first biomarker. Next, the metabolite leading to the greatest increase in marginal likelihood for the multivariate model including sex, smoking status, and the first metabolite. This process was repeated until addition of further metabolites as model biomarkers no longer provided significant improvement to the marginal likelihood of the model. For example, in one example model using only named metabolites, the process was repeated until addition of further metabolites no longer provided significant improvement to the marginal log-likelihood of the model (e.g., ≤2.94), using cross-validation for the named metabolite set.

When metabolites were thusly selected from the set of 13462 metabolites after the performance of data cleaning methods described in Example 6, forward selection yielded a survival predictor model with 29 metabolites (HR=2.16; Table 3):

TABLE 3

(HMDB ID: Human Metabolome Database ID, Method: LC-MS method where the metabolite was measured, RT: Retention Time, m/z: mass over charge.)

| Covariate (clinical factor) | Covariate (Compound) | HMDB ID | Metabolite | Method | RT | m/z | coefficient |
|---|---|---|---|---|---|---|---|
| gender | | | | | | | −0.23167 |
| smoking == 1 | | | | | | | 0.10436 |
| | cmp.QI2812 | | | C8-pos | 10.18 | 567.4561 | −0.22454 |
| | QI1972 | | | HIL-pos | 7.71 | 179.9824 | −0.28371 |
| | QI3594 | | | HIL-pos | 8.63 | 264.1191 | 0.40672 |
| | QI2564 | | | C18-neg | 1.04 | 271.9258 | −0.13188 |
| | QI5364 | | | C18-neg | 6.73 | 508.8756 | −0.14595 |
| | QI2775 | | | C18-neg | 3.6 | 291.0832 | −0.17825 |
| | QI7331 | | | C18-neg | 13.46 | 775.5957 | −0.17118 |
| | QI6382 | | | HIL-pos | 1.99 | 610.4678 | −0.21967 |
| | QI6239 | | | C18-neg | 8.36 | 582.8798 | −0.1463 |
| | QI2497 | | | C18-neg | 7.6 | 264.1294 | 0.21607 |
| | QI2802 | | | C18-neg | 11.1 | 293.2122 | −0.22997 |
| | cmp.QI5440 | | | C18-pos | 9.67 | 809.5872 | 0.10324 |
| | QI2885 | | | C18-neg | 11.14 | 299.2224 | 0.06289 |
| | QI2488 | | | HIL-pos | 5.42 | 203.0349 | −0.04935 |
| | cmp.QI1886 | | | C8-pos | 11.89 | 448.3567 | 0.09581 |
| | QI272 | | | C18-neg | 4.55 | 102.9553 | 0.08759 |
| | QI2555 | | | C18-neg | 12.18 | 271.2275 | 0.12081 |
| | QI3284 | | | HIL-pos | 6.35 | 244.0792 | −0.16008 |
| | QI4325 | | | C18-neg | 13.99 | 419.3033 | −0.07405 |
| | cmp.QI5937 | | | C8-pos | 11.37 | 853.6695 | 0.13649 |
| | cmp.QI6764 | | | C8-pos | 12.69 | 939.7772 | −0.00218 |
| | QI5574 | | | HIL-pos | 1.65 | 470.3838 | 0.02606 |
| | QI3278 | | | HIL-pos | 3.67 | 243.2067 | 0.017 |
| | cmp.QI221 | HMDB42103 | C49:3 TAG | C8-pos | 11.39 | 837.6939 | −0.19278 |
| | QI2804 | | | C18-neg | 11.96 | 293.2123 | −0.01353 |
| | QI5625 | | | HIL-pos | 1.72 | 479.4096 | −0.02232 |
| | QI1826 | | | HIL-pos | 1.66 | 172.1154 | −0.00374 |
| | QI7268 | | | C18-neg | 13.14 | 759.5652 | 0.00438 |
| | QI2494 | | | HIL-pos | 6.35 | 203.0526 | 0.08449 |

Example 9: Building predictor models via a forward selection procedure—using identified biomarkers Another multi-metabolite survival predictor model of all-cause mortality was built as described in Example 8, but limiting the eligible metabolites to the 536 metabolites whose chemical identities were known. A survival predictor model with four metabolite biomarkers was created (HR=1.9; Table 4):

TABLE 4

(HMDB ID: Human Metabolome Database ID, Method: LC-MS method where the metabolite was measured, RT: Retention Time, m/z: mass over charge.)

| Covariate | Compound | HMDB ID | Metabolite | Method | RT | m/z | coefficient |
|---|---|---|---|---|---|---|---|
| Gender | | | | | | | −0.42865 |
| smoking == 1 | | | | | | | 0.38743 |
| | TF63 | HMDB00186 | lactose/sucrose/trehalose | HILIC-neg | 2.45 | 341.1089 | 0.10675 |
| | QI11 | HMDB01906 | alpha-Aminoisobutyric acid | HIL-pos | 7.71 | 104.0711 | −0.39948 |
| | TF42 | HMDB00127 | Glucuronate | HILIC-neg | 5 | 193.0354 | 0.32989 |
| | TF66 | HMDB02108 | Methylcysteine | HILIC-neg | 3.45 | 134.0281 | −0.09203 |

Example 10: Building Predictor Models that Utilize Sets of n Biomarkers Selected from a List of Metabolites that Associate Significantly with all-Cause Mortality Sets of n individually significant metabolites were used to build high-performing survival predictor models, wherein n was as low as 1. At a false discovery rate of 5%, the 661 metabolites identified as described in Example 6 (Table 1) were used alone or in combination to build the multiple different survival predictor models. Such survival predictor models were shown to robustly predict mortality. Subsets of n metabolites were randomly selected from the 661 metabolites in Table 1. For each subset size n, a survival predictor model was fit and was used to score a HR. This procedure was repeated 100 times for each n between 1 and 20

Figure 3:
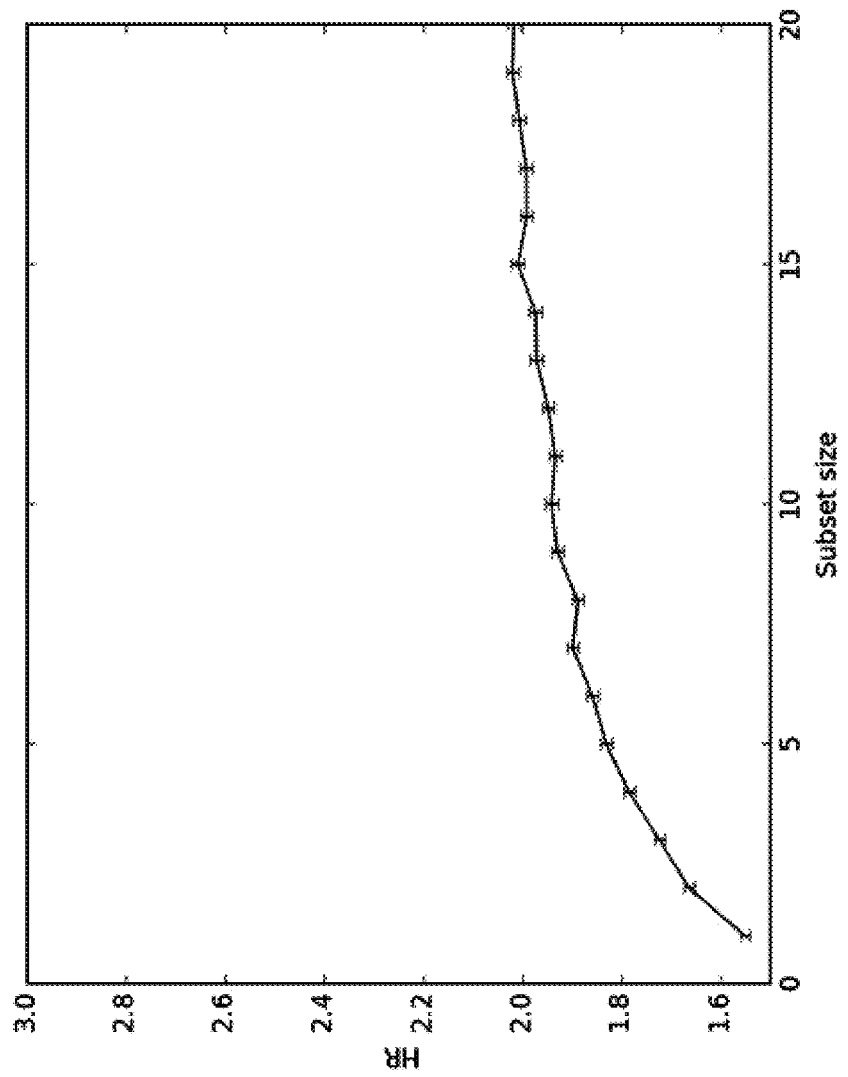
FIG. 3 illustrates the results from survival predictor models built using subsets of metabolites having size n from n=1 to 20 selected randomly from a set of 661 metabolites that are shown to associate significantly with survival.
Figure 4:
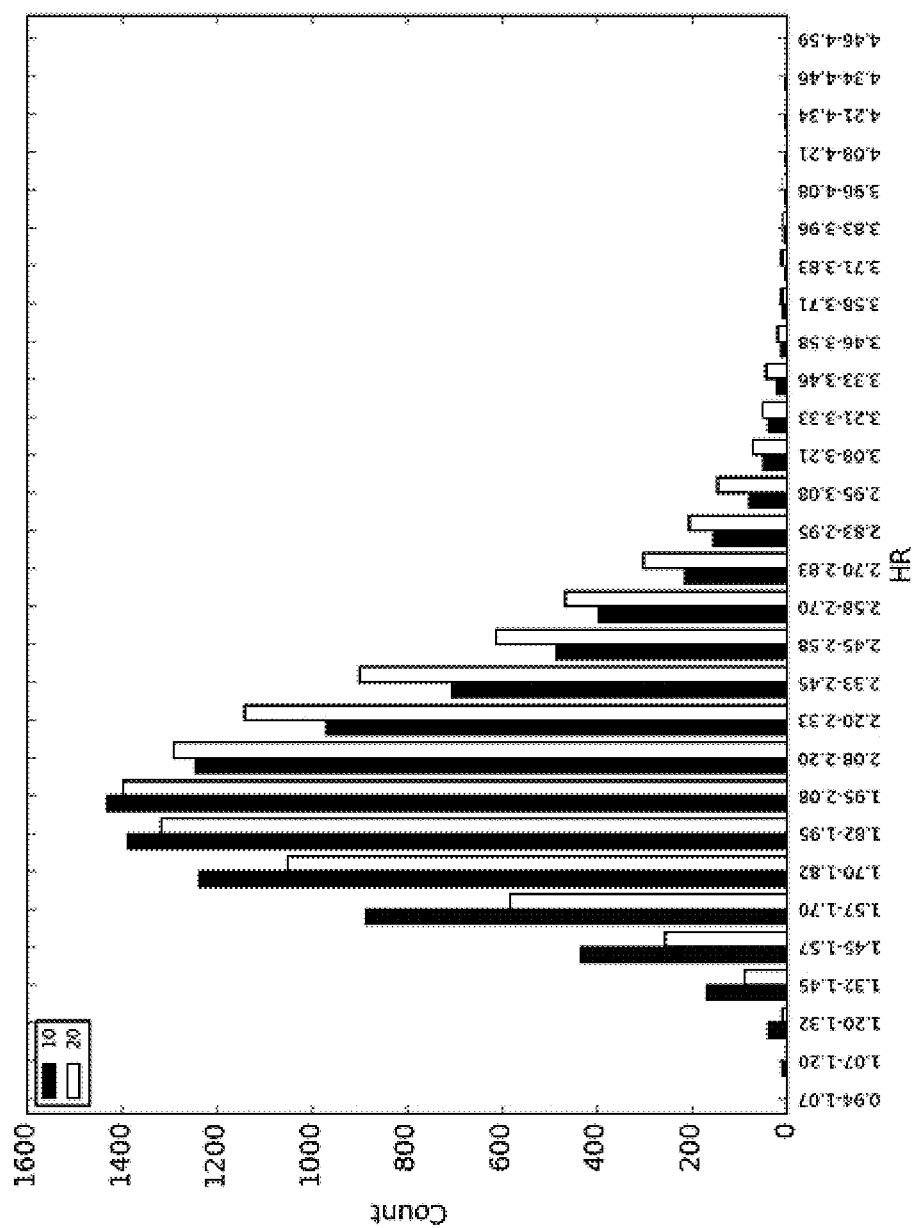
FIG. 4 illustrates the distribution of predictive performance for 1000 survival predictor models built from 10 (black) or 20 (white) randomly chosen from a set of 661 metabolites that are shown to associate significantly with survival.

Multimarker survival predictor models thusly created show improved performance compared to using only one marker, with survival predictor models including 10 or more metabolites attaining HRs near 2 (FIGS. 3 and 4). For example, FIG. 3 shows the results for each n from n=1 to 20 for 661 metabolites. To estimate the generalization performance of each survival predictor model, all HRs were calculated using nested 5-fold cross-validation. For each repeat, for each survival predictor model of n metabolites, the data was split into training and testing sets (at 80%/20%, in a balanced way, keeping the ratio of deaths to censored events the same). Then, within the training set, another 5-fold CV was used to select the regularization coefficient, using regularized CoxPH regression with objective function $$\lambda\|\beta\|^2 + \sum_{i:C_i=1} \log\theta_i - \log\left(\sum_{j:Y_j \geq Y_i} \theta_j\right)$$

as discussed above. The chosen coefficient was then used to fit weights on the entire training set (80% of the full data), and these weights were evaluated on the test set using a Bayesian method, also as described above. Using a prior of N(0, 1) over the log of the hazard ratio (HR), the posterior distribution using the Cox PH likelihood function was identified and, then, the posterior mean of the log-HR was calculated.

As shown in FIG. 3, subsets of size n=1 to 20 of the 661 metabolites are predictive for all-cause mortality. The HR of a typical survival predictor model increases with increasing subset size to reach ~2 for survival predictor models built from 10 or more significant metabolites.

FIG. 4 illustrates the distribution of predictive performance for 1000 survival predictor models built from 10 (blue) or 20 (red) randomly chosen significant metabolites. The histograms for n=10 and n=20 are both quite narrow and the values for HR for are significantly greater than 1 in a significant proportion of the cases. While some subsets provide survival predictor models with greater strength than others, in a majority of the tested subsets, HR is even greater than 2.

Example 11: Machine Learning Methods to Build Predictor Models of Mortality

Many alternative approaches of machine learning can be used to build predictor models based on survival biomarkers of mortality based on metabolome data. This is illustrated using the example of a ranking-based regularized survival Support Vector Machines (SVM) as described above and in further detail by Pölsterl et al. (S. Pösterl, N. Navab, A. Katouzian. 2015. Fast Training of Support Vector Machines for Survival Analysis. Machine Learning and Knowledge Discovery in Databases), which is herein incorporated by reference in its entirety.

The following procedure was repeated 1000 times: (1) A balanced split (comprising approximately the same fraction of death and non-death events in each bucket) was randomized setting aside 80% of the data for a training set and 20% testing set. (2) Then forward stepwise variable selection on the training set was performed, using PH marginal likelihood as described in Example 8. (3) Using the selected variables from step 2, weights were fit using a survival SVM using a rank-based approach described in further detail above. The regularization coefficient was chosen by another 5-fold cross-validation within the 80% training set (nested cross-validation), using a grid search. Using the best value, weights were fit on the entire training set (80% of the entire data) and used those weights for evaluation on the 20% test set.

While a survival predictor model only using only age, gender, smoking status, alcohol consumption status, height, weight, BMI, and systolic and diastolic blood pressure as covariates has a log-HR of 0.37857 (±0.01753), with Harrell's concordance index c=0.61912 (±0.002501), using the same covariates along with the metabolites selected in step (2) resulted in a survival predictor model having a log-HR of 0.59063 (±0.01805), Harrell's concordance index c=0.65454 (±0.002544). Building a model using only the metabolites selected in step (2) resulted in a survival predictor model having a log-HR 0.58454 (±0.01798), with Harrell's concordance index c=0.66406 (±0.002646). These numbers are comparable to the results using regularized Cox PH for the Examples described herein.

Example 12: Building a Survival Predictor Model Using Elastic-Net Regularized CoxPH Regression A multi-metabolite survival predictor model of all-cause mortality was built using elastic net regression. A CoxPH objective function was used and elastic-net regression via coordinate descent, as described above, was applied as provided in glmnet package for R ("Package 'glmnet'," CRAN, Maintainer: Trevor Hastie, Mar. 17, 2016, 23 pages). Regularization parameter was selected using 16-fold cross validation.

When metabolites were thusly selected from the set of 13462 metabolites after the performance of data cleaning methods described in Example 6, a survival predictor model was obtained with 77 metabolites (HR=2.05; Table 5).

TABLE 5

| Covariate | Coefficient | Method | RT | m/z |
|---|---|---|---|---|
| Gender | −0.2069312678 | N/A | N/A | N/A |
| smoking | 0.06483616074 | N/A | N/A | N/A |
| Age | 0.1173871942 | N/A | N/A | N/A |
| QI1972 | −0.2047705722 | HIL-pos | 7.71 | 179.9824 |
| cmp.QI2539 | −0.1597988224 | C8-pos | 10.18 | 536.4373 |
| QI3960 | −0.1505062782 | C18-neg | 7.37 | 386.9168 |
| QI1441 | −0.1351625434 | C18-neg | 2.38 | 197.0534 |
| QI5409 | −0.09378337047 | C18-neg | 7.64 | 511.2902 |
| QI4516 | −0.08456583129 | HIL-pos | 4.41 | 338.057 |
| cmp.QI4994 | −0.08353595673 | C8-pos | 8.93 | 772.5239 |
| QI5128 | −0.07108098199 | C18-neg | 12.35 | 479.3375 |
| QI2665 | −0.06309333367 | C18-neg | 1.01 | 283.9941 |
| cmp.QI6058 | −0.05957184686 | C8-pos | 10.02 | 863.6975 |
| QI2564 | −0.05581574505 | C18-neg | 1.04 | 271.9258 |

TABLE 5-continued

| Covariate | Coefficient | Method | RT | m/z |
|---|---|---|---|---|
| QI5602 | -0.05368942907 | HIL-pos | 2.42 | 475.2974 |
| QI6039 | -0.04879942478 | C18-neg | 11.3 | 568.3394 |
| QI6382 | -0.04812534999 | HIL-pos | 1.99 | 610.4678 |
| QI576 | -0.04800087031 | HIL-pos | 2.13 | 112.0954 |
| QI4796 | -0.0467482007 | HIL-pos | 7.09 | 364.3092 |
| QI5358 | -0.04362508403 | C18-neg | 8.36 | 508.8755 |
| QI6459 | -0.03747240984 | HIL-pos | 1.92 | 624.4469 |
| QI3274 | -0.03613646804 | C18-neg | 6.72 | 324.9466 |
| QI1660 | -0.03602388275 | C18-neg | 5.6 | 213.0218 |
| QI864 | -0.03585571253 | HIL-pos | 8.66 | 130.0499 |
| QI6489 | -0.03309227431 | C18-neg | 10.22 | 595.2467 |
| QI6526 | -0.02724829622 | C18-neg | 8.65 | 596.896 |
| QI2263 | -0.02533386375 | HIL-pos | 1.98 | 193.086 |
| cmp.QI7188 | -0.0244497634 | C8-pos | 13.68 | 1037.2847 |
| QI2930 | -0.02419366647 | HIL-pos | 8.01 | 225.0524 |
| QI893 | -0.02224009294 | HIL-pos | 4.55 | 131.0705 |
| QI1919 | -0.02182802691 | HIL-pos | 8.39 | 132.1019 |
| QI6118 | -0.01791510368 | C18-neg | 4.1 | 576.8633 |
| QI1576 | -0.01712396848 | HIL-pos | 10.51 | 161.1285 |
| QI888 | -0.01614559069 | HIL-pos | 8.11 | 131.0533 |
| cmp.QI5316 | -0.01535321732 | C8-pos | 9.23 | 800.556 |
| cmp.QI5750 | -0.01484609225 | C8-pos | 9.61 | 834.7448 |
| QI2265 | -0.0144827442 | HIL-pos | 2.02 | 193.0862 |
| cmp.QI5917 | -0.01247244611 | C8-pos | 9.32 | 851.6254 |
| cmp.QI2922 | -0.01226190873 | C8-pos | 6.17 | 578.4181 |
| QI3284 | -0.01178966716 | HIL-pos | 6.35 | 244.0792 |
| QI2719 | -0.009655773295 | C18-neg | 5.28 | 285.9895 |
| QI5485 | -0.00829521714 | C18-neg | 1.85 | 457.3312 |
| QI5755 | -0.007972588128 | C18-neg | 1.54 | 529.952 |
| QI5110 | -0.006770256955 | HIL-pos | 1.72 | 402.2638 |
| cmp.QI5002 | -0.006192862664 | C8-pos | 10.95 | 773.6192 |
| QI1434 | -0.005863047928 | HIL-pos | 2.13 | 155.1542 |
| QI1588 | -0.005279089539 | C18-neg | 1.77 | 207.9304 |
| QI4673 | -0.004532693406 | C18-neg | 8.45 | 452.9224 |
| QI5479 | -0.004168660075 | HIL-pos | 1.67 | 455.3731 |
| QI5481 | -0.003647308371 | C18-neg | 6.2 | 520.9094 |
| QI7619 | 0.002575476308 | C18-neg | 18.76 | 847.5821 |
| QI282 | 0.002973056759 | C18-neg | 1.7 | 102.9553 |
| QI4303 | 0.003942640633 | HIL-pos | 11.84 | 318.191 |
| QI2606 | 0.004260968946 | HIL-pos | 5.47 | 208.072 |
| QI6741 | 0.004927249308 | HIL-pos | 3.21 | 698.5561 |
| QI7394 | 0.005891446252 | C18-neg | 11.41 | 788.5454 |
| QI2293 | 0.006195662155 | C18-neg | 1.03 | 256.0667 |
| QI5699 | 0.00727543678 | HIL-pos | 2.39 | 491.3481 |
| cmp.QI1171 | 0.01247984416 | C8-pos | 5.43 | 341.3049 |
| QI1991 | 0.0140174639 | C18-neg | 9.88 | 230.9553 |
| QI3340 | 0.0168601081 | C18-neg | 8.5 | 329.2332 |
| QI3635 | 0.01719007958 | HIL-pos | 4.18 | 267.0587 |
| QI805 | 0.01724001794 | HIL-pos | 4.55 | 126.0222 |
| QI3032 | 0.02096997599 | HIL-pos | 9.17 | 229.1183 |
| cmp.QI4319 | 0.02139528163 | C8-pos | 8.07 | 706.8607 |
| QI2773 | 0.02330354476 | HIL-pos | 2.56 | 218.0811 |
| QI1071 | 0.02649469096 | C18-neg | 16.28 | 162.981 |
| QI4626 | 0.02654684158 | C18-neg | 13.67 | 449.3125 |
| QI689 | 0.02791886126 | HIL-pos | 8.24 | 118.1229 |
| cmp.QI2650 | 0.03016591137 | C8-pos | 8.95 | 550.2176 |
| QI3933 | 0.03045371413 | HIL-pos | 10.37 | 287.2442 |
| QI3053 | 0.03486645406 | C18-neg | 12.47 | 313.1738 |
| QI2356 | 0.03620383423 | HIL-pos | 4.52 | 198.0431 |
| QI2497 | 0.04193601958 | C18-neg | 7.6 | 264.1294 |
| cmp.QI333 | 0.04918882013 | C8-pos | 3.33 | 205.1223 |
| QI370 | 0.05286321264 | HIL-pos | 8.78 | 90.5263 |
| cmp.QI6887 | 0.05321055063 | C8-pos | 14.18 | 960.7727 |
| QI3569 | 0.06833954134 | C18-neg | 15.46 | 341.197 |
| QI1322 | 0.1065168958 | HIL-pos | 4.84 | 151.0615 |
| cmp.QI3003 | 0.1480090268 | C8-pos | 7.65 | 588.3547 |

Method: LC-MS method where the metabolite was measured,
RT: Retention Time,
m/z: mass over charge.

Figure 2:
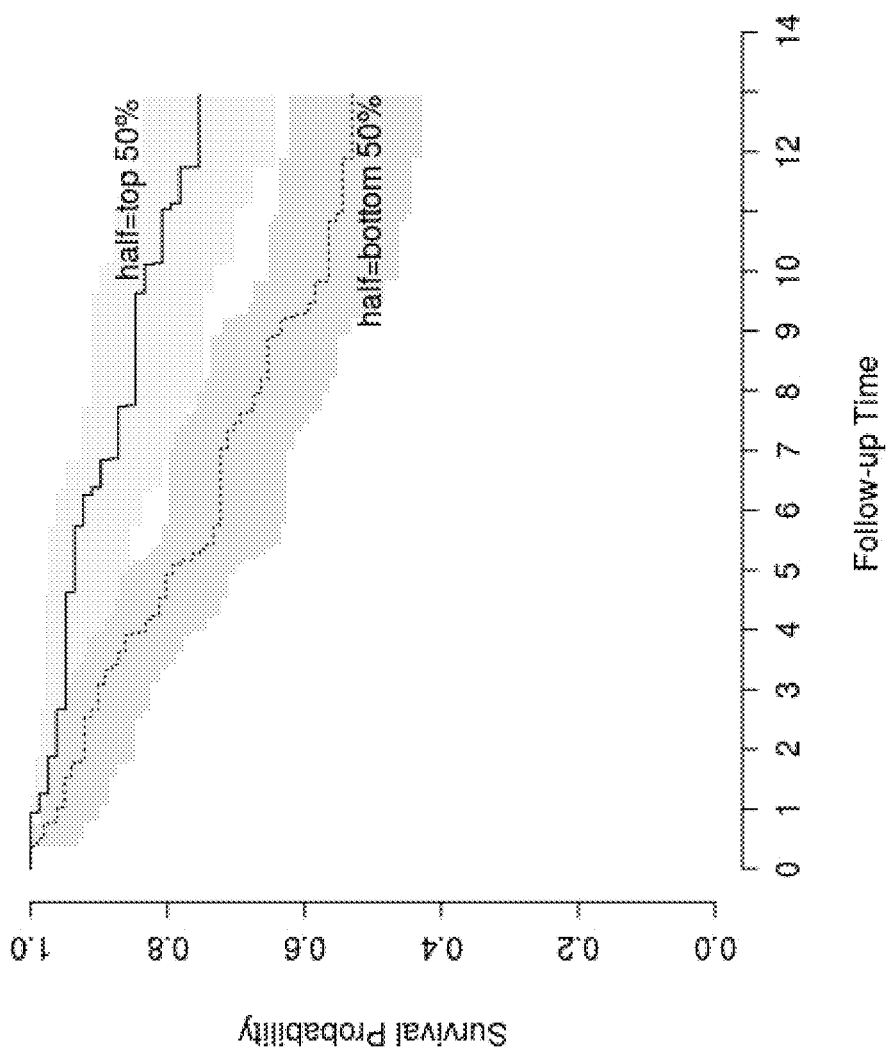
FIG. 2 illustrates a survival curve example for a survival predictor model built using elastic-net regularized CoxPH regression using identified biomarkers.

Example 13: Building a Survival Predictor Model Using Elastic-Net Regularized CoxPH Regression—Using Identified Biomarkers Another multi-metabolite survival predictor model of all-cause mortality was built as described in Example 12, but limiting the eligible metabolites to the 536 metabolites whose chemical identities were known. A survival predictor model with 29 metabolite biomarkers was created (HR=2.02; Table 5). FIG. 2 shows the survival curve example for this model.

TABLE 6

| Covariate | Coefficient | Compound | HMDB ID | Method | RT | m/z |
|---|---|---|---|---|---|---|
| Gender | -0.2407700376 | N/A | N/A | N/A | N/A | N/A |
| smoking | 0.1179636523 | N/A | N/A | N/A | N/A | N/A |
| Age | 0.1818226474 | N/A | N/A | N/A | N/A | N/A |
| alpha-Aminoisobutyric acid | -0.2511342249 | QI11 | HMDB01906 | HIL-pos | 7.71 | 104.0711 |
| C38:6 PE plasmalogen | -0.0959423146 | cmp.QI78 | HMDB11387 | C8-pos | 8.86 | 750.5431 |
| C20:5 CE | -0.08794966031 | cmp.QI123 | HMDB06731 | C8-pos | 11.43 | 693.5575 |
| pyroglutamic acid | -0.07426418998 | TF20 | HMDB00267 | HIL-pos | 8.11 | 130.0501 |
| Cholate | -0.06886603208 | QI17 | HMDB00619 | C18-neg | 8.81 | 407.28 |
| indole-3-propionate | -0.06486408484 | TF55 | HMDB02302 | HILIC-neg | 4.45 | 188.0717 |
| C54:10 TAG | -0.06000997636 | cmp.TF08 | NA | C8-pos | 9.8 | 893.6624 |
| C3 carnitine | -0.04780197155 | QI63 | HMDB00824 | HIL-pos | 8.36 | 218.1386 |
| Fucose | -0.03701347721 | TF38 | HMDB00174 | HILIC-neg | 1.4 | 163.0612 |
| C36:5 PC plasmalogen-A | -0.03066867766 | cmp.QI47 | HMDB11221 | C8-pos | 8.49 | 766.5733 |
| C40:10 PC | -0.0281424687 | cmp.QI38 | HMDB08511 | C8-pos | 8.05 | 826.5353 |
| xanthine | -0.0131582493 | QI139 | HMDB00292 | HIL-pos | 3.83 | 153.0408 |
| kynurenic acid | -0.01178016086 | QI101 | HMDB00715 | HIL-pos | 5.27 | 190.0499 |
| C40:7 PE plasmalogen | -0.009925220731 | cmp.QI81 | HMDB11394 | C8-pos | 9.11 | 776.5583 |
| Sphinganine | -0.009906364648 | QI129 | HMDB00269 | HIL-pos | 5.82 | 302.3053 |
| 1-Methylhistidine | -0.00970127114 | QI3 | HMDB00001 | HIL-pos | 9.89 | 170.0925 |
| 4-pyridoxate | -0.008981809696 | TF12 | HMDB00017 | HILIC-neg | 3.65 | 182.0459 |
| sphingosine | -0.007209210402 | QI130 | HMDB00252 | HIL-pos | 2 | 300.2897 |
| Dodecanedioic acid | -0.004624925846 | QI31 | HMDB00623 | C18-neg | 7.74 | 229.1439 |
| Eicosapentaenoic acid | -5.86E-04 | QI12 | HMDB01999 | C18-neg | 13.37 | 301.217 |
| 1-Methyladenosine | 0.006427303351 | QI1 | HMDB03331 | HIL-pos | 7.74 | 282.1195 |
| thymine | 0.01228195906 | TF84 | HMDB00262 | HILIC-neg | 1.35 | 125.0357 |
| Oxalate | 0.01606664837 | TF68 | HMDB02329 | HILIC-neg | 7.4 | 88.988 |
| N-Acetylleucine | 0.02103147479 | QI109 | HMDB11756 | HIL-pos | 2.81 | 174.1126 |
| C36:2 PS plasmalogen | 0.0250547032 | cmp.QI88 | NA | C8-pos | 7.8 | 774.5639 |
| Pseudouridine | 0.07674826015 | QI123 | HMDB00767 | HIL-pos | 4.28 | 245.0768 |

TABLE 6-continued

| Covariate | Coefficient | Compound | HMDB ID | Method | RT | m/z |
|---|---|---|---|---|---|---|
| C16:1 CE | 0.08055357068 | cmp.QI111 | HMDB00658 | C8-pos | 11.75 | 645.5577 |
| 6-8-Dihydroxypurine | 0.1252990398 | QI10 | HMDB01182 | HIL-pos | 4.44 | 153.0408 |
| glucuronate | 0.1619548867 | TF42 | HMDB00127 | HILIC-neg | 5 | 193.0354 |

Example 14: Methods

Framingham Offspring study cohort

In order to study metabolites that are associated with aging, study cohorts were designed. Study subjects were drawn from the Offspring cohort of the Framingham Heart Study (Thomas R. Dawber, Gilcin F. Meadors, and Felix E. Moore, Jr. Cohort Profile: Framingham Heart Study, of the National Heart, Lung, and Blood Institute and Boston University. Am J Public Health Nations Health. first published March 1951 as "Epidemiological Approaches to Heart Disease: The Framingham Study" at www.ncbi.nlm.nih.gov/pmc/articles/PMC1525365/). Members of the Offspring cohort of the Framingham Heart Study began to be enrolled in 1971 and in-person evaluations occurred approximately every 4 to 8 years afterward. The members of the study used for the following analyses were determined as follows. Initially, subjects used for the study were all members of the Offspring cohort of the Framingham Heart Study who survived until the fifth examination cycle, occurring from 1987 to 1991, provided written informed consent for metabolomics research, and consented to sharing their metabolomics data with for-profit companies. These subjects comprise 1,479 individuals with a mean age of 53.7 years (standard deviation 9.2) and for whom 306 deaths have been recorded.

TwinsUK Study Cohort

The TwinsUK study cohort was designed as follows. Study subjects were drawn from the TwinsUK cohort (Tim D. Spector and Frances M. K. Williams, "The UK Adult Twin Registry (TwinsUK)", *Twin Research and Human Genetics* Volume 9 Issue 6, 1 Dec. 2006, pp. 899-906). Members of the TwinsUK began to be enrolled in 1992. The members of the cohort used for the following analyses were the members for whom metabolomic analysis was performed. In certain cases described below, the subset of the cohort analyzed was limited to those individuals for whom certain measurements were taken, for whom certain types of metabolomic data were measured, or based on other criteria, without limitation. In particular, glucuronate levels were measured for 2069 members of the TwinsUK cohort, and measurements of systolic and diastolic blood pressure were only taken for 1996 members of those 2069 people, so some of the analyses performed, which rely on measurements of both glucuronate levels and blood pressure, were performed on the aforementioned subset of 1996 members of the TwinsUK cohort.

Metabolomics Protocols

Blood samples from study cohort members were analyzed with metabolomics profiling platforms. A combination of three different LC-MS methods were used, wherein each LC-MS method measured complementary sets of metabolite classes, ranging from polar metabolites, such as organic acids, to non-polar lipids, such as triglycerides. In each method, the MS data were acquired using sensitive, high resolution mass spectrometers (e.g., Q Exactive, Thermo Scientific) that enabled measurement of certain metabolites of known identity. The three LC-MS methods are summarized as follows:

Amino acids, amino acids derivatives, urea cycle intermediates, nucleotides, and polar metabolites that ionize in the positive ion mode. In this LC-MS method, polar metabolites were extracted and separated using a hydrophilic interaction liquid chromatographic (HILIC) column under acidic mobile phase conditions, specifically mixtures of ammonium formate with formic acid and acetonitrile with formic acid. Suitable metabolites for this method include, without limitation, tyrosine, serine, adenine, and guanine.

Polar and non-polar lipids. In this LC-MS method, lipids were extracted with isopropanol and separated using reverse phase chromatography with a C4 column. Suitable lipids for this method include, without limitation, triglycerides, sphingomyelins, cholesteryl ethers, phosphatidylcholines, phosphatidylcholine plasmalogens, and lysophosphatidylethanolamines.

Free fatty acids, bile acids, and metabolites of intermediate polarity. In this LC-MS method, metabolites were extracted with a mixture of methanol and water and separated using reverse chromatography on a Luna N12 column. Suitable lipids for this method include, without limitation, citrate, adipic acid, glucuronate, isocitrate, and lactate.

LC-MS Data Processing

Metabolite relative quantification and identification relied on a panel of the three LC-MS methods described above that generated raw data files of high resolution mass spectra acquired over time. In each raw data file, LC-MS data peaks were detected and integrated using computer software (for example, but not limited to, Progenesis CoMet software). Identification was conducted by matching measured retention time and masses to databases.

Quality Control

The quality of the data processed is checked with two methods. First, synthetic internal standards were monitored and used to normalize peak area for metabolite data. Second, pooled plasma reference samples were periodically analyzed to measure and correct for temporal drift.

Framingham Offspring Study Cohort Sample Collection

Blood samples from the 1,479 Framingham Offspring cohort members who were selected as described above were collected after an overnight fast during the fifth examination cycle, which occurred from 1987 to 1991. Blood samples were centrifuged and stored at negative 80 degrees Celsius immediately after collection and until further analysis or assaying.

TwinsUK Study Cohort Sample Collection

Blood samples from certain members of the TwinsUK cohort were collected after an overnight fast. Blood samples were sent to Metabolon Inc. (Durham, USA) for analysis. Sample collection was performed with methods known to those skilled in the art, including, without limitation, the methods used in the Framingham Offspring Cohorts described above and Estonian Biobank Cohorts described in Examples 1-5.

Example 15: Building a Survival Predictor Model

Survival predictor models can also be built with a single metabolite. The identification of a single metabolites, comprising glucuronate (also known as glucuronic acid), can be used to construct a survival predictor model and the validation of its utility in constructing survival predictor models.

To identify individual metabolites which can be used to construct survival predictor models, the Estonian Biobank described in Examples 1-3 and the Framingham Offspring cohorts described in Example 14 were used. For every non-lipid metabolite available in the data for the Estonian Biobank and Framingham Offspring cohorts, its utility for constructing survival predictor models was measured with the following procedure: (1) The values of the metabolite were controlled for available covariates, including: age at time of blood sample collection, sex, body mass index, systolic blood pressure, and diastolic blood pressure. (2) A linear Cox regression model for all-cause mortality risk in terms of the levels of the metabolite alone was constructed using data from the Estonian biobank cohort (3) The p-value associated with a statistical test of the null hypothesis that the metabolite has no relationship with mortality risk was recorded. When this procedure was completed for every such metabolite, the false discovery rates (FDRs) were calculated corresponding to the p-values using the method of Benjamini and Hochberg. The regression models found four metabolites to be associated with all-cause mortality risk at FDR<0.05, namely glucuronate, lysine, histidine, and glutamine (Tables 6 and 7).

Table 7

(Metabolite: The identity of the metabolite in the Estonian Biobank data. Coefficient: The coefficient associated with the metabolite in a Cox proportional hazards regression model for all-cause mortality risk. Hazard ratio: The hazard ratio associated with the coefficient was calculated by raising the mathematical constant e to the power of the coefficient. Standard error of coefficient is the standard error of the coefficient of the metabolite in the Cox proportional hazards model for all-cause mortality risk. P-value: The p-value associated with a statistical test for the null hypothesis of no relationship between the metabolite and all-cause mortality risk. False discovery rate: The false discovery rate associated with the p-value of the metabolite. The rows of the table are restricted to those for which FDR<0.05.)

hypothesis used in the statistical test for calculating p-values was that the coefficient is equal to or less than 0 (i.e., a one-sided test was used). Separate regression models were generated for each metabolite. The regression models collectively indicated a single metabolite, glucuronate, to be associated with all-cause mortality in the Estonian Biobank data at FDR<0.05 and in the Framingham Offspring data at FDR<0.1.

Table 8

(Metabolite: The identity of the metabolite in the Framingham Offspring data. Coefficient: The coefficient associated with the metabolite in a Cox proportional hazards regression model for all-cause mortality risk. Hazard ratio: The hazard ratio associated with the coefficient, calculated by raising the mathematical constant e to the power of the coefficient. Standard error of coefficient: The standard error of the coefficient of the metabolite in the Cox proportional hazards model for all-cause mortality risk. P-value: The p-value associated with a statistical test for the null hypothesis of no negative relationship between the metabolite and all-cause mortality risk. False discovery rate: The false discovery rate associated with the p-value of the metabolite.)

TABLE 8

| Metabolite | Coefficient | Hazard ratio | Standard error of coefficient | P-value | False discovery rate |
|---|---|---|---|---|---|
| glucuronate | 0.139543 | 1.149748 | 0.066431 | 0.01784 | 0.071358 |
| lysine | −0.09047 | 0.9135 | 0.066908 | 0.088158 | 0.176315 |
| histidine | −0.02268 | 0.977577 | 0.066723 | 0.366969 | 0.366969 |
| glutamine | −0.03428 | 0.966305 | 0.068008 | 0.307132 | 0.366969 |

To validate the utility of glucuronate in the construction of survival predictor models, the TwinsUK cohort was also used. The subset of cohort members was restricted for whom glucuronate levels were measured and for whom the clinical covariates controlled for in the aforementioned analyses of the Estonian Biobank and Framingham Offspring datasets were measured. Glucuronate levels were controlled for those covariates as well as for family relatedness between individuals of the cohort and created a Cox proportional hazards regression model for all-cause mortality risk in terms of glucuronate levels, finding it to be significantly positively associated with mortality at FDR<0.05 (Coefficient=0.224526, Hazard ratio=1.251729, Standard error of coefficient=0.106099, One-sided p-value=False discovery rate=0.01715).

Example 16: Building a Survival Predictor Model Using Lipids

Survival predictor models can also be built with a class or subclass of metabolites. The construction and validation of

TABLE 7

| Metabolite | Coefficient | Hazard ratio | Standard error of coefficient | P-value | False discovery rate |
|---|---|---|---|---|---|
| glucuronate | 0.351427 | 1.421093 | 0.086542 | 4.89E−05 | 0.003913 |
| lysine | −0.30027 | 0.740615 | 0.085532 | 4.47E−04 | 0.016878 |
| histidine | −0.29378 | 0.745438 | 0.085974 | 6.33E−04 | 0.016878 |
| glutamine | −0.27299 | 0.761098 | 0.088599 | 0.002062 | 0.04123 |

For the metabolites in the Estonian Biobank data found to significantly associate with all-cause mortality risk at FDR 0.05 or below, the same procedure was used to determine their associations with all-cause mortality risk in the Framingham Offspring data, with the difference that the null the utility of survival predictor models was built using the subset of lipid metabolites in the Estonian Biobank cohort data, as described in Examples 1-5.

The metabolite features measured in the C8-positive mode were used, which, as described above, measures the levels of lipids. Additionally, the metabolite features were restricted to those with names containing any of "MAG", "DAG", "TAG", "PE", "PC", "PI", "PS", "Ceramide", or "CE", which are abbreviations denoting a metabolite's identity as a member of a particular subclass of lipids. Metabolite data corresponding to different adducts of a single metabolite, as well as metabolite data labeled "minor" which were highly correlated to their non-minor counterparts, were aggregated via summing. This process yielded 251 columns of metabolite data. Subsequently, metabolite data were normalized and controlled for clinical covariates (e.g., sex, age, smoking status, BMI, systolic blood pressure, and diastolic blood pressure), as described in Example 15.

For each of the 251 lipid metabolites, an independent linear Cox proportional hazards model for all-cause mortality was constructed. A set of 37 lipid metabolites were found to be significantly associated with all-cause mortality risk at FDR<0.05 (Table 8). The set of 37 lipid metabolites was disproportionately enriched in plasmalogens and deficient in TAGs.

Table 9

(Metabolite: The identity of a lipid metabolite in the Estonian dataset. Log(Hazard ratio): The logarithm of the hazard ratio associated with the metabolite in a Cox proportional hazards model for all-cause mortality. Hazard ratio: The hazard ratio associated with the metabolite in a Cox proportional hazards model for all-cause mortality. Se(log(Hazard ratio)): The standard error of the logarithm of the hazard ratio associated with the metabolite in a Cox proportional hazards model for all-cause mortality. P-value: The p-value associated with a statistical test for the significance of the association between the lipid metabolite and all-cause mortality risk. FDR: The false discovery rate associated with the corresponding p-value).

TABLE 9

| Metabolite | log(Hazard ratio) | Hazard ratio | se(log(Hazard ratio)) | P-value | FDR |
|---|---|---|---|---|---|
| C14:0 CE | −0.05312 | 0.948265 | 0.085619 | 0.53497 | 0.77617 |
| C14:0 LPC | −0.06302 | 0.938921 | 0.087376 | 0.470727 | 0.740483 |
| C14:0 LPC-A | −0.05048 | 0.950773 | 0.087611 | 0.564496 | 0.787159 |
| C14:0 LPC-B | −0.04483 | 0.956157 | 0.087465 | 0.608239 | 0.816407 |
| C14:0 MAG | −0.03868 | 0.962055 | 0.087538 | 0.658558 | 0.854152 |
| C15:0 LPC | −0.13209 | 0.87626 | 0.087946 | 0.133103 | 0.337464 |
| C16:0 Ceramide (d18:1) | 0.064014 | 1.066107 | 0.087404 | 0.463927 | 0.740483 |
| C16:0 LPC | −0.04075 | 0.96007 | 0.089992 | 0.650692 | 0.850644 |
| C16:0 LPE | 0.010743 | 1.0108 | 0.08657 | 0.901244 | 0.948626 |
| C16:1 CE | 0.162899 | 1.176917 | 0.086938 | 0.060966 | 0.204033 |
| C16:1 LPC | 0.10761 | 1.113614 | 0.087437 | 0.218426 | 0.472629 |
| C16:1 LPC plasmalogen | −0.16678 | 0.846384 | 0.087085 | 0.055473 | 0.193384 |
| C16:1 MAG | 0.036024 | 1.036681 | 0.086844 | 0.678279 | 0.854152 |
| C17:0 LPC | −0.14909 | 0.861494 | 0.087615 | 0.088825 | 0.262295 |
| C18:0 CE | −0.14996 | 0.860739 | 0.086171 | 0.081806 | 0.247388 |
| C18:0 LPC | −0.12442 | 0.883006 | 0.089192 | 0.163014 | 0.389682 |
| C18:0 LPC plasmalogen-A | −0.04532 | 0.955695 | 0.087486 | 0.604466 | 0.81615 |
| C18:0 LPC-plasmalogen-A | −0.02757 | 0.972808 | 0.088479 | 0.75536 | 0.891925 |
| C18:0 LPC-plasmalogen-B | 0.030941 | 1.031424 | 0.086571 | 0.720791 | 0.8698 |
| C18:0 LPE | 0.010236 | 1.010288 | 0.086605 | 0.905918 | 0.948626 |
| C18:1 CE | −0.15022 | 0.86052 | 0.08415 | 0.074243 | 0.230061 |
| C18:1 LPC | −0.05784 | 0.9438 | 0.087957 | 0.510792 | 0.763148 |
| C18:1 LPC plasmalogen-B | 0.020802 | 1.02102 | 0.086954 | 0.810926 | 0.925193 |
| C18:1 LPE | −0.01624 | 0.983894 | 0.088245 | 0.854009 | 0.948626 |
| C18:2 CE | −0.3049 | 0.737199 | 0.088563 | 5.76E−04 | 0.008416 |
| C18:2 LPC | −0.20884 | 0.811524 | 0.090026 | 0.020353 | 0.104258 |
| C18:2 LPE | 0.05794 | 1.059651 | 0.089041 | 0.515233 | 0.765228 |
| C18:3 CE | −0.09955 | 0.905244 | 0.085462 | 0.244078 | 0.498078 |
| C18:3 LPC | −0.12445 | 0.88298 | 0.08886 | 0.161351 | 0.389415 |
| C20:0 LPE | −0.17537 | 0.839142 | 0.087146 | 0.044175 | 0.170103 |
| C20:1 LPC | −0.1884 | 0.828283 | 0.085763 | 0.028039 | 0.132787 |
| C20:1 LPE | −0.07157 | 0.930933 | 0.084619 | 0.397679 | 0.674443 |
| C20:2 LPC | −0.04447 | 0.9565 | 0.088762 | 0.616337 | 0.818522 |
| C20:3 CE | −0.09186 | 0.912233 | 0.08531 | 0.281576 | 0.547872 |
| C20:3 LPC | −0.06283 | 0.939098 | 0.08699 | 0.470096 | 0.740483 |
| C20:4 CE | −0.20877 | 0.811581 | 0.084082 | 0.01303 | 0.075773 |
| C20:4 LPC | −0.10821 | 0.897439 | 0.086796 | 0.212501 | 0.465096 |
| C20:4 LPE | 0.043954 | 1.044934 | 0.087537 | 0.615586 | 0.818522 |
| C20:5 CE | −0.35711 | 0.699697 | 0.088953 | 5.96E−05 | 0.001869 |
| C20:5 LPC | −0.3047 | 0.737347 | 0.088506 | 5.76E−04 | 0.008416 |
| C22:0 Ceramide (d18:1) | −0.04226 | 0.95862 | 0.088717 | 0.633821 | 0.834602 |
| C22:0 LPE | −0.17986 | 0.835388 | 0.088013 | 0.040997 | 0.163339 |
| C22:1 MAG | 0.059611 | 1.061423 | 0.083811 | 0.476928 | 0.743534 |
| C22:4 LPC | 0.15597 | 1.168791 | 0.087353 | 0.074178 | 0.230061 |
| C22:5 CE | −0.26507 | 0.767151 | 0.084485 | 0.001704 | 0.017861 |
| C22:5 LPC | 0.013608 | 1.013701 | 0.088431 | 0.877706 | 0.948626 |
| C22:6 CE | −0.24036 | 0.786341 | 0.083139 | 0.003839 | 0.032117 |
| C22:6 LPC | −0.24217 | 0.78492 | 0.085789 | 0.004759 | 0.037177 |

TABLE 9-continued

| Metabolite | log(Hazard ratio) | Hazard ratio | se(log(Hazard ratio)) | P-value | FDR |
|---|---|---|---|---|---|
| C22:6 LPE | −0.07627 | 0.926566 | 0.085962 | 0.374941 | 0.649035 |
| C24:0 Ceramide (d18:1) | −0.09935 | 0.905428 | 0.088787 | 0.263168 | 0.52391 |
| C24:0 LPC | −0.16423 | 0.848548 | 0.088296 | 0.062888 | 0.207697 |
| C24:1 Ceramide (d18:1)-A | −0.03642 | 0.964235 | 0.087983 | 0.67891 | 0.854152 |
| C28:0 PC | −0.05436 | 0.947089 | 0.085999 | 0.527308 | 0.774002 |
| C30:0 PC | −0.02069 | 0.979525 | 0.085592 | 0.809009 | 0.925193 |
| C30:1 PC | 0.056273 | 1.057886 | 0.085506 | 0.510464 | 0.763148 |
| C31:1 PC | 0.068884 | 1.071312 | 0.084681 | 0.41596 | 0.69143 |
| C32:0 DAG | 0.086076 | 1.089889 | 0.085612 | 0.314699 | 0.585108 |
| C32:0 PC | 0.066923 | 1.069213 | 0.08506 | 0.431414 | 0.707745 |
| C32:0 PE | −0.05855 | 0.943129 | 0.085219 | 0.492035 | 0.753053 |
| C32:1 DAG | 0.086847 | 1.09073 | 0.085522 | 0.30987 | 0.580429 |
| C32:1 PC | 0.175003 | 1.19125 | 0.086011 | 0.041885 | 0.164268 |
| C32:1 PC plasmalogen-A | −0.07376 | 0.928891 | 0.085869 | 0.390327 | 0.671041 |
| C32:1 PC plasmalogen-B | 0.032682 | 1.033222 | 0.085289 | 0.70158 | 0.867139 |
| C32:2 PC | −0.06551 | 0.936592 | 0.087397 | 0.45353 | 0.739195 |
| C34:0 DAG | 0.102842 | 1.108316 | 0.084878 | 0.22565 | 0.477797 |
| C34:0 PC | −0.10925 | 0.896506 | 0.085646 | 0.202097 | 0.453276 |
| C34:0 PC plasmalogen | 0.056745 | 1.058386 | 0.085555 | 0.507165 | 0.763148 |
| C34:0 PE | −0.03659 | 0.96407 | 0.08566 | 0.669256 | 0.854152 |
| C34:0 PI | −0.15314 | 0.858012 | 0.086613 | 0.077051 | 0.23585 |
| C34:0 PS | −0.31275 | 0.731431 | 0.090181 | 5.24E−04 | 0.008416 |
| C34:1 DAG | 0.11231 | 1.11886 | 0.085168 | 0.187271 | 0.43124 |
| C34:1 PC | 0.044998 | 1.046025 | 0.085641 | 0.599292 | 0.81615 |
| C34:1 PC plasmalogen-A | −0.00962 | 0.99043 | 0.085869 | 0.910832 | 0.948626 |
| C34:1 PC plasmalogen-B | −0.17373 | 0.840525 | 0.083164 | 0.036709 | 0.156935 |
| C34:2 DAG | 0.133906 | 1.143286 | 0.084096 | 0.111318 | 0.30044 |
| C34:2 PC | −0.10495 | 0.900367 | 0.08714 | 0.228429 | 0.477797 |
| C34:2 PC plasmalogen-A | −0.26511 | 0.767119 | 0.087518 | 0.002452 | 0.022413 |
| C34:2 PC plasmalogen-B | −0.10402 | 0.901212 | 0.085419 | 0.223337 | 0.477797 |
| C34:2 PE | 0.20975 | 1.233369 | 0.08471 | 0.013283 | 0.075773 |
| C34:2 PE plasmalogen | −0.17798 | 0.836962 | 0.085207 | 0.03673 | 0.156935 |
| C34:2 PI | −0.07794 | 0.925019 | 0.085766 | 0.363475 | 0.633905 |
| C34:3 DAG | 0.090365 | 1.094574 | 0.085428 | 0.290151 | 0.555667 |
| C34:3 PC | −0.01896 | 0.98122 | 0.085998 | 0.825515 | 0.933352 |
| C34:3 PC plasmalogen | −0.33264 | 0.71703 | 0.088912 | 1.83E−04 | 0.003536 |
| C34:3 PC plasmalogen-A | −0.28892 | 0.749069 | 0.086663 | 8.56E−04 | 0.010237 |
| C34:3 PC plasmalogen-B | −0.15871 | 0.853247 | 0.086787 | 0.067445 | 0.219854 |
| C34:3 PE plasmalogen | −0.16002 | 0.852126 | 0.087892 | 0.06866 | 0.220943 |
| C34:4 PC | −0.08102 | 0.922172 | 0.086694 | 0.349996 | 0.632007 |
| C34:4 PC plasmalogen | 0.055705 | 1.057286 | 0.086407 | 0.51913 | 0.76648 |
| C34:5 PC | −0.28352 | 0.75313 | 0.09073 | 0.001779 | 0.017861 |
| C34:5 PC plasmalogen | −0.23997 | 0.786651 | 0.084673 | 0.004596 | 0.037177 |
| C35:4 PC | −0.24177 | 0.785238 | 0.0874 | 0.005671 | 0.041865 |
| C36:0 DAG-B | 0.058377 | 1.060114 | 0.082877 | 0.481199 | 0.745562 |
| C36:0 PC | −0.16669 | 0.846459 | 0.087824 | 0.05769 | 0.197158 |
| C36:0 PE | −0.11276 | 0.893363 | 0.087 | 0.194938 | 0.444814 |
| C36:1 DAG | 0.102333 | 1.107753 | 0.084695 | 0.226948 | 0.477797 |
| C36:1 PC | 0.010933 | 1.010993 | 0.086245 | 0.899128 | 0.948626 |
| C36:1 PC plasmalogen | −0.11654 | 0.889997 | 0.082526 | 0.157909 | 0.384808 |
| C36:1 PE | 0.061303 | 1.063221 | 0.084459 | 0.46794 | 0.740483 |
| C36:1 PE plasmalogen | −0.21686 | 0.805046 | 0.085373 | 0.011082 | 0.06954 |
| C36:1 PS plasmalogen | 0.085323 | 1.089069 | 0.086009 | 0.321184 | 0.592773 |
| C36:2 DAG | 0.079949 | 1.083232 | 0.084942 | 0.346591 | 0.630395 |
| C36:2 PC | −0.14879 | 0.861748 | 0.087156 | 0.087785 | 0.262295 |
| C36:2 PC plasmalogen | −0.18173 | 0.833827 | 0.084562 | 0.03163 | 0.14702 |

TABLE 9-continued

| Metabolite | log(Hazard ratio) | Hazard ratio | se(log(Hazard ratio)) | P-value | FDR |
|---|---|---|---|---|---|
| C36:2 PE | 0.139744 | 1.149979 | 0.085375 | 0.101668 | 0.282464 |
| C36:2 PE plasmalogen | −0.12982 | 0.878252 | 0.085658 | 0.129623 | 0.336038 |
| C36:2 PI | −0.1759 | 0.838702 | 0.088292 | 0.046342 | 0.171058 |
| C36:2 PS plasmalogen | 0.140812 | 1.151209 | 0.088426 | 0.111288 | 0.30044 |
| C36:3 DAG | 0.025486 | 1.025813 | 0.085697 | 0.766164 | 0.897626 |
| C36:3 PC | −0.00118 | 0.998823 | 0.085071 | 0.988956 | 0.992912 |
| C36:3 PC plasmalogen | −0.19767 | 0.82064 | 0.084095 | 0.018745 | 0.100104 |
| C36:3 PE | 0.128682 | 1.137328 | 0.085453 | 0.132101 | 0.337464 |
| C36:3 PE plasmalogen | −0.09729 | 0.907296 | 0.087253 | 0.264853 | 0.52391 |
| C36:3 PS plasmalogen | 0.194857 | 1.215137 | 0.088049 | 0.026894 | 0.129816 |
| C36:4 DAG | −0.03693 | 0.963743 | 0.086883 | 0.670789 | 0.854152 |
| C36:4 PC plasmalogen-A | −0.14082 | 0.868642 | 0.084292 | 0.094788 | 0.271026 |
| C36:4 PC plasmalogen-B | 0.006955 | 1.006979 | 0.085652 | 0.935281 | 0.958186 |
| C36:4 PC-A | −0.14542 | 0.864658 | 0.08739 | 0.096101 | 0.271026 |
| C36:4 PC-B | −0.07818 | 0.924796 | 0.084122 | 0.352688 | 0.63232 |
| C36:4 PE | 0.176759 | 1.193343 | 0.084696 | 0.036889 | 0.156935 |
| C36:4 PE plasmalogen | −0.24338 | 0.78397 | 0.08648 | 0.004888 | 0.037177 |
| C36:5 PC | −0.34558 | 0.707807 | 0.091405 | 1.56E−04 | 0.00327 |
| C36:5 PC plasmalogen | −0.15835 | 0.853554 | 0.083571 | 0.058126 | 0.197158 |
| C36:5 PC plasmalogen-A | −0.38462 | 0.680708 | 0.089412 | 1.70E−05 | 0.001064 |
| C36:5 PC plasmalogen-B | −0.17234 | 0.841693 | 0.08359 | 0.039234 | 0.163339 |
| C36:5 PE plasmalogen | −0.2911 | 0.747444 | 0.086025 | 7.15E−04 | 0.009442 |
| C37:1 PC | −0.10829 | 0.89737 | 0.085747 | 0.206638 | 0.458992 |
| C37:4 PC | −0.23244 | 0.792594 | 0.087152 | 0.007651 | 0.050534 |
| C38:1 PC | −0.25658 | 0.773695 | 0.085821 | 0.002793 | 0.024172 |
| C38:2 PC | 0.008016 | 1.008048 | 0.086133 | 0.925852 | 0.956927 |
| C38:2 PE | −0.23559 | 0.790103 | 0.088968 | 0.008096 | 0.052102 |
| C38:3 DAG | 0.061442 | 1.063368 | 0.084903 | 0.469271 | 0.740483 |
| C38:3 PC | −0.01614 | 0.983986 | 0.085367 | 0.850009 | 0.948626 |
| C38:3 PE plasmalogen | −0.30235 | 0.739082 | 0.086989 | 5.10E−04 | 0.008416 |
| C38:4 DAG | 0.09989 | 1.105049 | 0.084562 | 0.237498 | 0.492661 |
| C38:4 PC | −0.11371 | 0.892516 | 0.084688 | 0.179367 | 0.416862 |
| C38:4 PC plasmalogen | −0.01989 | 0.980311 | 0.085626 | 0.816356 | 0.927174 |
| C38:4 PE | 0.099189 | 1.104275 | 0.084471 | 0.240298 | 0.494384 |
| C38:4 PI | −0.13171 | 0.876594 | 0.086697 | 0.128705 | 0.336038 |
| C38:5 DAG | 0.011008 | 1.011069 | 0.084708 | 0.896603 | 0.948626 |
| C38:5 PE | −0.06651 | 0.935649 | 0.083773 | 0.427202 | 0.705445 |
| C38:5 PE plasmalogen | −0.23389 | 0.791447 | 0.085286 | 0.006098 | 0.043734 |
| C38:6 PC | −0.2816 | 0.754576 | 0.089152 | 0.001585 | 0.017861 |
| C38:6 PC plasmalogen | −0.34342 | 0.709338 | 0.087404 | 8.53E−05 | 0.002378 |
| C38:6 PE | 0.013603 | 1.013696 | 0.084205 | 0.871665 | 0.948626 |
| C38:6 PE plasmalogen | −0.43496 | 0.647293 | 0.086836 | 5.47E−07 | 1.33E−04 |
| C38:6 PS | 0.077103 | 1.080153 | 0.084879 | 0.363675 | 0.633905 |
| C38:7 PC plasmalogen | −0.36553 | 0.693828 | 0.086765 | 2.52E−05 | 0.001266 |
| C38:7 PE plasmalogen | −0.43154 | 0.649506 | 0.088416 | 1.06E−06 | 1.33E−04 |
| C40:1 PC | −0.19605 | 0.821974 | 0.086812 | 0.023928 | 0.120116 |
| C40:10 PC | −0.37497 | 0.687312 | 0.090699 | 3.56E−05 | 0.00149 |
| C40:11 PC plasmalogen | 0.022906 | 1.023171 | 0.086687 | 0.791594 | 0.919862 |
| C40:5 PC | −0.17137 | 0.842509 | 0.088037 | 0.051584 | 0.182362 |
| C40:6 PC | −0.21469 | 0.806789 | 0.088232 | 0.014963 | 0.081645 |
| C40:6 PC-A | −0.00791 | 0.992121 | 0.085661 | 0.926427 | 0.956927 |
| C40:6 PC-B | −0.24211 | 0.78497 | 0.089065 | 0.006561 | 0.045743 |
| C40:6 PE | −0.0269 | 0.973456 | 0.084353 | 0.749776 | 0.891913 |
| C40:7 PC plasmalogen | −0.3188 | 0.727018 | 0.083594 | 1.37E−04 | 0.00327 |
| C40:7 PC plasmalogen-A | −0.27874 | 0.756733 | 0.083451 | 8.37E−04 | 0.010237 |

TABLE 9-continued

| Metabolite | log(Hazard ratio) | Hazard ratio | se(log(Hazard ratio)) | P-value | FDR |
|---|---|---|---|---|---|
| C40:7 PC plasmalogen-B | −0.20406 | 0.815416 | 0.087441 | 0.019614 | 0.102567 |
| C40:7 PE plasmalogen | −0.40546 | 0.666667 | 0.0855 | 2.11E−06 | 1.77E−04 |
| C40:9 PC | −0.26983 | 0.763506 | 0.089063 | 0.002448 | 0.022413 |
| C42:0 TAG | −0.0505 | 0.950754 | 0.085727 | 0.555807 | 0.78375 |
| C42:11 PE plasmalogen | −0.33009 | 0.71886 | 0.087067 | 1.50E−04 | 0.00327 |
| C43:0 TAG | −0.07226 | 0.930286 | 0.084782 | 0.394028 | 0.672795 |
| C43:1 TAG | −0.02548 | 0.974838 | 0.086729 | 0.768883 | 0.897626 |
| C44:0 TAG | −0.04597 | 0.955071 | 0.085616 | 0.591321 | 0.815503 |
| C44:1 TAG | −0.0215 | 0.978731 | 0.086174 | 0.802992 | 0.924546 |
| C44:13 PE plasmalogen | −0.1456 | 0.864501 | 0.087272 | 0.09524 | 0.271026 |
| C44:2 TAG | −0.01161 | 0.988459 | 0.086769 | 0.893571 | 0.948626 |
| C45:0 TAG | −0.03451 | 0.966075 | 0.084799 | 0.684002 | 0.854152 |
| C45:1 TAG | −0.046 | 0.955039 | 0.086509 | 0.594881 | 0.815929 |
| C45:2 TAG | −0.03623 | 0.964418 | 0.086167 | 0.674149 | 0.854152 |
| C45:3 TAG-A | −0.07251 | 0.930056 | 0.087312 | 0.406272 | 0.679828 |
| C45:3 TAG-B | −0.02927 | 0.971154 | 0.087529 | 0.738072 | 0.886392 |
| C46:0 TAG | 0.011285 | 1.011349 | 0.085793 | 0.895349 | 0.948626 |
| C46:1 TAG | 0.004522 | 1.004532 | 0.086188 | 0.958161 | 0.969751 |
| C46:2 TAG | −0.01224 | 0.98783 | 0.086294 | 0.887166 | 0.948626 |
| C46:3 TAG | −0.016 | 0.984125 | 0.086992 | 0.854049 | 0.948626 |
| C46:4 TAG | −0.03619 | 0.964458 | 0.088003 | 0.680913 | 0.854152 |
| C47:0 TAG | −0.00724 | 0.992782 | 0.084832 | 0.931951 | 0.958186 |
| C47:1 TAG | −0.00197 | 0.998034 | 0.085807 | 0.981701 | 0.989586 |
| C47:2 TAG | −0.00496 | 0.99505 | 0.086133 | 0.954062 | 0.969699 |
| C48:0 TAG | 0.071817 | 1.074459 | 0.086166 | 0.404576 | 0.679828 |
| C48:1 TAG | 0.090136 | 1.094323 | 0.085578 | 0.292223 | 0.555667 |
| C48:2 TAG | 0.061801 | 1.06375 | 0.085931 | 0.472021 | 0.740483 |
| C48:3 TAG | 7.11E−04 | 1.000711 | 0.086407 | 0.993434 | 0.993434 |
| C48:4 TAG | −0.05157 | 0.949735 | 0.0873 | 0.554688 | 0.78375 |
| C48:5 TAG | −0.09913 | 0.905626 | 0.088411 | 0.26219 | 0.52391 |
| C49:0 TAG | 0.021748 | 1.021986 | 0.084995 | 0.798051 | 0.923091 |
| C49:1 TAG | 0.030705 | 1.031181 | 0.085151 | 0.7184 | 0.8698 |
| C49:2 TAG | 0.050341 | 1.05163 | 0.085283 | 0.555002 | 0.78375 |
| C49:3 TAG | 0.026556 | 1.026912 | 0.085787 | 0.756893 | 0.891925 |
| C50:0 TAG | 0.091801 | 1.096146 | 0.086288 | 0.287381 | 0.554867 |
| C50:1 TAG | 0.143065 | 1.153804 | 0.085602 | 0.094665 | 0.271026 |
| C50:2 TAG | 0.173185 | 1.189086 | 0.084728 | 0.040953 | 0.163339 |
| C50:3 TAG | 0.124321 | 1.132379 | 0.084963 | 0.143404 | 0.35638 |
| C50:4 TAG | 0.031799 | 1.03231 | 0.086035 | 0.711676 | 0.867139 |
| C50:5 TAG | −0.06069 | 0.941119 | 0.087511 | 0.48802 | 0.751491 |
| C50:6 TAG | −0.13874 | 0.870456 | 0.088815 | 0.118266 | 0.315795 |
| C51:0 TAG | −0.00484 | 0.995172 | 0.084347 | 0.954246 | 0.969699 |
| C51:1 TAG | 0.053342 | 1.05479 | 0.085106 | 0.530815 | 0.774619 |
| C51:1 TAG-B | 0.031389 | 1.031887 | 0.084874 | 0.711511 | 0.867139 |
| C51:2 TAG | 0.05247 | 1.053871 | 0.085262 | 0.538293 | 0.776504 |
| C51:3 TAG | 0.027758 | 1.028146 | 0.085582 | 0.745681 | 0.891266 |
| C52:0 TAG | 0.051657 | 1.053015 | 0.085857 | 0.547396 | 0.78375 |
| C52:1 TAG | 0.109468 | 1.115685 | 0.085848 | 0.202259 | 0.453276 |
| C52:2 TAG | 0.127273 | 1.135727 | 0.085033 | 0.134457 | 0.337487 |
| C52:3 TAG | 0.106471 | 1.112346 | 0.085512 | 0.213092 | 0.465096 |
| C52:4 TAG | 0.037198 | 1.037898 | 0.085118 | 0.662103 | 0.854152 |
| C52:5 TAG | 0.032042 | 1.032561 | 0.085279 | 0.707114 | 0.867139 |
| C52:6 TAG | −0.11947 | 0.887392 | 0.087872 | 0.173965 | 0.411936 |
| C52:7 TAG | −0.17689 | 0.837876 | 0.088404 | 0.045406 | 0.170103 |
| C53:2 TAG | 0.032532 | 1.033067 | 0.085692 | 0.704217 | 0.867139 |
| C53:3 TAG | 0.015592 | 1.015714 | 0.08645 | 0.856871 | 0.948626 |
| C54:1 TAG | 0.047759 | 1.048918 | 0.085968 | 0.578518 | 0.802254 |
| C54:10 TAG | −0.37128 | 0.689852 | 0.091438 | 4.90E−05 | 0.001756 |
| C54:2 TAG | 0.078333 | 1.081482 | 0.085154 | 0.357628 | 0.633411 |
| C54:3 TAG | 0.095205 | 1.099885 | 0.085428 | 0.265086 | 0.52391 |
| C54:4 TAG | 0.056508 | 1.058135 | 0.085332 | 0.507833 | 0.763148 |
| C54:5 TAG | 0.120162 | 1.127679 | 0.08468 | 0.155895 | 0.383624 |
| C54:6 TAG-A | −0.07802 | 0.924942 | 0.084945 | 0.358344 | 0.633411 |
| C54:7 TAG | −0.13141 | 0.876861 | 0.086758 | 0.129863 | 0.336038 |
| C54:7 TAG-A | −0.11719 | 0.889416 | 0.087215 | 0.179045 | 0.416862 |
| C54:7 TAG-B | −0.09419 | 0.910107 | 0.085771 | 0.27212 | 0.53361 |
| C54:8 TAG | −0.1957 | 0.822261 | 0.087528 | 0.025363 | 0.124824 |
| C54:9 TAG | −0.31253 | 0.731597 | 0.091115 | 6.04E−04 | 0.008416 |
| C55:2 TAG | −0.00997 | 0.990083 | 0.086055 | 0.9078 | 0.948626 |
| C55:3 TAG | 0.012126 | 1.0122 | 0.086032 | 0.887908 | 0.948626 |
| C55:6 TAG | −0.01272 | 0.987357 | 0.087008 | 0.883734 | 0.948626 |
| C56:1 TAG | 0.013708 | 1.013802 | 0.087333 | 0.875277 | 0.948626 |
| C56:10 TAG | −0.28008 | 0.755726 | 0.089381 | 0.001727 | 0.017861 |

TABLE 9-continued

| Metabolite | log(Hazard ratio) | Hazard ratio | se(log(Hazard ratio)) | P-value | FDR |
|---|---|---|---|---|---|
| C56:2 TAG | −0.04169 | 0.959169 | 0.087843 | 0.635095 | 0.834602 |
| C56:3 TAG | 0.010791 | 1.01085 | 0.086047 | 0.900198 | 0.948626 |
| C56:4 TAG | 0.04929 | 1.050525 | 0.084871 | 0.561405 | 0.787159 |
| C56:5 TAG | 0.043433 | 1.04439 | 0.083927 | 0.604796 | 0.81615 |
| C56:6 TAG | −0.08124 | 0.921971 | 0.084353 | 0.335488 | 0.614653 |
| C56:7 TAG | −0.16753 | 0.845748 | 0.0846 | 0.047669 | 0.173403 |
| C56:8 TAG | −0.18135 | 0.834142 | 0.085568 | 0.034058 | 0.153382 |
| C56:9 TAG | −0.2181 | 0.804046 | 0.087333 | 0.012514 | 0.074873 |
| C58:10 TAG | −0.21568 | 0.805992 | 0.08638 | 0.012528 | 0.074873 |
| C58:11 TAG | −0.26654 | 0.766023 | 0.088163 | 0.0025 | 0.022413 |
| C58:6 TAG | −0.08789 | 0.915863 | 0.08498 | 0.30103 | 0.56811 |
| C58:7 TAG | −0.15306 | 0.858074 | 0.085126 | 0.072163 | 0.229276 |
| C58:7 TAG-A | −0.17793 | 0.837002 | 0.086814 | 0.04041 | 0.163339 |
| C58:7 TAG-B | −0.16632 | 0.846771 | 0.084842 | 0.049947 | 0.179097 |
| C58:8 TAG | −0.1394 | 0.869881 | 0.085349 | 0.102407 | 0.282464 |
| C58:8 TAG-A | −0.22849 | 0.795733 | 0.085063 | 0.007228 | 0.049036 |
| C58:8 TAG-B | −0.17266 | 0.841423 | 0.086069 | 0.044848 | 0.170103 |
| C58:9 TAG | −0.18077 | 0.834625 | 0.085372 | 0.034221 | 0.153382 |
| C60:12 TAG | −0.21405 | 0.80731 | 0.087259 | 0.014166 | 0.079016 |

Additionally, 10-fold cross-validation was use to estimate the generalized performance of a survival predictor model created with a L2 regularized Cox proportional hazards model using the 251 lipid metabolite columns as predictor variables and determined the model to have a concordance of 0.611 (standard error=0.027) and log(hazard ratio) of 0.34993 (standard error=0.08641). Subsequently, the random seed was set to 1 and trained a L2 regularized Cox proportional hazards model using all of the Estonian Biobank cohort data for the 251 lipid metabolite columns to obtain best estimates of model coefficients for each of the lipid metabolites (Table 9).

TABLE 10

| Metabolite | log(Hazard ratio) |
|---|---|
| C14:0 CE | 3.94E-04 |
| C14:0 LPC | 1.72E-04 |
| C14:0 LPC-A | 0.001098 |
| C14:0 LPC-B | 0.001756 |
| C14:0 MAG | −0.00386 |
| C15:0 LPC | −0.00347 |
| C16:0 Ceramide (d18:1) | 0.007265 |
| C16:0 LPC | 0.004406 |
| C16:0 LPE | 0.006192 |
| C16:1 CE | 0.013105 |
| C16:1 LPC | 0.009731 |
| C16:1 LPC plasmalogen | −0.00433 |
| C16:1 MAG | 0.001008 |
| C17:0 LPC | −0.00101 |
| C18:0 CE | −0.00109 |
| C18:0 LPC | 0.001633 |
| C18:0 LPC plasmalogen-A | 0.001303 |
| C18:0 LPC-plasmalogen-A | 0.002973 |
| C18:0 LPC-plasmalogen-B | 0.008303 |
| C18:0 LPE | 0.008202 |
| C18:1 CE | −0.00242 |
| C18:1 LPC | 2.67E-04 |
| C18:1 LPC plasmalogen-B | 0.007187 |
| C18:1 LPE | −6.65E-04 |
| C18:2 CE | −0.01283 |
| C18:2 LPC | −0.01082 |
| C18:2 LPE | 0.005299 |
| C18:3 CE | −0.00678 |
| C18:3 LPC | −0.00491 |
| C20:0 LPE | −0.00398 |

TABLE 10-continued

| Metabolite | log(Hazard ratio) |
|---|---|
| C20:1 LPC | −0.00485 |
| C20:1 LPE | 0.002509 |
| C20:2 LPC | 0.002908 |
| C20:3 CE | −0.00677 |
| C20:3 LPC | −0.00711 |
| C20:4 CE | −0.01055 |
| C20:4 LPC | −0.00495 |
| C20:4 LPE | 0.002858 |
| C20:5 CE | −0.01408 |
| C20:5 LPC | −0.01341 |
| C22:0 Ceramide (d18:1) | 0.001099 |
| C22:0 LPE | −0.00242 |
| C22:1 MAG | 0.008272 |
| C22:4 LPC | 0.009913 |
| C22:5 CE | −0.01326 |
| C22:5 LPC | 4.81E-04 |
| C22:6 CE | −0.00718 |
| C22:6 LPC | −0.00718 |
| C22:6 LPE | 0.005454 |
| C24:0 Ceramide (d18:1) | −0.00143 |
| C24:0 LPC | 5.11E-05 |
| C24:1 Ceramide (d18:1)-A | 0.003769 |
| C28:0 PC | −0.00343 |
| C30:0 PC | 9.38E-04 |
| C30:1 PC | 0.004872 |
| C31:1 PC | 0.007144 |
| C32:0 DAG | 2.17E-04 |
| C32:0 PC | 0.013643 |
| C32:0 PE | 0.001223 |
| C32:1 DAG | 0.002053 |
| C32:1 PC | 0.012646 |
| C32:1 PC plasmalogen-A | −1.54E-05 |
| C32:1 PC plasmalogen-B | 0.013756 |
| C32:2 PC | 8.60E-05 |
| C34:0 DAG | 0.003 |
| C34:0 PC | 0.001523 |
| C34:0 PC plasmalogen | 0.007627 |
| C34:0 PE | 0.002072 |
| C34:0 PI | −0.00977 |
| C34:0 PS | −0.00695 |
| C34:1 DAG | 0.002131 |
| C34:1 PC | 0.003556 |
| C34:1 PC plasmalogen-A | 0.004432 |
| C34:1 PC plasmalogen-B | −0.00712 |
| C34:2 DAG | 0.004388 |
| C34:2 PC | −0.00572 |
| C34:2 PC plasmalogen-A | −0.01478 |
| C34:2 PC plasmalogen-B | 0.00379 |

TABLE 10-continued

| Metabolite | log(Hazard ratio) |
|---|---|
| C34:2 PE | 0.011383 |
| C34:2 PE plasmalogen | −0.0027 |
| C34:2 PI | −0.00707 |
| C34:3 DAG | 0.002958 |
| C34:3 PC | 0.001272 |
| C34:3 PC plasmalogen | −0.01621 |
| C34:3 PC plasmalogen-A | −0.01336 |
| C34:3 PC plasmalogen-B | −2.18E−04 |
| C34:3 PE plasmalogen | −0.00291 |
| C34:4 PC | 6.48E−04 |
| C34:4 PC plasmalogen | 0.005892 |
| C34:5 PC | −0.00657 |
| C34:5 PC plasmalogen | −0.00991 |
| C35:4 PC | −0.00865 |
| C36:0 DAG-B | −0.00257 |
| C36:0 PC | −0.00113 |
| C36:0 PE | −0.00153 |
| C36:1 DAG | 0.00392 |
| C36:1 PC | 0.006107 |
| C36:1 PC plasmalogen | −0.00262 |
| C36:1 PE | 0.002499 |
| C36:1 PE plasmalogen | −0.0068 |
| C36:1 PS plasmalogen | 0.011356 |
| C36:2 DAG | −8.89E−05 |
| C36:2 PC | −0.00678 |
| C36:2 PC plasmalogen | −0.00689 |
| C36:2 PE | 0.007359 |
| C36:2 PE plasmalogen | 6.55E−04 |
| C36:2 PI | −0.00829 |
| C36:2 PS plasmalogen | 0.018083 |
| C36:3 DAG | −0.0012 |
| C36:3 PC | −3.49E−04 |
| C36:3 PC plasmalogen | −0.00858 |
| C36:3 PE | 0.008743 |
| C36:3 PE plasmalogen | 0.002562 |
| C36:3 PS plasmalogen | 0.010772 |
| C36:4 DAG | −0.00462 |
| C36:4 PC plasmalogen-A | −0.00645 |
| C36:4 PC plasmalogen-B | 0.007161 |
| C36:4 PC-A | −0.00609 |
| C36:4 PC-B | −0.00309 |
| C36:4 PE | 0.009896 |
| C36:4 PE plasmalogen | −0.00961 |
| C36:5 PC | −0.01089 |
| C36:5 PC plasmalogen | −0.00293 |
| C36:5 PC plasmalogen-A | −0.01413 |
| C36:5 PC plasmalogen-B | −0.00428 |
| C36:5 PE plasmalogen | −0.01629 |
| C37:1 PC | 1.49E−04 |
| C37:4 PC | −0.00917 |
| C38:1 PC | −0.00951 |
| C38:2 PC | 0.009512 |
| C38:2 PE | −0.00988 |
| C38:3 DAG | 0.001676 |
| C38:3 PC | −0.00359 |
| C38:3 PE plasmalogen | −0.01362 |
| C38:4 DAG | 0.004829 |
| C38:4 PC | −0.0042 |
| C38:4 PC plasmalogen | 7.22E−04 |
| C38:4 PE | 0.002245 |
| C38:4 PI | −0.00381 |
| C38:5 DAG | 1.29E−04 |
| C38:5 PE | −0.00227 |
| C38:5 PE plasmalogen | −0.01259 |
| C38:6 PC | −0.00737 |
| C38:6 PC plasmalogen | −0.01029 |
| C38:6 PE | 0.005685 |
| C38:6 PE plasmalogen | −0.01756 |
| C38:6 PS | 0.005939 |
| C38:7 PC plasmalogen | −0.01172 |
| C38:7 PE plasmalogen | −0.01539 |
| C40:1 PC | −0.00354 |
| C40:10 PC | −0.01259 |
| C40:11 PC plasmalogen | 0.003632 |
| C40:5 PC | −0.00767 |
| C40:6 PC | −0.00462 |
| C40:6 PC-A | −0.00153 |
| C40:6 PC-B | −0.00665 |
| C40:6 PE | 1.98E−04 |
| C40:7 PC plasmalogen | −0.00997 |
| C40:7 PC plasmalogen-A | −0.0095 |
| C40:7 PC plasmalogen-B | −1.93E−04 |
| C40:7 PE plasmalogen | −0.01568 |
| C40:9 PC | −0.00606 |
| C42:0 TAG | −0.00726 |
| C42:11 PE plasmalogen | −0.00859 |
| C43:0 TAG | −0.01028 |
| C43:1 TAG | −0.00226 |
| C44:0 TAG | −0.00817 |
| C44:1 TAG | −0.00434 |
| C44:13 PE plasmalogen | −0.01228 |
| C44:2 TAG | −0.00209 |
| C45:0 TAG | −0.00787 |
| C45:1 TAG | −0.00555 |
| C45:2 TAG | −0.00364 |
| C45:3 TAG-A | −0.00526 |
| C45:3 TAG-B | 4.76E−04 |
| C46:0 TAG | −0.00405 |
| C46:1 TAG | −0.00419 |
| C46:2 TAG | −0.00429 |
| C46:3 TAG | −0.0023 |
| C46:4 TAG | −0.00152 |
| C47:0 TAG | −0.00457 |
| C47:1 TAG | −0.00308 |
| C47:2 TAG | −8.13E−04 |
| C48:0 TAG | 2.08E−04 |
| C48:1 TAG | 0.00221 |
| C48:2 TAG | −6.43E−05 |
| C48:3 TAG | −0.00226 |
| C48:4 TAG | −0.00502 |
| C48:5 TAG | −0.00507 |
| C49:0 TAG | −7.21E−04 |
| C49:1 TAG | −9.01E−04 |
| C49:2 TAG | 0.001153 |
| C49:3 TAG | 0.001533 |
| C50:0 TAG | 0.003209 |
| C50:1 TAG | 0.004147 |
| C50:2 TAG | 0.006326 |
| C50:3 TAG | 0.004667 |
| C50:4 TAG | 0.001927 |
| C50:5 TAG | −0.00183 |
| C50:6 TAG | −0.00433 |
| C51:0 TAG | −0.00331 |
| C51:1 TAG | 0.001087 |
| C51:1 TAG-B | 8.58E−05 |
| C51:2 TAG | 3.87E−04 |
| C51:3 TAG | −7.22E−04 |
| C52:0 TAG | 2.91E−04 |
| C52:1 TAG | 0.004703 |
| C52:2 TAG | 0.00281 |
| C52:3 TAG | 0.002883 |
| C52:4 TAG | −8.02E−04 |
| C52:5 TAG | 4.54E−04 |
| C52:6 TAG | −0.00372 |
| C52:7 TAG | −0.00481 |
| C53:2 TAG | −1.64E−05 |
| C53:3 TAG | −0.00118 |
| C54:1 TAG | 0.001696 |
| C54:10 TAG | −0.02482 |
| C54:2 TAG | 0.002772 |
| C54:3 TAG | 0.004038 |
| C54:4 TAG | 0.002203 |
| C54:5 TAG | 0.006991 |
| C54:6 TAG-A | −0.00279 |
| C54:7 TAG | −0.00265 |
| C54:7 TAG-A | −0.00574 |
| C54:7 TAG-B | 0.003651 |
| C54:8 TAG | −0.00419 |
| C54:9 TAG | −0.0122 |
| C55:2 TAG | 2.07E−04 |
| C55:3 TAG | 0.001115 |
| C55:6 TAG | −0.00124 |
| C56:1 TAG | 0.001449 |
| C56:10 TAG | −0.00867 |

TABLE 10-continued

| Metabolite | log(Hazard ratio) |
|---|---|
| C56:2 TAG | −0.00161 |
| C56:3 TAG | 9.86E−04 |
| C56:4 TAG | 0.00366 |
| C56:5 TAG | 0.001113 |
| C56:6 TAG | −0.00272 |
| C56:7 TAG | −0.00522 |
| C56:8 TAG | −0.00386 |
| C56:9 TAG | −0.00486 |
| C58:10 TAG | −0.00374 |
| C58:11 TAG | −0.00632 |
| C58:6 TAG | −0.0011 |
| C58:7 TAG | −0.00311 |
| C58:7 TAG-A | −0.00529 |
| C58:7 TAG-B | −0.00389 |
| C58:8 TAG | −0.00152 |
| C58:8 TAG-A | −0.01177 |
| C58:8 TAG-B | −0.00304 |
| C58:9 TAG | −0.00201 |
| C60:12 TAG | −0.00281 |

Metabolite: The identity of a lipid metabolite in the Estonian Biobank cohort data.
Log(Hazard ratio): The coefficient of a metabolite in a L2 regularized Cox proportional hazards model for all-cause mortality.

Example 16: Building Survival Predictor Models Using Lipids Present in Both the Estonian Biobank and Framingham Offspring Cohort Data Survival predictor models were created with the subset of lipid metabolites present in both the Estonian Biobank and Framingham Offspring cohort data. This process provided additional validation for the process of creation of survival predictor models from lipid metabolites.

There are 91 lipid metabolites present in both the Estonian Biobank and Framingham Offspring cohort datasets, which are referred to hereafter as the set of "overlapping lipid metabolites".

10-fold cross-validation was used to estimate the generalization performance of a survival predictor model created with a L2 regularized Cox proportional hazards model using the overlapping lipid metabolites in the Estonian Biobank dataset as predictor variables and determined the model to have a concordance of 0.6 (standard error=0.027) and log (hazard ratio) of 0.29596 (standard error=0.08589). Subsequently, the random seed was set to 1 and a L2 regularized Cox proportional hazards model was trained using all the Estonian Biobank cohort data for the overlapping lipid metabolites to obtain best estimates of model coefficients for each of the lipid metabolites (Table 10).

TABLE 11

| Metabolite | Log(Hazard ratio) |
|---|---|
| C14:0 CE | −0.00695 |
| C14:0 LPC | −0.00719 |
| C16:0 LPC | 0.014759 |
| C16:0 LPE | 0.017687 |
| C16:1 CE | 0.049694 |
| C16:1 LPC | 0.033405 |
| C18:0 CE | −0.01052 |
| C18:0 LPC | 0.003746 |
| C18:0 LPE | 0.028981 |
| C18:1 CE | −0.00748 |
| C18:1 LPC | −0.00273 |
| C18:1 LPE | −0.00159 |
| C18:2 CE | −0.05119 |
| C18:2 LPC | −0.04328 |
| C18:2 LPE | 0.02629 |
| C18:3 CE | −0.02135 |
| C20:3 CE | −0.0175 |
| C20:3 LPC | −0.02619 |
| C20:4 CE | −0.03909 |
| C20:4 LPC | −0.01808 |
| C20:4 LPE | 0.011128 |
| C20:5 CE | −0.05914 |
| C20:5 LPC | −0.05372 |
| C22:6 CE | −0.02545 |
| C22:6 LPC | −0.02407 |
| C22:6 LPE | 0.028807 |
| C32:0 PC | 0.054327 |
| C32:1 PC | 0.042704 |
| C32:2 PC | −0.00565 |
| C34:1 DAG | 0.003211 |
| C34:1 PC | 0.004455 |
| C34:2 DAG | 0.014343 |
| C34:2 PC | −0.02489 |
| C34:3 PC | 0.004383 |
| C34:4 PC | −3.98E−05 |
| C36:1 DAG | 0.011402 |
| C36:1 PC | 0.011992 |
| C36:2 DAG | −0.00843 |
| C36:2 PC | −0.03675 |
| C36:3 PC | −0.00237 |
| C36:4 PC-A | −0.0301 |
| C36:4 PC-B | −0.01296 |
| C38:2 PC | 0.029394 |
| C38:3 PC | −0.01732 |
| C38:4 PC | −0.01879 |
| C38:6 PC | −0.0332 |
| C40:6 PC | −0.01718 |
| C44:1 TAG | −0.02409 |
| C46:0 TAG | −0.02452 |
| C46:1 TAG | −0.02339 |
| C46:2 TAG | −0.02359 |
| C48:0 TAG | −0.00552 |
| C48:1 TAG | 6.07E−04 |
| C48:2 TAG | −0.00857 |
| C48:3 TAG | −0.01277 |
| C48:4 TAG | −0.02161 |
| C50:1 TAG | 0.010082 |
| C50:2 TAG | 0.016754 |
| C50:3 TAG | 0.013676 |
| C50:4 TAG | 0.006518 |
| C50:5 TAG | −0.00695 |
| C52:1 TAG | 0.014186 |
| C52:2 TAG | 0.004607 |
| C52:3 TAG | 0.012052 |
| C52:4 TAG | −2.76E−04 |
| C52:5 TAG | 0.007663 |
| C52:6 TAG | −0.01177 |
| C54:1 TAG | 0.003049 |
| C54:2 TAG | 0.007686 |
| C54:3 TAG | 0.015228 |
| C54:4 TAG | 0.012164 |
| C54:5 TAG | 0.03349 |
| C54:7 TAG | −0.00634 |
| C54:8 TAG | −0.01067 |
| C54:9 TAG | −0.04507 |
| C56:10 TAG | −0.02726 |
| C56:2 TAG | −0.00978 |
| C56:3 TAG | 0.001693 |
| C56:4 TAG | 0.01663 |
| C56:5 TAG | 0.006268 |
| C56:6 TAG | −0.00738 |
| C56:7 TAG | −0.01844 |
| C56:8 TAG | −0.00849 |
| C56:9 TAG | −0.01227 |
| C58:10 TAG | −0.00517 |
| C58:11 TAG | −0.01846 |
| C58:6 TAG | −0.00314 |
| C58:7 TAG | −0.00876 |
| C58:8 TAG | −0.00187 |

TABLE 11-continued

| Metabolite | Log(Hazard ratio) |
|---|---|
| C58:9 TAG | 0.001739 |
| C60:12 TAG | −0.0048 |

Metabolite: The identity of an overlapping lipid metabolite in the Estonian Biobank cohort data.
Log(Hazard ratio): The coefficient of a metabolite in a L2 regularized Cox proportional hazards model for all-cause mortality.

Additionally, using the Framingham Offspring data, the set of overlapping lipid metabolites was controlled for the following clinical covariates: age, blood glucose level, BMI, estimated LDL cholesterol, cigarettes smoked per day, creatinine, smoking status, diastolic blood pressure, definite left ventricular hypertrophy, fasting blood glucose, HDL cholesterol, height, hip girth, systolic blood pressure, total cholesterol, triglyceride count, ventricular rate per minute by ECG, waist girth, weight, treatment status for diabetes, treatment status for high blood pressure, and treatment status for high cholesterol. Subsequently, the Framingham Offspring overlapping lipid metabolites data was normalized with an inverse rank transformation as described above.

The L2 regularized Cox proportional hazards model trained on the overlapping lipid metabolites in the Estonian Biobank data was used, with coefficients given previously as Table 10, and estimated its predictive performance on the Framingham Offspring dataset. The model was determined to have a concordance of 0.542 (standard error=0.02) and log(hazard ratio) of 0.14814 (standard error=0.06669). In the Framingham Offspring cohort, the median death occurred 16.12466 years after the time of metabolomics blood sample collection, with a minimum of 11.04795 years and a maximum of 22.76986 years. There were 232 deaths recorded in the data. Accordingly, the resulting estimation of the generalized performance of a survival predictor model trained on the set of overlapping lipid metabolites in the Framingham Offspring dataset demonstrated that a biomarker, or survival predictor model, constructed using lipid metabolites can be used to predict death at least 11 years in advance in a population of substantially different ethnic background even after controlling for standard clinical covariates.

For each value of n=10, 11, 12, 13, 14, 15, 16, 17, 18, 19, 20, 21, and 22, the aforementioned L2 regularized Cox proportional hazards model trained on the overlapping lipid metabolites in the Estonian Biobank data was used, with coefficients given previously in Table 10, and estimated its predictive performance on the Framingham Offspring dataset, excluding participants for whom fewer than n years of follow up data were recorded, with the hazard ratios, concordances, and p-values reported in Table 11. These results demonstrate that the survival predictor model trained on the lipid metabolites of the Estonian population can be used to predict mortality up to 17 years in advance in a population of substantially different ethnic background even after controlling for standard clinical covariates.

Table 12 (n: The number of years of follow up data under which participants were excluded. Log(HR): The logarithm of the hazard ratio of the L2 regularized Cox proportional hazards model trained on the overlapping lipid metabolites in the Estonian Biobank data evaluated on the corresponding subset of the Framingham Offspring data. HR: The hazard ratio of the L2 regularized Cox proportional hazards model trained on the overlapping lipid metabolites in the Estonian Biobank data evaluated on the corresponding subset of the Framingham Offspring data. Se(log(HR)): The standard error of the logarithm of the hazard ratio of the L2 regularized Cox proportional hazards model trained on the overlapping lipid metabolites in the Estonian Biobank data evaluated on the corresponding subset of the Framingham Offspring data. P-value: The p-value of the statistical test for significance of the hazard ratio of the L2 regularized Cox proportional hazards model trained on the overlapping lipid metabolites in the Estonian Biobank data evaluated on the corresponding subset of the Framingham Offspring data. Concordance: The concordance index of the L2 regularized Cox proportional hazards model trained on the overlapping lipid metabolites in the Estonian Biobank data evaluated on the corresponding subset of the Framingham Offspring data. Se(Concordance): The standard error of the concordance index of the L2 regularized Cox proportional hazards model trained on the overlapping lipid metabolites in the Estonian Biobank data evaluated on the corresponding subset of the Framingham Offspring data.)

TABLE 12

| n | Log(HR) | HR | Se(log(HR)) | P-value | Concordance | Se(Concordance) |
|---|---|---|---|---|---|---|
| 10 | 0.147813 | 1.159296 | 0.06654 | 0.026324 | 0.542036 | 0.019821 |
| 11 | 0.147966 | 1.159473 | 0.066609 | 0.026324 | 0.542036 | 0.019821 |
| 12 | 0.149155 | 1.160853 | 0.067018 | 0.02604 | 0.542479 | 0.019958 |
| 13 | 0.160291 | 1.173852 | 0.068071 | 0.018535 | 0.547409 | 0.020241 |
| 14 | 0.154259 | 1.166793 | 0.070624 | 0.028946 | 0.549669 | 0.02106 |
| 15 | 0.277906 | 1.320362 | 0.080995 | 6.01E-04 | 0.591773 | 0.024369 |
| 16 | 0.208448 | 1.231764 | 0.091821 | 0.023198 | 0.568162 | 0.028097 |
| 17 | 0.275065 | 1.316616 | 0.110453 | 0.012762 | 0.587643 | 0.034658 |
| 18 | 0.189619 | 1.208789 | 0.126051 | 0.132502 | 0.557895 | 0.040461 |
| 19 | 0.225805 | 1.253332 | 0.145769 | 0.121366 | 0.585377 | 0.047577 |
| 20 | 0.105329 | 1.111076 | 0.192099 | 0.583482 | 0.55202 | 0.063339 |
| 21 | −0.18183 | 0.833742 | 0.251866 | 0.470333 | 0.574977 | 0.083196 |
| 22 | −0.03419 | 0.966392 | 0.586396 | 0.953511 | 0.56 | 0.190865 |

Additional Considerations

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Various embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Various embodiments may also relate to a computer data signal embodied in a carrier wave, where the computer data signal includes any embodiment of a computer program product or other data combination described herein. The computer data signal is a product that is presented in a tangible medium or carrier wave and modulated or otherwise encoded in the carrier wave, which is tangible, and transmitted according to any suitable transmission method.

All publications, patents, and patent applications mentioned in this specification are herein incorporated by reference to the same extent as if each individual publication, patent, or patent application was specifically and individually indicated to be incorporated by reference.

While many embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A method for determining a survival metric for a subject, comprising:
    obtaining a dataset associated with a sample from the subject comprising metabolite values for each of at least n survival, each metabolite value representing a presence of metabolites corresponding to the survival biomarker, the dataset generated for the sample using at least one survival biomarker detection assay;
    accessing a default state representing a subject having normalized metabolite values for each of the n survival biomarkers, each normalized metabolite value determined based on a distribution of metabolites for the corresponding survival biomarker within a set of samples from a population of subjects;
    for each of the n survival biomarkers, comparing the metabolite value in the obtained dataset associated with the sample from the subject to a corresponding normalized metabolite value in the default state to determine a relative metabolite value, wherein each relative metabolite value represents an abundance or lack of metabolites for the corresponding survival biomarker in the sample from the subject compared to the default state;
    encoding the determined relative metabolite values into a vector representation;
    inputting the vector representation into a survival predictor model comprising coefficients for the n survival biomarkers to generate a survival metric value representing a relative survival risk of the subject compared to the default state, wherein the survival predictor model is a machine-learning model iteratively trained using a training dataset including a set of survival biomarkers labeled to determine the coefficients of the survival predictor model, the set of survival biomarkers comprising the at least n survival biomarkers of the obtained dataset; and
    providing the survival metric value.

2. The method of claim 1, wherein obtaining the dataset associated with the sample from the subject further comprises performing at least one survival biomarker detection assay.

3. The method of claim 1, wherein the survival metric value is indicative of the subject's relative survival risk.

4. The method of claim 3, wherein the survival metric value is indicative of the subject's relative likelihood of contracting an aging-related disease, chance of survival, or chance of death.

5. The method of claim 1 further comprising:
    obtaining data representing at least one aging indicator from the subject, wherein an aging indicator is an observable characteristic of the subject that correlates with the subject's relative likelihood of mortality; and
    encoding the vector representation based on a numerical value representing a measurement of the at least one aging indicator and metabolite values measured for the n survival biomarkers.

6. The method of claim 5, wherein the accessed default state further comprises normalized measurements of the at least one aging indicator.

7. The method of claim 5, wherein the at least one aging indicator is one of: age, sex, race, ethnicity, smoking status, alcohol consumption status, diastolic blood pressure, systolic blood pressure, a family history parameter, a medical history parameter, a medical symptom parameter, height, weight, a body-mass index, and resting heart rate of a subject.

8. The method of claim 5, wherein encoding the vector representation further comprises:
   mathematically combining the numerical value representing the measurement of the at least one aging indicator with the metabolite values for the n survival biomarkers to encode the vector representation; and
   inputting the vector representation to the survival predictor model to generate the survival metric value.

9. The method of claim 1, wherein the n survival biomarkers are selected from a list generated by:
   a. obtaining a metabolite dataset associated with a sample from one or more subjects in a study group comprising data representing a presence or an abundance of at least m metabolites;
   b. obtaining a clinical factor dataset from the one or more subjects in a study group comprising data representing the value of at least 1 aging indicators;
   c. determining a list of k significant metabolites, wherein each significant metabolite is associated with one or more aging indicators of the at least 1 aging indicators; and
   d. selecting n metabolites from the list of significant metabolites as survival biomarkers.

10. The method of claim 1, wherein n is between 2 and 661, inclusive.

11. The method of claim 2, wherein the survival biomarker detection assay comprises a biological sample that is collected from a single cell, multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, a bodily fluid, a swab, or an extract thereof.

12. The method of claim 1, wherein the survival predictor model comprises a Cox proportional hazards model.

13. The method of claim 1, wherein at least one of the survival biomarkers is glucuronate.

14. The method of claim 1, wherein at least one of the survival biomarkers is citrate.

15. The method of claim 1, wherein at least one of the survival biomarkers is adipic acid.

16. The method of claim 1, wherein at least one of the survival biomarkers is isocitrate.

17. The method of claim 1, wherein at least one of the survival biomarkers is lactate.

18. The method of claim 1, wherein the survival biomarkers comprises at least one subclass of lipids.

* * * * *

UNITED STATES PATENT AND TRADEMARK OFFICE
CERTIFICATE OF CORRECTION

PATENT NO. : 11,881,311 B1
APPLICATION NO. : 15/891295
DATED : January 23, 2024
INVENTOR(S) : Fortney et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1324 days.

Signed and Sealed this
First Day of July, 2025

Coke Morgan Stewart
*Acting Director of the United States Patent and Trademark Office*